United States Patent [19]
Bedbrook et al.

[11] Patent Number: 5,378,824
[45] Date of Patent: * Jan. 3, 1995

[54] NUCLEIC ACID FRAGMENT ENCODING HERBICIDE RESISTANT PLANT ACETOLACTATE SYNTHASE

[75] Inventors: John R. Bedbrook, Piedmont, Calif.; Roy S. Chaleff, Pennington, N.J.; Saverio C. Falco, Arden; Barbara J. Mazur, Wilmington, both of Del.; Christopher R. Somerville, Okemon, Mich.; Narendra S. Yadav, Wilmington, Del.

[73] Assignee: E. I. Du Pont de Nemours and Company, Wilmington, Del.

[*] Notice: The portion of the term of this patent subsequent to May 7, 2008 has been disclaimed.

[21] Appl. No.: 892,305

[22] Filed: Jun. 2, 1992

Related U.S. Application Data

[60] Division of Ser. No. 642,976, Jan. 18, 1991, Pat. No. 5,141,870, which is a division of Ser. No. 164,360, Mar. 4, 1988, Pat. No. 5,013,659, which is a continuation-in-part of Ser. No. 900,609, Aug. 26, 1986, abandoned.

[30] Foreign Application Priority Data

Jul. 27, 1987 [IL] Israel ........................ 83348

[51] Int. Cl.$^6$ ..................... C07H 21/04; C12P 21/00; C12P 21/04; C12N 15/00
[52] U.S. Cl. ................... 536/23.6; 536/23.2; 435/69.1; 435/70.1; 435/172.1
[58] Field of Search ............ 536/23.2, 23.6; 435/69.1, 70.1, 172.1

[56] References Cited

U.S. PATENT DOCUMENTS

| | | | |
|---|---|---|---|
| 4,626,505 | 12/1986 | Falco | 435/172.3 |
| 4,757,011 | 7/1988 | Chaleff | 435/172.1 |
| 4,761,373 | 8/1988 | Anderson | 435/172.3 |
| 4,774,381 | 9/1988 | Chaleff | 800/230 |
| 5,013,659 | 5/1991 | Bedbrook et al. | 435/172.3 |
| 5,141,870 | 8/1992 | Bedbrook et al. | 435/320.1 |

FOREIGN PATENT DOCUMENTS 0154204 11/1985 European Pat. Off.

OTHER PUBLICATIONS

Friden, et al., The ilvB Locus of E. Coli K-12 is an Operon Encoding both Subunits of ALS, Nucleic Acids Res., 13:3979-3993 (1985).
Wek, et al., The Nucleotide Sequence of the ilvBN Operon of E. Coli Sequence Homologies of ALS Iozymes; Nucleic Acids Res., 13:399-4010 (1985).
Falco, et al., Genetic Analysis of Mutants of Sacch. Cere. Resistant to the Herbicide Sulfometuron Methyl, Genetics 109:21-35 (1985).
Falco et al., Nucleotide Sequence of the yeast ILV2 Gene which Encodes Acetolactate Synthase, Nucleic Acids Res., 13:4011-4027 (1985).
Yadav et al., Single Amino Acid Substitutions in the Enzyme Acetolactate Synthase, Proc. Nal. Acad. Sci USA 83:4418-4422 (1986).
Chaleff, R. S., and Ray, T. B., Herbicide-Resistant Mutants from Tobacco Cell Cultures, Science 223:1148-1151 (1984).
Chaleff, R. S. and Mauvais, J., Acetolactate Synthase is the Site of Action of Two Sulfonylurea Herbicides in Higher Plants, Science 224:1443-1445 (1984).
Mazur, B. J., et al., Cloning Herbicide Resistance Genes (List continued on next page.)

*Primary Examiner*—David T. Fox

[57] ABSTRACT

A nucleic acid fragment encoding a herbicide-resistant plant acetolactate synthase protein is disclosed. This nucleic acid fragment contains at least one nucleotide mutation resulting in one amino acid change in one of seven substantially conserved regions of acetolactate synthase amino acid homology. This mutation results in the production of an acetolactate synthase protein which is resistant to sulfonylurea herbicide compounds compared to the wild-type protein. Transformation of herbicide sensitive plants or plant cells with the fragment results in resistance to the herbicide.

1 Claim, 26 Drawing Sheets

OTHER PUBLICATIONS into and out of Plants Biotech '85 USA: Online Publications, Pinner, UK, pp. 97–103, 1985.

Haughn, G. W. and Somerville, C. R., Sulfonylurea Resistant Mutants of Arabidopsis thaliana, Mol. Gen. Genet. 204-434 (1986).

Anderson, P. C. and Georgeson, M., An Imidazolinone and Sulfonylurea tolerant Mutant of Corn, J. Cell. Biochem, suppl. 10C:43 (1986).

Lawther et al., Molecular Basis of Valine Resistance in E. Coli K-12, Proc. Natl., Acad., Sci. USA, 78(2):922–925 (1981).

Squires et al., Molecular Structure of ilvIH and its Evolutionary Relationship to ilvG in E. Coli K12: Nucleic Acids Res. 11(15):5299–5314 (1983).

La Rossa et al., Trends in Biotech., 2:158–161 (1984).

Falco et al., Biotechnology in Plant Science: Relevance to Agriculture in the Eighties (1985).

Falco et al., Molecular Form and Function of the Plant Genome (1985).

Chaleff et al., "Developing Plant Varieties Resistant to Sulfonylurea Herbicides", UCLA Sym. Ser., vol. 48, UCLA Symp. Molecular Strategies for Crop Protection held Mar. 30–Apr. 6, 1986, pp. 415–425.

Estelle et al., "The Mutants of Arabidopsis", Trends in Genetics, pp. 89–93 (1986).

Mazur et al., "Acetolactate Synthase, the Target Enzyme of the Sulfonylurea Herbicides", NATO ASI SER. A., vol. 140, Plant Mol. Biol., edited by Diter von Wettstein and Nam–Hai Chua, Proceedings of NATO Adv. Study Inst. on Plant Mol. biol, Cansberg, Jun. 10–19, 1987.

Somerville et al., "Selection for herbicide resistance at the whole plant level", Bid. Abstr./BR 30:79417 (1986).

FIG.4A

```
             10                  30                  50
CTGCAGGTCGACTCTAGTGTACAAGATTGGGATGTGAAGGCTCAAGGATGTGAATTGATA
             70                  90                 110
CTCTCATCAGGGGGAGTTAATACGTGTTGTACTCTTTTTTCCTTACAAGATTTTGACCCA
            130                 150                 170
CTGGGTTTTTCTTGCAAGGTTTTTAACGAGGCAACCAAAAGGCGTATTTCTAAACATGTG
            190                 210                 230
TACTTTTTTTCCTTCACTAGGATTTTTTTCCTATATGATTTTTTCCTAATAAGGTTTTAA
            250                 270                 290
CGAGGCACATTATCTATGGACATCCAAGGGGAGTGTTATAAGAAAAATCAAATTATGGT
            310                 330                 350
GGATGTCTACTCTTCCTCCATGATCTTCTCAAATGCTTAATGACATATTCAATGACATAT
            370                 390                 410
TTCTATGCTTAATGACATATTTTCTTCACTTTTCATGCCTATATAAAGGCCTTGTAATA
            430                 450                 470
GATAGAAAAATACAAATAATTGAAGAAGAAATAAAAATCTCTTATCTCTATATTTCTTAG
            490                 510                 530
CTTGTTTTTTTTTGTTCTATATTGTTACTTTGAGCTATATTTCATAACAGCATTCACAT
            550                 570                 590
TCTTTTTCCATAGTCTTTTTTCCCTTTTATATTTTAATTTACTGAAGTAACAAATACTTC
            610                 630                 650
CACTTCTTTCTTCTTCCCACCCTCCTAAATATATCCAACATCTCATTTTTCTTTTCCCCA
            670                 690                 710
ATTCTCAGACATTTTAATCTTTCTTTTCTATTTATTTTCTTCATATTTTGATCTCTCTTC
            730                 750                 770
CATTTGTTCTCATCCATTTTCGCTATTCACGTGAATTCAATCAAGTAGGACCCTTTCAGT
            790                 810                 830
TTCGTGGCGCTCTCGTCTTCTCAGCTTAATATAAAACCAACCACACACCATCTACATTGC
            850                 870                 890
CCTTTCCTTTCAGTTTCGTCTCTCACTGCTCTCATTCAACAATAATGGCGGCGGCTGCGG
                                                   M  A  A  A  A  A
            910                 930                 950
CGGCTCCATCTCCCTCTTTCTCCAAAACCCTATCGTCCTCCTCCTCCAAATCCTCCACCC
 A  P  S  P  S  F  S  K  T  L  S  S  S  S  S  K  S  S  T  L
```

FIG.4B

```
              970                    990                   1010
     TCCTCCCTAGATCCACCTTCCCTTTCCCCCACCACCCCCACAAAACCACCCCACCACCCC
       L  P  R  S  T  F  P  F  P  H  H  P  H  K  T  T  P  P  P  L 1030                   1050                   1070
     TCCACCTCACCCCCACCCACATTCACAGCCAACGCCGTCGTTTCACCATCTCCAATGTCA
       H  L  T  P  T  H  I  H  S  Q  R  R  R  F  T  I  S  N  V  I 1090                   1110                   1130
     TTTCCACTACCCAAAAAGTTTCCGAGACCCAAAAAGCCGAAACTTTCGTTTCCCGTTTTG
       S  T  T  Q  K  V  S  E  T  Q  K  A  E  T  F  V  S  R  F  A 1150                   1170                   1190
     CCCCTGACGAACCCAGAAAGGGTTCCGACGTTCTCGTGGAGGCCCTCGAAAGAGAAGGGG
       P  D  E  P  R  K  G  S  D  V  L  V  E  A  L  E  R  E  G  V 1210                   1230                   1250
     TTACGGACGTTTTTGCGTACCCAGGCGGCGCTTCCATGGAGATTCACCAAGCTTTGACGC
       T  D  V  F  A  Y  P  G  G  A  S  M  E  I  H  Q  A  L  T  R 1270                   1290                   1310
     GCTCAAGCATCATCCGCAACGTGCTACCACGTCACGAGCAGGGTGGTGTCTTCGCCGCTG
       S  S  I  I  R  N  V  L  P  R  H  E  Q  G  G  V  F  A  A  E 1330                   1350                   1370
     AGGGTTACGCACGCGCCACCGGCTTCCCCGGCGTTTGCATTGCCACCTCCGGCCCTGGCG
       G  Y  A  R  A  T  G  F  P  G  V  C  I  A  T  S  G  P  G  A 1390                   1410                   1430
     CCACCAATCTCGTCAGTGGCCTCGCGGACGCCCTACTGGATAGCGTCCCCATTGTTGCTA
       T  N  L  V  S  G  L  A  D  A  L  L  D  S  V  P  I  V  A  I 1450                   1470                   1490
     TAACCGGTCAAGTTGCACGTAGGATGATCGGTACTGATGCTTTTCAGGAAACTCCGATTG
       T  G  Q  V  A  R  R  M  I  G  T  D  A  F  Q  E  T  P  I  V 1510                   1530                   1550
     TTGAGGTAACTAGATCGATTACCAAGCATAATTATCTCGTTATGGACGTAGAGGATATTC
       E  V  T  R  S  I  T  K  H  N  Y  L  V  M  D  V  E  D  I  P 1570                   1590                   1610
     CTAGGGTTGTACGTGAGGCTTTTTTCCTTGCGAGATCGGGCCGGCCTGGCCTTGTTTTGA
       R  V  V  R  E  A  F  F  L  A  R  S  G  R  P  G  L  V  L  I 1630                   1650                   1670
     TTGATGTACCTAAGGATATTCAGCAACAATTGGTGATACCTGACTGGGATCAGCCAATGA
       D  V  P  K  D  I  Q  Q  Q  L  V  I  P  D  W  D  Q  P  M  R 1690                   1710                   1730
     GGTTGCCTGGTTACATGTCTAGGTTACCTAAATTGCCCAATGAGATGCTTTTAGAACAAA
       L  P  G  Y  M  S  R  L  P  K  L  P  N  E  M  L  L  E  Q  I
```

FIG. 4C

```
       1750                1770                1790
TTGTTAGGCTTATTTCTGAGTCAAAGAAGCCTGTTTTGTATGTGGGGGGTGGGTGTTCGC
 V  R  L  I  S  E  S  K  K  P  V  L  Y  V  G  G  G  C  S  Q 1810                1830                1850
AATCGAGTGAGGAGTTGAGACGATTCGTGGAGCTCACCGGTATCCCCGTGGCAAGTACTT
 S  S  E  E  L  R  R  F  V  E  L  T  G  I  P  V  A  S  T  L 1870                1890                1910
TGATGGGTCTTGGAGCTTTTCCAACTGGGGATGAGCTTTCCCTTTCAATGTTGGGTATGC
 M  G  L  G  A  F  P  T  G  D  E  L  S  L  S  M  L  G  M  H 1930                1950                1970
ATGGTACTGTTTATGCTAATTATGCTGTGGACAGTAGTGATTTATTGCTCGCATTTGGGG
 G  T  V  Y  A  N  Y  A  V  D  S  S  D  L  L  A  F  G  V 1990                2010                2030
TGAGGTTTGATGATAGAGTTACTGGAAAGTTAGAAGCTTTTGCTAGCCGAGCGAAAATTG
 R  F  D  D  R  V  T  G  K  L  E  A  F  A  S  R  A  K  I  V 2050                2070                2090
TTCACATTGATATTGATTCAGCTGAGATTGGAAAGAACAAGCAGCCTCATGTTTCCATTT
 H  I  D  I  D  S  A  E  I  G  K  N  K  Q  P  H  V  S  I  C 2110                2130                2150
GTGCGGATATCAAGTTGGCGTTACAGGGTTTGAATTCGATATTGGAGAGTAAGGAAGGTA
 A  D  I  K  L  A  L  Q  G  L  N  S  I  L  E  S  K  E  G  K 2170                2190                2210
AACTGAAGTTGGATTTTTCTGCTTGGAGGCAGGAGTTGACGGTGCAGAAAGTGAAGTACC
 L  K  L  D  F  S  A  W  R  Q  E  L  T  V  Q  K  V  K  Y  P 2230                2250                2270
CGTTGAATTTTAAAACTTTTGGTGATGCTATTCCTCCGCAATATGCTATCCAGGTTCTAG
 L  N  F  K  T  F  G  D  A  I  P  P  Q  Y  A  I  Q  V  L  D 2290                2310                2330
ATGAGTTAACTAATGGGAGTGCTATTATAAGTACCGGTGTTGGGCAGCACCAGATGTGGG
 E  L  T  N  G  S  A  I  I  S  T  G  V  G  Q  H  Q  M  W  A 2350                2370                2390
CTGCTCAATATTATAAGTACAGAAAGCCACGCCAATGGTTGACATCTGGTGGATTAGGAG
 A  Q  Y  Y  K  Y  R  K  P  R  Q  W  L  T  S  G  G  L  G  A 2410                2430                2450
CGATGGGATTTGGTTTGCCCGCTGCTATTGGTGCGGCTGTTGGAAGACCTGATGAAGTTG
 M  G  F  G  L  P  A  A  I  G  A  A  V  G  R  P  D  E  V  V 2470                2490                2510
TGGTTGACATTGATGGTGATGGCAGTTTCATCATGAATGTGCAGGAGCTAGCAACTATTA
 V  D  I  D  G  D  G  S  F  I  M  N  V  Q  E  L  A  T  I  K
```

FIG.4D

```
          2530              2550              2570
AGGTGGAGAATCTCCCAGTTAAGATTATGTTACTGAATAATCAACACTTGGGAATGGTGG
  V  E  N  L  P  V  K  I  M  L  L  N  N  Q  H  L  G  M  V  V 2590              2610              2630
TTCAATTGGAGGATCGGTTCTATAAGGCTAACAGAGCACACACATACCTGGGGAATCCTT
  Q  L  E  D  R  F  Y  K  A  N  R  A  H  T  Y  L  G  N  P  S 2650              2670              2690
CTAATGAGGCGGAGATCTTTCCTAATATGTTGAAATTTGCAGAGGCTTGTGGCGTACCTG
  N  E  A  E  I  F  P  N  M  L  K  F  A  E  A  C  G  V  P  A 2710              2730              2750
CTGCGAGAGTGACACACAGGGATGATCTTAGAGCGGCTATTCAAAAGATGTTAGACACTC
  A  R  V  T  H  R  D  D  L  R  A  A  I  Q  K  M  L  D  T  P 2770              2790              2810
CTGGGCCATACTTGTTGGATGTGATTGTACCTCATCAGGAACATGTTCTACCTATGATTC
  G  P  Y  L  L  D  V  I  V  P  H  Q  E  H  V  L  P  M  I  P 2830              2850              2870
CCAGTGGCGGGGCTTTCAAAGATGTGATCACAGAGGGTGACGGGAGAAGTTCCTATTGAC
  S  G  G  A  F  K  D  V  I  T  E  G  D  G  R  S  S  Y  *

2890              2910              2930
TTTGAGGTGCTACAGAGCTAGTTCTAGGCCTTGTATTATCTAAAATAAAC
```

FIG.5A

```
        10                  30                  50
GGATCCCTCTTTCATTTGTTCTCATCCATTTTTGCGATTCATGTGCATTTAATCAGTAGG 70                  90                 110
ACCCCTTTTTAGCTTAGTAGTGCTCTCATGTTCTAACTTAATATTAAACCAACCACACT 130                 150                 170
CCATCTGCATTACCCTCCTTCCAGTTTCGTCTCTCCCTGCCCTCCCCTTCAACAATGGCG
                                                          M  A 190                 210                 230
GCGGCGGCTCCATCTCCCTCTTCTTCCGCTTTCTCCAAAACCCTATCGCCTTCCTCCTCC
 A  A  A  P  S  P  S  S  S  A  F  S  K  T  L  S  P  S  S  S 250                 270                 290
ACATCCTCCACCCTCCTCCCTAGATCAACCTTCCCTTTCCCCCACCACCCCCACAAGACC
 T  S  S  T  L  L  P  R  S  T  F  P  F  P  H  H  P  H  K  T 310                 330                 350
ACCCCACCACCCCTCCACCTCACCCACACTCACATTCACATTCACAGCCAACGCCGTCGT
 T  P  P  P  L  H  L  T  H  T  H  I  H  I  H  S  Q  R  R  R 370                 390                 410
TTCACCATATCCAATGTCATTTCCACTAACCAAAAAGTTTCCCAGACCGAAAAAACCGAA
 F  T  I  S  N  V  I  S  T  N  Q  K  V  S  Q  T  E  K  T  E 430                 450                 470
ACTTTCGTTTCCCGTTTTGCTCCTGACGAACCCAGAAAGGGTTCCGACGTTCTCGTGGAG
 T  F  V  S  R  F  A  P  D  E  P  R  K  G  S  D  V  L  V  E 490                 510                 530
GCTCTCGAAAGAGAAGGGGTTACGGACGTCTTTGCGTACCCAGGTGGCGCTTCCATGGAG
 A  L  E  R  E  G  V  T  D  V  F  A  Y  P  G  G  A  S  M  E 550                 570                 590
ATTCACCAAGCTTTGACCCGTTCAAGCATCATCCGCAACGTGCTGCCACGTCACGAGCAG
 I  H  Q  A  L  T  R  S  S  I  I  R  N  V  L  P  R  H  E  Q 610                 630                 650
GGCGGTGTCTTCGCCGCTGAGGGTTACGCACGCGCCACCGGATTTCCCGGCGTTTGCATT
 G  G  V  F  A  A  E  G  Y  A  R  A  T  G  F  P  G  V  C  I 670                 690                 710
GCCACCTCTGGCCCCGGCGCCACCAATCTCGTCAGCGGCCTCGCTGACGCGCTACTGGAT
 A  T  S  G  P  G  A  T  N  L  V  S  G  L  A  D  A  L  L  D 730                 750                 770
AGCGTCCCCATTGTTGCTATAACAGGTCAAGTGCAACGTAGGATGATAGGTACTGATGCT
 S  V  P  I  V  A  I  T  G  Q  V  Q  R  R  M  I  G  T  D  A
```

FIG. 5B

```
         790               810               830
TTTCAGGAAACTCCTATTGTTGAGGTAACTAGATCGATTACCAAGCATAATTATCTCGTT
 F  Q  E  T  P  I  V  E  V  T  R  S  I  T  K  H  N  Y  L  V 850               870               890
ATGGACGTAGAGGATATTCCTAGGGTTGTACGTGAAGCTTTTTTCCTCGCGAGATCGGGC
 M  D  V  E  D  I  P  R  V  V  R  E  A  F  F  L  A  R  S  G 910               930               950
CGGCCTGGCCCTATTTTGATTGATGTACCTAAGGATATTCAGCAACAATTGGTGATACCT
 R  P  G  P  I  L  I  D  V  P  K  D  I  Q  Q  Q  L  V  I  P 970               990              1010
GACTGGGATCAGCCAATGAGGTTACCTGGTTACATGTCTAGGTTGCCTAAATTGCCCAAT
 D  W  D  Q  P  M  R  L  P  G  Y  M  S  R  L  P  K  L  P  N 1030              1050              1070
GAGATGCTTTTAGAACAAATTGTTAGGCTTATTTCTGAGTCAAAGAAGCCTGTTTTGTAT
 E  M  L  L  E  Q  I  V  R  L  I  S  E  S  K  K  P  V  L  Y 1090              1110              1130
GTGGGGGGTGGGTGTTCGCAATCGAGTGAGGACTTGAGACGATTCGTGGAGCTCACGGGT
 V  G  G  G  C  S  Q  S  S  E  D  L  R  R  F  V  E  L  T  G 1150              1170              1190
ATCCCCGTGGCAAGTACTTTGATGGGTCTTGGAGCTTTTCCAACTGGGGATGAGCTTTCC
 I  P  V  A  S  T  L  M  G  L  G  A  F  P  T  G  D  E  L  S 1210              1230              1250
CTTTCAATGTTGGGTATGCATGGTACTGTTTATGCTAATTATGCTGTGGACAGTAGTGAT
 L  S  M  L  G  M  H  G  T  V  Y  A  N  Y  A  V  D  S  S  D 1270              1290              1310
TTGTTGCTCGCATTTGGGGTGAGGTTTGATGATAGAGTTACTGGAAAGTTAGAAGCTTTT
 L  L  L  A  F  G  V  R  F  D  D  R  V  T  G  K  L  E  A  F 1330              1350              1370
GCTAGCCGAGCAAAAATTGTTCACATTGATATTGATTCAGCTGAGATTGGAAAGAACAAG
 A  S  R  A  K  I  V  H  I  D  I  D  S  A  E  I  G  K  N  K 1390              1410              1430
CAGCCTCATGTTTCCATTTGTGCAGATATCAAGTTGGCGTTACAGGGTTTGAATTCGATA
 Q  P  H  V  S  I  C  A  D  I  K  L  A  L  Q  G  L  N  S  I 1450              1470              1490
CTGGAGAGTAAGGAAGGTAAACTGAAGTTGGATTTTTCTGCTTGGAGGCAGGAGTTGACG
 L  E  S  K  E  G  K  L  K  L  D  F  S  A  W  R  Q  E  L  T 1510              1530              1550
GAGCAGAAAGTGAAGCACCCATTGAACTTTAAAACTTTTGGTGATGCAATTCCTCCGCAA
 E  Q  K  V  K  H  P  L  N  F  K  T  F  G  D  A  I  P  P  Q
```

FIG.5C

```
            1570                1590                1610
TATGCTATCCAGGTTCTAGATGAGTTAACTAATGGGAATGCTATTATAAGTACTGGTGTG
 Y  A  I  Q  V  L  D  E  L  T  N  G  N  A  I  I  S  T  G  V 1630                1650                1670
GGGCAACACCAGATGTGGGCTGCTCAATACTATAAGTACAGAAAGCCACGCCAATGGTTG
 G  Q  H  Q  M  W  A  A  Q  Y  Y  K  Y  R  K  P  R  Q  W  L 1690                1710                1730
ACATCTGGTGGATTAGGAGCAATGGGATTTGGTTTGCCCGCTGCTATTGGTGCGGCTGTT
 T  S  G  G  L  G  A  M  G  F  G  L  P  A  A  I  G  A  A  V 1750                1770                1790
GGAAGACCGGATGAAGTTGTGGTTGACATTGATGGTGATGGCAGTTTCATCATGAATGTG
 G  R  P  D  E  V  V  V  D  I  D  G  D  G  S  F  I  M  N  V 1810                1830                1850
CAGGAGCTTGCAACAATTAAGGTGGAGAATCTCCCAGTTAAGATTATGTTACTGAATAAT
 Q  E  L  A  T  I  K  V  E  N  L  P  V  K  I  M  L  L  N  N 1870                1890                1910
CAACACTTGGGAATGGTGGTTCAATGGGAGGATCGGTTCTATAAGGCTAACAGAGCACAC
 Q  H  L  G  M  V  V  Q  W  E  D  R  F  Y  K  A  N  R  A  H 1930                1950                1970
ACATACCTGGGGAATCCTTCTAATGAGGCGGAGATCTTTCCTAATATGCTGAAATTTGCA
 T  Y  L  G  N  P  S  N  E  A  E  I  F  P  N  M  L  K  F  A 1990                2010                2030
GAGGCTTGTGGCGTACCTGCTGCAAGAGTGACACATAGGGATGATCTTAGAGCTGCCATT
 E  A  C  G  V  P  A  A  R  V  T  H  R  D  D  L  R  A  A  I 2050                2070                2090
CAGAAGATGTTAGACACTCCTGGGCCATACTTGTTGGATGTGATTGTACCTCATCAGGAA
 Q  K  M  L  D  T  P  G  P  Y  L  L  D  V  I  V  P  H  Q  E 2110                2130                2150
CATGTTTTACCTATGATTCCCAGTGGCGGAGCTTTCAAAGATGTGATCACAGAGGGTGAC
 H  V  L  P  M  I  P  S  G  G  A  F  K  D  V  I  T  E  G  D 2170                2190                2210
GGGAGAAGTTCCTATTGAGTTTGAGAAGCTACAGAGCTAGTTCTAGGCCTTGTATTATCT
 G  R  S  S  Y  *

2230                2250                2270
AAAATAAACTTCTATTAAGCCAAACATGTTCTGTCTATTAGTTTGTTGTTAGTTTTTGCT 2290                2310                2330
GTGGCTTTGCTCGTTGTCACTGTTGTACTATTAAGTAGTTGATATTTATGTTTGCTTTAA
```

FIG.5D

```
        2350                2370                2390
GTTTTGCATCATCTCCCTTTGGTTTTGAATGTGAAGGATTTCAGCAAAGTTTCATTCTCT 2410                2430                2450
GTTTGCAACATCCACTTGGTATCTGGAGATTAATTTCTAGTGGAGTAGTTTAGTGCGATA 2470                2490                2510
AAATTAGCTTGTTCCACATTTTTATTTCGTAAGCTATGTTAGGCTGGGTCAGATTGGAAC
```

FIG. 6A

```
              10              20          30              40              50
A.  MAAAAAAAPSPS....FSKTLSSSSSKSSTLLPRSTFPFPHHPHKTPPPLHLTPT..HIH
    ||||    |||     ||||| ||| ||||||||||||||||||||||||||| |||
B.  MAAAA..PSPSSS.AFSKTLSPSSTSSTLLPRSTFPFPHHPHKTPPPLHLTHTHIHIH
    ||||    |||    |||||  ||   |||||    |
C.  MAAATTTTTTSSSISFSTKPSPSSSKSPLPISRFSLNPNKSSSSSRRRGIKSSSPS
                                                   |
D.                          MIRQSTLKNFAIKRCFQHIAYRNTPAMRSVALAQRFYSSSSRYYSASPLPASKRP 70              80          90              100             110
A.  SQRRRFTISNVISTTQKVSETQKAETFVSRFAPDEPRKGSDVLVEALEREGVTDVFAYPG
    ||||||||||||| |||||| |||||||||||||||||||||||||||||||||||||
B.  SQRRRFTISNVISTNQKVSQTEKTETFVSRFAPDEPRKGSDVLVEALEREGVTDVFAYPG
      |     |      |      |      ||  |||  |    ||||| ||||||||||
C.  SISAVLNTTTNVTTPSPTKPETFISRFAPDQPRKGADILVEALERQGVETVFAYPG
           |          ||  |    |         |     |   ||  |||||
D.  EPAPSFNVDPLEQPAEPSKLAKKLRAEPDMDTSFVGLTGGQIFNEMMSRQNVDTVFGYPG
                                        |       ||  |  || ||||
E.                      MASSGTTSTRKRFETGAEFIVHFLEQQGIKIVTGIPG
                                        |  |        |   ||||
F.                              MNGAQWVVHALRAQGVNTVFGYPG
                                        |            ||||
G.                              MEMLSGAEMVVRSLIDQGVKQVFGYPG
```

```
119        122 ε₁
 ─── ε₂ ───
Sub-sequence A
```

FIG. 6B

```
             130                    150                    170
A. GASMEIIHQALTRSSIIRNVLPRHEQGGVFAAEGYARATGFPGVCIATSGPGATNLVSGLA
B. GASMEIIHQALTRSSIIRNVLPRHEQGGVFAAEGYARATGFPGVCIATSGPGATNLVSGLA
C. GASMEIHQALTRSSIRNVLPRHEQGGVFAAEGYARSSGKPGICIATSGPGATNLVSGLA
D. GAILPVYDAIINSDKFNFVLPKHEQGAGHMAEGYARASGKPGVVLTSGPGATNVVTPMA
E. GSILPVYDALSQSTQIRHILARHEQGAGFIAQGMARTDGKPAVCMACSGPGATNLITGLA
F. GAIMPVYDAL.YDGGVEHLLCRHEQGAAMAAIGYARATGKTGVCIATSGPGATNLITGLA
G. GAVLDIYDALHTVGGIDHVLVRHEQAAVHMADGLARATGEVGVVLVTSGPGATNAITGIA 190                    210                    230
A. DALLDSVPIVAITGQVPRRMIGTDAFQETPIVEVTRSITKHNYLVMDVEDIPRVVREAFF
B. DALLDSVPIVAITGQVPRRMIGTDAFQETPIVEVTRSITKHNYLVMDVEDIPRVVREAFF
C. DALLDSVPLVAITGQVPRRMIGTDAFQETPIVEVTRSITKHNYLVMDVEDIPRIIEEAFF
D. DAFADGIPMVVFTGQVPTSAIGTDAFQEADVVGISRSCTKWNVMVKSVEELPLRINEAFE
E. DARLDSIPLICITGQVPASMIGTDAFQEVDTYGISIPITKHNYLVRHIEELPQVMSDAFR
F. DALLDSIPVVAITGQVSAPFIGTDAFQEVDVLGLSLACTKHSFLVQSLEELPRIMAEAFD
G. TAYMDSIPLVVLSGQVATSLIGYDAFQECDMVGISRPVVKIISFLVKQTEDIPQVLKKAFW
```

194    197  
       $a_1$  
Sub-sequence B

201      $b_2$    208  
Sub-sequence C

FIG. 6C

```
        250                          270                         290
A. LARSGRPGPVLIDVPKDIQQQLVIPDWDQPMR.....LPGYMSRLPKLPNEMLLEQIVRL
B. LARSGRPGPILIDVPKDIQQQLVIPDWDQPMR.....LPGYMSRLPKLPNEMLLEQIVRL
C. LATSGRPGPVLVDVPKDIQQQLAIPNWEQAMR.....LPGYMSRMPKPPEDSHLEQIVRL
D. IATSGRPGPVLVDLPKDVTAAILRNPIPTKTTLPSNALNQLTSRAQDEFVMQSINKAADL
E. IAQSGRPGPVWIDIPKDVQTAVFEIETQ..........PAMAEKAAAPAFSEESIRDAAAM
F. VACSGRPGPVLVDIPKDIQLASGDLE............PWFTTVENEVTFPHAEVEQARQM
G. LAASGRPGPVVVDLPKDILNPANKLPYVWPES......VSMRSYNPTTTGHKGQIKRALQS 310                          330                          350
A. ISESKKPVLYVGGGCSQSSEELRRFVEL...TGIPVASTLMGLGAFPTGDELSLSMLGMH
B. ISESKKPVLYVGGGCSQSSEDLRRFVEL...TGIPVASTLMGLGAFPTGDELSLSMLGMH
C. ISESKKPVLYVGGGCLNSSDELGRFVEL...TGIPVASTLMGLGSYPCDDELSLHMLGMH
D. INLAKKPVLYVGAGILNHADGPRLLKELSDRAQIPVTTLQGLGSFDQEDPKSLDMLGMH
E. INAAKRPVLYLGGG...VINAPARVRELAEKAQLPTTMTLMALGMLPKAHPLSLGMLGMH
F. LAKAQKPMLYVGGG.VGMAQAVPALREFLAATKMPATCTLKGLGAVEADYPYYLGMLGMH
G. VVAVKKPVVYVGGG.AITAGCHQQLKETVEALNLPVVCSLMGLGAFPATHRQVLGMLGMH
```

255  257
—λ₁—
—— Sub-sequence D ——

356            361
—— σ₁ ——
—— Sub-sequence G ——

FIG. 6D

```
           370                       390                           410
A.  GTVYANYAVDSSDLLLAFGVRFDDRVTGKLEAFASRAKIVHIDIDSAEIGKNKQPHVSIC
    ||||||||||||||||||||||||||||||||||||||||||||||||||||||||||
B.  GTVYANYAVDSSDLLLAFGVRFDDRVTGKLEAFASRAKIVHIDIDSAEIGKNKQPHVSIC
    ||||||||| |||||||||||||||||||||||||||||||||||||||||||||| |
C.  GTVYANYAVEHSDLLLAFGVRFDDRVTGKLEAFASRAKIVIIIDIDSAEIGKNKTPHVSVC
     |||| |   | |||||  ||| |||||||  |  |    |  | ||   | || ||  |
D.  GCATANLAVQNADLIIAVGAREDDRVTGNISKFAPEARRAAAEGRGGIIHFEVSPKNINK
     | | |  |   |||| | ||| |||||  |       |       ||  | |  |
E.  GVRSTNYILQEADLLIVLGAREDDRAIGKTEQFCPNAKIIIVDIDRAQLGKIKQPHVAIQ
     | | |  |    |||  |||| ||  |  |    |     |||  | | ||||| |
F.  GTKAANFAVQECDLLIAVGAREDDRVTGKLNTFAPHASVIIMDIDPAEMNKLRQAHVALQ
     | | |   |   ||   ||| ||||  |  |    |   |||    |  |  | |
G.  GTYEANMTMHINADVIFAVGVREDDRTTNNLAKYCPNATVLHIIDPTSISKTVTADIPIV 430                       450                           470
A.  ADIKLALQGLNSILESKEGKLKLDFSAWRQELTVQKVKYPLNFKTF...........GDAIP
    ||||||||||||||||||||||||||||||||| |||||||||||           |||||
B.  ADIKLALQGLNSILESKEGKLKLDFSAWRQELTEQKVKHPLNFKTF...........GDAIP
      | ||| |  |||  |  ||| ||| |||| |||  | |    |             ||||
C.  GDVKLALQGMNKVLENRAEELKLDFGVWRNELNVQKQKFPLSEKTF...........GEAIP
        | | | |   | |   |  |  |  |   |        |  |             | |
D.  VVQTQIAVEGDATTNLGKMMSKIFPVKERSEWFAQINKWKKEYPYAYMEETPGSKIKPQT
      |     |   |                     |  |  |
E.  ADVDDVLAQLIPLVEAQPRAEWHQLVADLQREFPCPIPKA..............CDPLS
        |  ||   |           |  |
F.  GDLNALLPALQQPLNQYDWQQHCAQLRDEHSWRYDHP.................GDAIY
      |    |  |                                              ||
G.  GDARQVLEQMLELLSQESAHQPLDEIRDWWQQIEQWRARQCLKYDTH.......SEKIK
```

381 — γ₁ — 385
—— Sub-sequence E ——

FIG. 6E

```
              490                  510                     530
A.   PQYAIQVLDELTNGSAIISTGVGQHQMWAAQYYKYRKPRQWLTSGGLGAMGFGLPAAIGA
     |||||||||||| |||||  |||||||||||||||||||||||||||||||||||||||
B.   PQYAIQVLDELTNGNAIISTGVGQHQMWAAQYYKYRKPRQWLTSGGLGAMGFGLPAAIGA
     |||||  ||||| |  ||||  ||||||||||||| || |||||||||||||||||| |
C.   PQYAIKVLDELTDGKAIISTGVGQHQMWAAQFYNYKKPRQWLSSGGLGAMGFGLPAAIGA
     |  ||  |||  ||   |   || |||||||    |  ||  | || ||| |||||| |
D.   VIKKLSKVANDTGRHVIVTTGVGQHQMWAAQHWTWRNPHTFITSGGLGTMGYGLPAAIGA
     |  |   |  |    |  ||||| |||||| |   |    ||||||| || |||| |||
E.   HYGLINAVAACVDDNAIITTDVGQHQMWTAQAYPLNRPRQWLTSGGLTMGFGLPAAIGA
           |   |     |  |   |  ||| |   || | | || ||  || |||| |||
F.   APLLLKQLSDRKPADCVVTTDVGQHQMWAAQHIAHTRPENFITSSGLGTMGFGLPAAVGA
        |   ||     |  |   ||| ||||   |  | |  || |||  || ||||| |
G.   PQAVIETLWRLTKGDAYVTSDVGQHQMFAALYYPFDKPRRWINSGGLGSMGFGLPAALGV 550                  570                     590
A.   AVGRPDEVVVDIDGDGSFIMNVQELATIKVENLPVKIMLLNNQHLGMVVQWEDRFYKANR
     |||||||||||||||||||||||||||||||||||||||||||||||||||||||||||
B.   AVGRPDEVVVDIDGDGSFIMNVQELATIKVENLPVKIMLLNNQHLGMVVQWEDRFYKANR
      |   |   | |||||||| |||||| |||||||||| ||||| |||| |||||||||
C.   SVANPDAIVVDIDGDGSFIMNVQELATIRVENLPVKVLLLNNQIILGMVMQWEDRFYKANR
       | |   |  |||||  |    |     |      ||  |||  |||  |   |
D.   QVAKPESLVIDIDGDASFNMTLTELSSAVQAGTPVKILILNNEEQGMVTQWQSLFYEHRY
      | |      |  |      |  |      |  ||  |||||  |||| |  | |
E.   ALANPDRKVLCFSGDGSLMMNIQEMATASENQLDVKIILMNNEALGLVHQQQSLFYEQGA
                  |  ||    |      |    ||  |  |   |  |   |  |
F.   QVARPNDTVVCISGDGSFMMNVQELGTVKRKQLPLKIVLLDNQRLGMVRQWQQLFFQERY
                   |||||  |    |   |    | |  | |  ||| | |  |
G.   KMALPEETVVCVTGDGSIQMNIQELSTALQYELPVLVVNLNNRYLGMVKQWQDMIYSGRH

β₇
                                      β₈    β₃      595
                                   586                 
                                   Sub-sequence F
```

FIG.6F

```
                   610                   630                   650
A.  AHTYLGNPSNEAEIFPNMLKFAEACGVPAARVTHRDDLRAAIQKMLDTPGPYLLDVIVPHQEHVL
    ||||||||||||||||||||||||||||||||||||||||||||||||||||||||||||||||
B.  AHTYLGNPSNEAEIFPNMLKFAEACGVPAARVTHRDDLRAAIQKMLDTPGPYLLDVIVPHQEHVL
    ||| || ||||||||||| | ||||  ||||||||||||||||||||||| ||||||||||||
C.  AHTFLGDPAQEDEIFPNMLLFAAACGIPAARVTKKADLREAIQTMLDTPGPYLLDVICPHQEHVL
         ||  |       ||  |  ||   | |||  ||| ||| ||| ||||| | |||| |
D.  SHTHQL........NPDFIKLAEAMGLKGLRVKKQEELDAKLKEFVSTKGPVLLEVEVDKKVPVL
          |        | |  |||  |    ||   ||  |  |   ||| | |   |    |
E.  FVATYP........GKINFMQIAAGFGLETCDLNNEADPQASLQEIINRPGPALIHVRIDAEEKVY
        |          |  |  ||    |    |       |  ||  | ||  ||   |   |
F.  SETTLT........DNPDFLMLASAFGIHGQHITRKDQVEAALDTMLNSDGPYLLHVSIDELENVW
        |         |  |  ||||   |  |  |   | | || || || || ||  |    |
G.  SQSYMQ.....SLPDFVRRGAYGHVGIQISHPHGWKANLARRWNRCAIIAWCLLMLPSMAASTST 670                   690
A.  PMIPSGGAFKDVITEGDGRSSY
    ||||||||||||||||||||||
B.  PMIPSGGAFKDVITEGDGRSSY
    ||||||| ||||||||||||||
C.  PMIPSGGTFNDVITEGDGRIKY
    |||   |  ||      |
D.  PMVAGGSGLDEFINFDPEVERQQTELRHKRTGGKH
    ||
E.  PMVPPGAANTEMVGE
    | |||||
F.  PLVPPGASNSEMLEKLS
        ||
G.  RCRFAGAEWMKCG
```

FIG. 8A

```
                      30                        60                                              90
A. MAAAA..PSPSSS.AFSKTLSPSSSTSSTLLPRSTFPFPHHPHKTPPPLHLTHTHIHIHSQRRRFTISNVISTNQKVSQTEKTETFVSR
    |||| ||||||  ||||||  ||| ||| |||||||||||||| ||||||| | |||||||||||||||||||  ||  |||||
B. MAAAAAAPSPS....FSKTLSSSSSKSSTLLPRSTFPFPHHPHKTPPPLHLTPT..HIHSQRRRFTISNVIST......TQKAETFVSR
    |||        ||||| |||   ||||| ||  |||     |      |      ||||||||||||||||
C. MAAATTTTTTSSISFSTKPSPSSSKSPLPISRFSLPFSLNPNKSSSSSRRRGIKSSSPSSISAVLNTTNVTTPSPTKPTKPETFISR
    |||          ||  |||    |          |
D. MAATFTNPTFSPSSTPLTKTLKSQSSISSTLPFSTPP.........KTPTPLFHRPLQISSSQSHKSSAIKTQTAPSSPAIEDSSFVSR 120                       150                                             180
A. FAPDEPRKGSDVLVEALEREGVTDVFAYPGGASMEIHQALTRSSIIRNVLPRHEQGGVFAAAEGYARATGFPGVCIATSGPGATNLVSGLA
   ||||||||||||||||||||||||||||||||||||||||||||||||||||||||||||||||||||||||||||||||||||||||
B. FAPDEPRKGSDVLVEALEREGRTDVFAYPGGASMEIHQALTRSSIIRNVLPRHEQGGVFAAAEGYARATGFPGVCIATSGPGATNLVSGLA
   ||||  ||||||||||||||| ||||||||||||||||||||||||||||||||||||||||||||||||| ||||||||||||||||
C. FAPDQPRKGADILVEALEREGQVETVFAYPGGASMEIHQALTRSSIRNVLPRHEQGGVFAAAEGYARSSGKPGICIATSGPGATNLVSGLA
    || |||||  ||||||||||  |||||||||||||||||||||||||||||||||||||||||| |      |||||||||||||||
D. FGPDEPRKGSDVLVEALEREGVTNVFAYPGGASMEIHQALTRSKTIRNVLPRHEQGGVFAAAEGYARATGKVGVCIATSGPGATNLVSGLA 210                       240                                             270
A. DALLDSVPIVAITGQVPRRMIGTDAFQETPIVEVTRSITKHNYLVMDVEDIPRVVREAFFLARSGRPGPILIDVPKDIQQQLVIPDWDQP
   ||||||||||||||||||||||||||||||||||||||||||||||||||||||||||||||||||||| ||||||||||||||||
B. DALLDSVPIVAITGQVPRRMIGTDAFQETPIVEVTRSITKHNYLVMDVEDIPRVVREAFFLARSGRPGLVLIDVPKDIQQQLVIPDWDQP
   |||||||||||||||||||||||||||||||||||||||||||||||||||||||||||| ||||||   |||||||||||||| |
C. DALLDSVPIVAITGQVPRRMIGTDAFQETPIVEVTRSITKHNYLVMDVEDIPRIIEEAFFLATSGRPGPVLVDVPKDIQQQLAIPNWEQA
   |||||||||||||||||||||||||||||||||||||||||||| |||||||| ||||||| ||||| |||||||||||| |  | |
D. DALLDSVPLVAITGQVPRRMIGTDAFQETPIVEVTRSITKHNYLVLDVEDIPRIVKEAFFLANSGRPGPVLIDLPKDIQQQLVVPDWDRP
```

FIG. 8B

```
                                 300                         330                              360
A.  MRLPGYMSRLPK....LPNEMLLEQIVRLISESKKPVLYVGGGCSQSSEDLRRFVELTGIPVASTLMGLGAFPTGDELSLSMLGMHGTVY
    |||||||||||    |||||||||||||||||||||||||||||||||||||||||||||||||||||||||||||||||||||||||
B.  MRLPGYMSRLPK....LPNEMLLEQIVRLISESKKPVLYVGGGCSQSQSSEELRRFVELTGIPVASTLMGLGAFPTGDELSLSMLGMHGTVY
    |||||||||||    ||| ||||||||||||||||||||||||| |  ||||||||||||||||||||||||| |||||||||||||||
C.  MRLPGYMSRMPK....PPEDSHLEQIVRLISESKKPVLYVGGGCLNSSDELGRFVELTGIPVASTLMGLGSYPCDDELSLHMLGMHGTVY
    |||||||||  |    ||  |||||||||||||||||||||||  || || |||||||||||||||| ||  |||||  |||||||||
D.  FKLGGYMSRLPKSKFSTNEVGLLEQIVRLMSESKKPVLYVGGGCLNSSEELRRFVELTGIPVASTLMGLGSYPCNDELSLHMLGMHGTVY 390                         420                              450
A.  ANYAVDSSSDLLLAFGVRFDDRVTGKLEAFASRAKIVHIDIDSAEIGKNKQPHVSICADIKLALQGLNSILESKEGKLKLDFSAWRQELTE
    ||||||||||||||||||||||||||||||||||||||||||||||||||||||||||||||||||||||||||||||||||| ||||
B.  ANYAVDSSSDLLLAFGVRFDDRVTGKLEAFASRAKIVHIDIDSAEIGKNKQPHVSICADIKLALQGLNSILESKEGKLKLDFSAWTQELTV
    |||||| ||||||||||||||||||||||||||||||||||||||||||||||||||||||||||||||||||||||||||||   |
C.  ANYAVEHSDLLLAFGVRFDDRVTGKLEAFASRAKIVHIDIDSAEIGKNKTPHVSVCGDVKLALQGMNKVLENRAEELKLDFGVWRNELNV
    ||||||  |||||||||||||||||||||||||||||||||||||||| ||||  | ||||||| | |||   |||||||  |   |
D.  ANYAVDKADLLLAFGVRFDDRVTGKLEAFASRAKIVHIDIDSAEIGKNKQPHVSICADVKLALRGMNKILESRIGKLNLDFSKWREELGE 480                         510                              540
A.  QKVKHPLNFKTFGDAIPPQYAIQVLDELTNGNAIISTGVGQHQMWAAQYYKYRKPRQWLTSGGLGAMGFGLPAAIGAAVGRPDEVVVDID
    |||| |||||||||||||||||||||||||||||||||||||||||||||| |||||||||||||||||||||||| |||||||||||
B.  QKVNDPLNFKTFGDAIPPQYAIQVLDELTNGSAIIITGVGQHQIWAAQYYKYRKPRQWLTSGGLGAMGFGLFAAIGAAVGRPDEVVVDID
    |||  ||||||||||||||||||||||||| |||  ||||||| ||||||||||||||||||||||||||| |||||||||||||||
C.  QKQKFPLSFKTFGEAIPPQYAIKVLDELTDGKAIISTGVGQHQMWAAQFYNYKKPRQWLSSGGLGAMGFGLPAAIGASVANPDAIVVDID
    ||   ||||||| ||||||||||||||| | ||||||||||||||||| | | ||||||||||||||||||||||| || ||| ||||
D.  QKKEFPLSFKTFGDAIPPQYAIQVLDELTNGNAIISTGVGQHQMWAAQHYKYRNPRQWLTSGGLGAMGFGLPAAIGAAVARPDAVVVDID
                                                                                          |||
E.  IQPQYAIQVLDELTKGEAIIGTGVGQHQMWAAQYYTKRPRQWLSSAGLGAMGFGLPAAAGASVANPGVTVVDID
```

FIG. 8C

```
                   570                           600                           630
A. GDGSFIMNVQELATIKVENLPVKIMLLNNQHLGMVVQWEDRFYKANRAHTYLGNPSNEAEIFPNMLKFAEACGVPAARVTHRDDLRAAIQ
   |||||||||||||||||||||||||||||||||||||||||||||||||||||||||||||||||||||||||||||||||||||||
B. GDGSFIMNVQELATIKVENLPVKIMLLNNQHLGMVVQWEDRFYKANRAHTYLGNRSNEAEIFPNMLKFGEACGVPAARVTHRDDLRAAIQ
   ||||||||||||||| ||||||||||| |||||||||||||||||||||||||| |||||||||||| ||||||||||||||||||||
C. GDGSFIMNVQELATIRVENLPVKVLLLNNQHLGMVMQWEDRFYKANRAHTFLGDPAQEDEIFPNMLLFAAACGIPAARVTKKADLREAIQ
   |||||||||||||| |||||||| |||||||||| |||||||||||||  ||   ||| ||||| || |||| ||||||| || ||||
D. GDGSFIMNVQELATIRVENLPVKIMLLNNQHLGMVVQWEDRFYKANRAHTYLGNPSKSADIFPDMLKFAEACDIPSARVSNVADLRAAIQ
   |||||||||||||| ||||||||| ||||||||||||||||||||||||||||| | ||||| ||| |||| || |||| |  |||||
E. GDGSFLMNVQELAMIRIENLPVKVFVLNNQHLGMVVQWEDRFYKANRAHTYLGNPENESEIYPDFVTIAKGFNIPAVRVTKKNEVRAAIK
   ||||| ||||||| || ||||||  |||||||||||||||||||||||||||||| |  ||| |  |  || |  |||||| |||||

660
A. KMLDTPGPYLLDVIVPHQEHVLPMIPSGGAFKDVITEGDGRSSY
   |||||||||||||||||||||||||||||||||||||||||||
B. KMLDTPGPYLLDVIVPHQEHVLPMIPSGGAFKDVITEGDGRSSY
   ||||||||||||| |||||||||||||||||||||||||||
C. TMLDTPGPYLLDVICPHQEHVLPMIPSGGTFNDVITEGDGRIKY
   |||||||||||||  |||||||||||||| | ||||||||  |
D. TMLDTPGPYLLDVIVPHQEHVLPMIPSGAGFKDTITEGDGRTSY
   ||||||||||||||||||||||||||| |||| ||||||| ||
E. KMLETPGPYLLDIIVPHQEHVLPMIPSGGAFKDMILDGDGRTVY
```

FIG. 10A

```
         10                    30                    50
GCTCTTAGTTTTGTTATTGTTTTTGTAGCCAAATTCTCCATTCTTATTCCATTTTCACTT 70                    90                   110
ATCTCTTGTTCCTTATAGACCTTATAAGTTTTTTATTCATGTATACAAATTATATTGTCA 130                   150                   170
TCAAGAAGTATCTTTAAAATCTAAATCTCAAATCACCAGGACTATGTTTTTGTCCAATTC 190                   210                   230
GTGGAACCAACTTGCAGCTTGTATCCATTCTCTTAACCAATAAAAAAAGAAAGAAAGATC 250                   270                   290
AATTTGATAAATTTCTCAGCCACAAATTCTACATTTAGGTTTTAGCATATCGAAGGCTCA 310                   330                   350
ATCACAAATACAATAGATAGACTAGAGATTCCAGCGTCACGTGAGTTTTATCTATAAATA 370                   390                   410
AAGGACCAAAAATCAAATCCCGAGGGCATTTTCGTAATCCAACATAAAACCCTTAAACTT 430                   450                   470
CAAGTCTCATTTTTAAACAAATCATGTTCACAAGTCTCTTCTTCTTCTCTGTTTCTCTAT 490                   510                   530
CTCTTGCTCATCTTTCTCCTGAACCATGGCGGCGGCAACAACAACAACAACAACATCTTC
                                M  A  A  A  T  T  T  T  T  S  S 550                   570                   590
TTCGATCTCCTTCTCCACCAAACCATCTCCTTCCTCCTCCAAATCACCATTACCAATCTC
 S  I  S  F  S  T  K  P  S  P  S  S  S  K  S  P  L  P  I  S 610                   630                   650
CAGATTCTCCCTCCCATTCTCCCTAAACCCCAACAAATCATCCTCCTCCTCCCGCCGCCG
 R  F  S  L  P  F  S  L  N  P  N  K  S  S  S  S  R  R  R 670                   690                   710
CGGTATCAAATCCAGCTCTCCCTCCTCCATCTCCGCCGTGCTCAACACAACCACCAATGT
 G  I  K  S  S  S  P  S  S  I  S  A  V  L  N  T  T  T  N  V 730                   750                   770
CACAACCACTCCCTCTCCAACCAAACCTACCAAACCCGAAACATTCATCTCCCGATTCGC
 T  T  T  P  S  P  T  K  P  T  K  P  E  T  F  I  S  R  F  A 790                   810                   830
TCCAGATCAACCCCGCAAAGGCGCTGATATCCTCGTCGAAGCTTTAGAACGTCAAGGCGT
 P  D  Q  P  R  K  G  A  D  I  L  V  E  A  L  E  R  Q  G  V 850                   870                   890
AGAAACCGTATTCGCTTACCCTGGAGGTGCATCAATGGAGATTCACCAAGCCTTAACCCG
 E  T  V  F  A  Y  P  G  G  A  S  M  E  I  H  Q  A  L  T  R
```

FIG.10B

```
          910                 930                 950
CTCTTCCTCAATCCGTAACGTCCTTCCTCGTCACGAACAAGGAGGTGTATTCGCAGCAGA
 S  S  S  I  R  N  V  L  P  R  H  E  Q  G  G  V  F  A  A  E 970                 990                 1010
AGGATACGCTCGATCCTCAGGTAAACCAGGTATCTGTATAGCCACTTCAGGTCCCGGAGC
 G  Y  A  R  S  S  G  K  P  G  I  C  I  A  T  S  G  P  G  A 1030                1050                1070
TACAAATCTCGTTAGCGGATTAGCCGATGCGTTGTTAGATAGTGTTCCTCTTGTAGCAAT
 T  N  L  V  S  G  L  A  D  A  L  L  D  S  V  P  L  V  A  I 1090                1110                1130
CACAGGACAAGTCTCTCGTCGTATGATTGGTACAGATGCGTTTCAAGAGACTCCGATTGT
 T  G  Q  V  S  R  R  M  I  G  T  D  A  F  Q  E  T  P  I  V 1150                1170                1190
TGAGGTAACGCGTTCGATTACGAAGCATAACTATCTTGTGATGGATGTTGAAGATATCCC
 E  V  T  R  S  I  T  K  H  N  Y  L  V  M  D  V  E  D  I  P 1210                1230                1250
TAGGATTATTGAGGAAGCTTTCTTTTTAGCTACTTCTGGTAGACCTGGACCTGTTTTGGT
 R  I  I  E  E  A  F  F  L  A  T  S  G  R  P  G  P  V  L  V 1270                1290                1310
TGATGTTCCTAAAGATATTCAACAACAGCTTGCGATTCCTAATTGGGAACAGGCTATGAG
 D  V  P  K  D  I  Q  Q  Q  L  A  I  P  N  W  E  Q  A  M  R 1330                1350                1370
ATTACCTGGTTATATGTCTAGGATGCCTAAACCTCCGGAAGATTCTCATTTGGAGCAGAT
 L  P  G  Y  M  S  R  M  P  K  P  P  E  D  S  H  L  E  Q  I 1390                1410                1430
TGTTAGGTTGATTTCTGAGTCTAAGAAGCCTGTGTTGTATGTTGGTGGTGGTTGTTTGAA
 V  R  L  I  S  E  S  K  K  P  V  L  Y  V  G  G  G  C  L  N 1450                1470                1490
TTCTAGCGATGAATTGGGTAGGTTTGTTGAGCTTACGGGGATCCCTGTTGCGAGTACGTT
 S  S  D  E  L  G  R  F  V  E  L  T  G  I  P  V  A  S  T  L 1510                1530                1550
GATGGGGCTGGGATCTTATCCTTGTGATGATGAGTTGTCGTTACATATGCTTGGAATGCA
 M  G  L  G  S  Y  P  C  D  D  E  L  S  L  H  M  L  G  M  H 1570                1590                1610
TGGGACTGTGTATGCAAATTACGCTGTGGAGCATAGTGATTTGTTGTTGGCGTTTGGGGT
 G  T  V  Y  A  N  Y  A  V  E  H  S  D  L  L  L  A  F  G  V 1630                1650                1670
AAGGTTTGATGATCGTGTCACGGGTAAGCTTGAGGCTTTTGCTAGTAGGGCTAAGATTGT
 R  F  D  D  R  V  T  G  K  L  E  A  F  A  S  R  A  K  I  V
```

FIG.10C

```
     1690                1710                1730
TCATATTGATATTGACTCGGCTGAGATTGGGAAGAATAAGACTCCTCATGTGTCTGTGTG
 H  I  D  I  D  S  A  E  I  G  K  N  K  T  P  H  V  S  V  C 1750                1770                1790
TGGTGATGTTAAGCTGGCTTTGCAAGGGATGAATAAGGTTCTTGAGAACCGAGCGGAGGA
 G  D  V  K  L  A  L  Q  G  M  N  K  V  L  E  N  R  A  E  E 1810                1830                1850
GCTTAAGCTTGATTTTGGAGTTTGGAGGAATGAGTTGAACGTACAGAAACAGAAGTTTCC
 L  K  L  D  F  G  V  W  R  N  E  L  N  V  Q  K  Q  K  F  P 1870                1890                1910
GTTGAGCTTTAAGACGTTTGGGGAAGCTATTCCTCCACAGTATGCGATTAAGGTCCTTGA
 L  S  F  K  T  F  G  E  A  I  P  P  Q  Y  A  I  K  V  L  D 1930                1950                1970
TGAGTTGACTGATGGAAAAGCCATAATAAGTACTGGTGTCGGGCAACATCAAATGTGGGC
 E  L  T  D  G  K  A  I  I  S  T  G  V  G  Q  H  Q  M  W  A 1990                2010                2030
GGCGCAGTTCTACAATTACAAGAAACCAAGGCAGTGGCTATCATCAGGAGGCCTTGGAGC
 A  Q  F  Y  N  Y  K  K  P  R  Q  W  L  S  S  G  G  L  G  A 2050                2070                2090
TATGGGATTTGGACTTCCTGCTGCGATTGGAGCGTCTGTTGCTAACCCTGATGCGATAGT
 M  G  F  G  L  P  A  A  I  G  A  S  V  A  N  P  D  A  I  V 2110                2130                2150
TGTGGATATTGACGGAGATGGAAGCTTTATAATGAATGTGCAAGAGCTAGCCACTATTCG
 V  D  I  D  G  D  G  S  F  I  M  N  V  Q  E  L  A  T  I  R 2170                2190                2210
TGTAGAGAATCTTCCAGTGAAGGTACTTTTATTAAACAACCAGCATCTTGGCATGGTTAT
 V  E  N  L  P  V  K  V  L  L  N  N  Q  H  L  G  M  V  M 2230                2250                2270
GCAATGGGAAGATCGGTTCTACAAAGCTAACCGAGCTCACACATTTCTCGGGGATCCGGC
 Q  W  E  D  R  F  Y  K  A  N  R  A  H  T  F  L  G  D  P  A 2290                2310                2330
TCAGGAGGACGAGATATTCCCGAACATGTTGCTGTTTGCAGCAGCTTGCGGGATTCCAGC
 Q  E  D  E  I  F  P  N  M  L  L  F  A  A  A  C  G  I  P  A 2350                2370                2390
GGCGAGGGTGACAAAGAAAGCAGATCTCCGAGAAGCTATTCAGACAATGCTGGATACACC
 A  R  V  T  K  K  A  D  L  R  E  A  I  Q  T  M  L  D  T  P 2410                2430                2450
AGGACCTTACCTGTTGGATGTGATTTGTCCGCACCAAGAACATGTGTTGCCGATGATCCC
 G  P  Y  L  L  D  V  I  C  P  H  Q  E  H  V  L  P  M  I  P
```

FIG. 10D

```
         2470                2490                2510
GAGTGGTGGCACTTTCAACGATGTCATAACGGAAGGAGATGGCCGGATTAAATACTGAGA
  S   G   G   T   F   N   D   V   I   T   E   G   D   R   I   K   Y   *

2530                2550                2570
GATGAAACCGGTGATTATCAGAACCTTTTATGGTCTTTGTATGCATATGGTAAAAAAACT 2590                2610                2630
TAGTTTGCAATTTCCTGTTTGTTTTGGTAATTTGAGTTTCTTTTAGTTGTTGATCTGCCT 2650                2670                2690
GCTTTTTGGTTTACGTCAGACTACTACTGCTGTTGTTGTTTGGTTTCCTTTCTTTCATTT 2710                2730                2750
TATAAATAAATAATCCGGTTCGGTTTACTCCTTGTGACTGGCTCAGTTTGGTTATTGCGA 2770                2790                2810
AATGCGAATGGTAAATTGAGTAATTGAAATTCGTTATTAGGGTTCTAAGCTGTTTTAACA 2830                2850                2870
GTCACTGGGTTAATATCTCTCGAATCTTGCATGGAAAATGCTCTTACCATTGGTTTTTAA

2890
TTGAAATGTGCTCATATGGGCCGTGGT
```

NUCLEIC ACID FRAGMENT ENCODING HERBICIDE RESISTANT PLANT ACETOLACTATE SYNTHASE

RELATED APPLICATIONS

This application is a divisional of copending application U.S. Ser. No. 07/642,976 filed Jan. 18, 1991, now U.S. Pat. No. 5,141,870, which is a divisional of application U.S. Ser. No. 07/164,360 filed Mar. 4, 1988 (and now issued as U.S. Pat. No. 5,013,659), which is a continuation-in-part of application U.S. Ser. No. 06/900,609 filed Aug. 26, 1986, now abandoned.

TECHNICAL FIELD

The present invention relates to nucleic acid fragments encoding a herbicide-resistant form of the enzyme acetolactate synthase (ALS).

BACKGROUND

Sulfonylurea herbicides such as sulfometuron methyl (I) and chlorsulfuron (II) inhibit growth of some bacteria, yeast and higher plants by blocking acetolactate synthase [ALS, EC 4.1.3.18], the first common enzyme in the biosynthesis of the branched-chain amino acids valine, leucine and isoleucine. The biosynthesis of branched-chain amino acids and, hence, the toxicity of sulfonylurea herbicides is restricted to plants and microbes. ALS is also inhibited by a structurally unrelated class of herbicides, the imidazolinones.

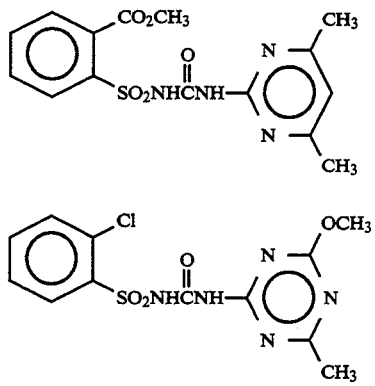

Three major isozymes of ALS, designated I, II and III, have been identified in enteric bacteria. Isozymes I and III, but not II, are sensitive to end-product inhibition by valine. Each of the three bacterial isozymes comprises a large and a small protein subunit. ALS enzymes from the yeast *Saccharomyces cerevisiae* and from some higher plants have been partially characterized and show some degree of end-product inhibition. It is not known if the yeast and plant ALS enzymes consist of one or more different polypeptides. Evidence suggests that the cellular locations of the yeast and plant ALS enzymes are in the mitochondria and chloroplasts, respectively.

Genes encoding ALS enzymes have been isolated from the enteric bacteria *Salmonella typhimurium* and *Escherichia coli,* and the yeast *S. cerevisiae.* The nucleotide sequences of the genes coding for the two subunits of *E. coli* ALS isozymes I, II and III show that they are organized as operons ilvBN, ilvGM and ilvIH, respectively. Comparison of the deduced amino acid sequences of the large subunits of the *E. coli* ALS isozymes shows three regions with about 50% conserved amino acids, comprising about two-thirds of the proteins, and separated by regions sharing little discernible homology. Amino acid sequence conservation, though less extensive, is also evident among the small subunits of the bacterial isozymes. In the yeast *S. cerevisiae,* a single gene, ILV2, essential for ALS activity was identified. Nucleotide sequence analysis of the ILV2 gene has revealed that the polypeptide encoded by it is homologous to the large subunits of the bacterial ALS isozymes. The deduced amino acid sequence of the yeast ALS shows the same degree of structural organization and the same degree of homology as is observed between the large subunits of the bacterial isozymes, except for about ninety amino acids at the amino terminus of the yeast protein that are believed to be involved in the translocation of the protein into the mitochondrion. No information on the structure of plant genes encoding ALS or the amino acid sequence of plant ALS enzymes was available prior to the inventions disclosed herein.

Enteric bacterial isozyme I is the only ALS in nature that is known to be insensitive to inhibition by sulfometuron methyl and chlorsulfuron. Therefore, enteric bacteria are sensitive to these herbicides only in the presence of valine, which inhibits isozyme I. Sulfonylurea herbicide-resistant mutant forms of the enteric bacteria *Salmonella typhimurium* and *E. coli* (selected in the presence of valine), the yeast *S. cerevisiae* and the higher plants *Nicotaiana tabacum* (tobacco), *Arabidopsis thaliana* and *Zea mays* (corn) have been identified. These mutant phenotypes cosegregate with herbicide-resistant forms of ALS through genetic crosses. In *S. typhimurium* the herbicide-resistance mutations are genetically linked to a gene encoding ALS, and in *E. coli* and *S. cerevisiae,* these mutations reside in the structural genes for ALS. In the higher plants the mutations responsible for the resistance are inherited as single, dominant or semidominant nuclear traits. In tobacco, these mutations map to either of two unlinked genetic loci.

The chemical control of undesirable weeds associated with agronomically useful crops requires the use of highly selective chemical herbicides. In some cases, it is difficult to identify any chemical which kills weeds without injury to the crop plant. The introduction of herbicide-resistance as a biological trait in crop plants would overcome this difficulty.

Although many genes involved in the structure and function of differentiated plant tissues and organs are not expressed in undifferentiated tissues, those involved in basic cellular functions are expressed and can be selected for in a disorganized callus or cell suspension culture. This has been demonstrated in many cases by the selection of a phenotype in tissue culture from which plants expressing the same phenotype have been regenerated. Examples include the in vitro selection of plants resistant to herbicides, pathotoxins or diseases, antibiotics, amino acid analogues, salt tolerance, etc.

Since acetolactate synthase is an enzyme involved in the basic cellular metabolic activity of amino acid biosynthesis, it was expected and has been demonstrated that genes encoding this enzyme are expressed in callus tissue as well as the whole plant. The sulfonylurea resistant tobacco mutants described in this patent, S4, C3 and Hra, were first selected in tissue culture and subsequently regenerated into whole plants in which the resistant phenotypes were retained in a genetically stable manner. Callus tissues derived from regenerated plants or their progeny continue to grow on concentrations of the herbicide which inhibit the growth of wild type callus. Thus resistance to a sulfonylurea herbicide at the plant cellular level is predictive of resistance at the whole plant level. In addition, it has been demonstrated in bacteria, yeast and higher plants that mutations resulting in the production of herbicide resistant ALS are sufficient to confer resistance at the cellular level and, in the case of plants, at the whole plant level. Therefore, the observation of herbicide-resistant ALS in extracts of plant cells is also predictive of herbicide resistant growth of cultured plant cells and herbicide resistant growth of whole plants.

Sulfonylurea herbicide resistant mutant tobacco and corn plants have been obtained by regeneration from mutant tissue culture cell lines and resistant Arabidopsis plants have been produced by seed mutagenesis. There are, however, significant advantages to be derived from isolation of a nucleic acid fragment able to confer herbicide resistance and its subsequent introduction into crops through genetic transformation. One can obtain cross species transfer of herbicide resistance, while avoiding potential limitations of tissue culture, seed mutagenesis, and plant breeding as techniques to transfer novel DNA fragments and traits. Plants exhibiting herbicide resistance achieved through transformation with a mutant ALS gene may possess distinct advantages relative to those regenerated after selection with a herbicide in tissue culture. The insertion of an additional gene or genes encoding an altered form of the ALS enzyme in the transformed plant can supply additional plant metabolic capabilities. It can also enable the plant molecular biologist to engineer desired selectivities into the added gene(s). Further, the insertion of the additional gene(s) in particular locations can result in enhanced levels of expression of the mutant ALS enzyme, as well as in different patterns of tissue or temporal expression of the gene. Such changes may result in production of new protein in root systems, for example. Tissue specific and/or temporal expression of the introduced gene can also be modulated through the substitution of specific gene regulatory sequences for the native gene regulatory sequences. Such substitutions can, for example, place gene expression under the control of chemical inducing agents. Finally, control of the chromosomal location of the inserted gene may avoid the complications of the native gene being linked to a disadvantageous allele which would require extensive plant breeding efforts to subsequently separate the traits. And, the absence of exposure of the plant tissues to mutagenic agents obviates the need for extensive backcrossing to remove undesirable mutations generated by these agents.

Although genes isolated from one plant have been introduced and expressed in other plants, non-plant genes have been expressed in plants only as chimetic genes in which the coding sequences of the non-plant genes have been fused to plant regulatory sequences required for gene expression. However, it would be difficult to introduce herbicide resistance into plants by introducing chimeric genes consisting of bacterial or yeast genes for herbicide-resistant forms of ALS, since (a) these microbial ALS enzymes are believed to lack a specific signal (transit) peptide sequence required for uptake into plant chloroplasts, the cellular location of plant ALS, (b) the bacterial isozymes consist of two different polypeptide subunits, and (c) the microbial ALS enzymes may not function optimally in the foreign cellular environment of higher plants. Therefore, there is a need for nucleic acid fragments (1) which encode a herbicide-resistant form of plant ALS, and (2) which can confer herbicide resistance when introduced into herbicide sensitive plants.

SUMMARY OF THE INVENTION

The present invention provides a nucleic acid fragment comprising a nucleotide sequence encoding plant acetolactate synthase. The nucleotide sequence comprises at least one sequence which encodes one of the substantially conserved amino acid subsequences designated A, B, C, D, E, F and G in FIG. 6. The nucleic acid fragment is further characterized in that at least one of the following conditions is met, a) the nucleic acid fragment has a sequence which encodes an amino acid sub-sequence A wherein $\epsilon_1$ is an amino acid other than alanine, or $\epsilon_2$ is an amino acid other than glycine, b) the nucleic acid fragment has a sequence which encodes an amino acid sub-sequence B wherein $\alpha_1$ is an amino acid other than proline, c) the nucleic acid fragment has a sequence which encodes an amino acid sub-sequence C wherein $\delta_2$ is an amino acid other than alanine, d) the nucleic acid fragment has a sequence which encodes an amino acid sub-sequence D wherein $\lambda_1$ is an amino acid other than lysine, e) the nucleic acid fragment has a sequence which encodes an amino acid sub-sequence E wherein $\gamma 1$ is an amino acid other than aspartic acid, f) the nucleic acid fragment has a sequence which encodes an amino acid sub-sequence F wherein $\beta_3$ is an amino acid other than tryptophan, or $\beta 8$ is an amino acid other than valine or $\beta_7$ is an amino acid other than phenylalanine, and g) the nucleic acid fragment has a sequence which encodes an amino acid sub-sequence G wherein $\sigma_1$ is an amino acid other than methionine.

In another embodiment, the instant invention provides a nucleic acid fragment encoding plant acetolactate synthase which is capable of being incorporated into a nucleic acid construct used to transform a plant containing wild-type acetolactate synthase which is sensitive to a sulfonylurea herbicide compound, said nucleic acid fragment having at least one point mutation relative to the wild-type nucleic acid fragment encoding plant acetolactate synthase such that upon transformation with said nucleic acid construct said plant contains said nucleic acid fragment and renders said plant resistant to the application of said sulfonylurea herbicide compound.

In another embodiment, the present invention provides an acetolactate synthase protein which is resistant to a sulfonylurea herbicide compound comprising an amino acid sequence wherein a substitution of at least one amino acid has occurred.

In still another embodiment, the present invention provides nucleic acid constructs, monocotyledonous and dicotyledonous plants, and tissue cultures which contain the specified nucleic acid fragment. The invention further provides methods for transforming plants with the specified fragments, selecting transformed plant cells, and growing transformed plants.

The present invention also provides a method for selecting plant cells transformed with the nucleic acid fragment of the present invention. The method comprises introducing the fragment into plant cells whose growth is sensitive to inhibition by herbicides to which the ALS encoded by the fragment is resistant to form a transformed plant cell. The transformed plant cells whose growth is resistant to the selected herbicide are identified by selection at a herbicide concentration which inhibits the growth of the untransformed plant cells.

In another aspect, the present invention is a method for controlling unwanted vegetation growing at a locus where a herbicide-resistant, agronomically useful plant (transformed with the nucleic acid fragment of the present invention) has been cultivated. The method comprises applying to the locus to be protected an effective amount of herbicide. In still another aspect, the present invention provides a nucleic acid fragment comprising the linkage of a nucleic acid fragment encoding acetolactate synthase conferring herbicide resistance and a second nucleic acid fragment conferring a second trait wherein said nucleic acid fragment is utilized to transform a plant and the expression of herbicide resistance by said plant upon application of sulfonylurea compound is utilized to detect the presence of said second nucleic acid fragment in said plant.

BRIEF DESCRIPTION OF THE DRAWINGS

FIG. 4 is a nucleotide sequence, and the cognate deduced amino acid sequence, of a gene from the Hra mutant of tobacco encoding a herbicide-resistant form of ALS from tobacco.

FIG. 5 is a nucleotide sequence, and the cognate deduced amino acid sequence, of a gene from the C3 mutant of tobacco encoding a herbicide-resistant form of ALS.

FIG. 6 is a comparison of deduced amino acid sequences of the large subunits of bacterial ALS and the yeast and plant ALS enzymes.

FIG. 8 is a comparison of deduced amino acid sequences of plant ALS enzymes.

FIG. 10 is a nucleotide sequence, and the cognate deduced amino acid sequence, of a gene from Arabidopsis encoding a herbicide-resistant form of ALS.

DETAILED DESCRIPTION OF THE INVENTION

Figure 1:
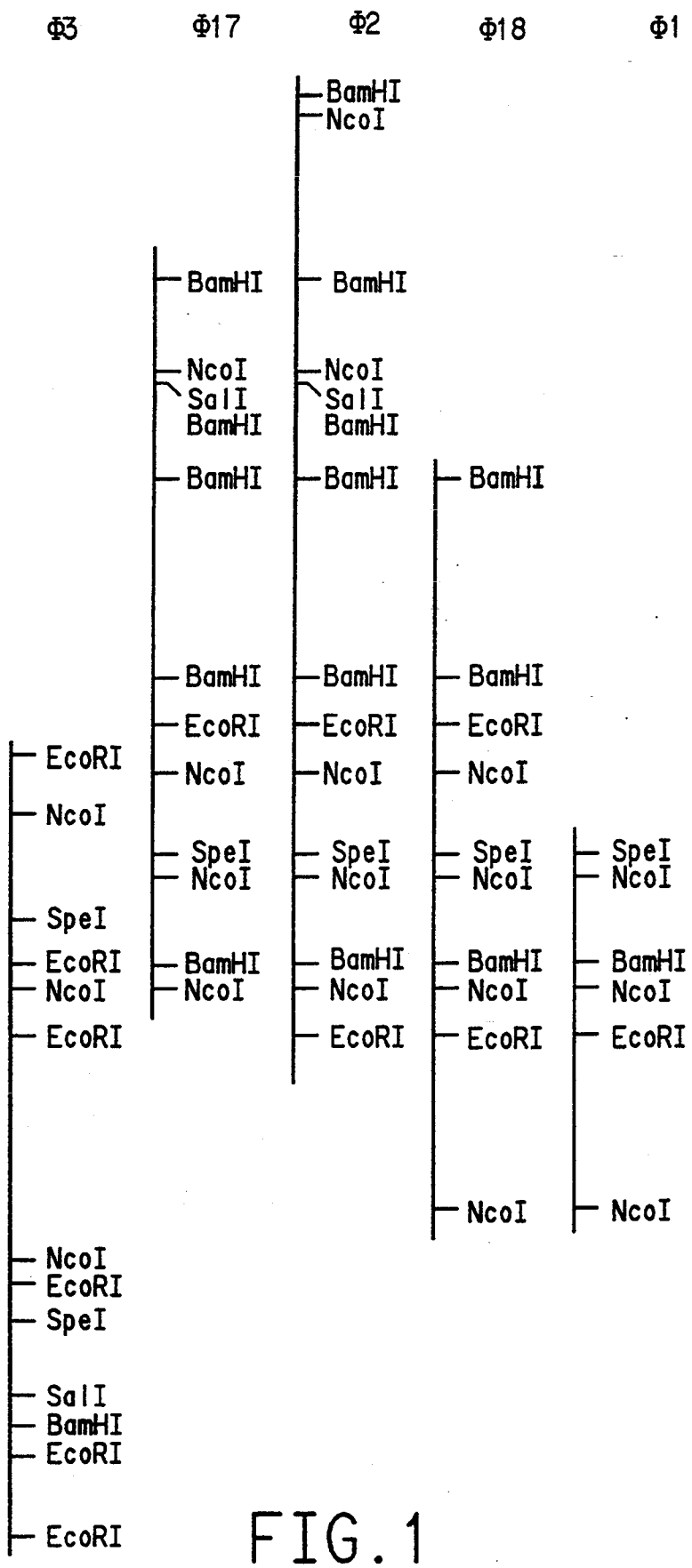
FIG. 1 is a physical map of nucleic acid insert fragments containing ALS genes isolated from a genomic library of DNA from the tobacco Hra mutant.

The present invention provides specified nucleic acid fragments which confer herbicide resistance when introduced into herbicide-sensitive plants. As used herein, the term "nucleic acid fragment" refers to a linear segment of single- or double-stranded deoxyribonucleic acid (DNA) or ribonucleic acid (RNA), which can be derived from any source. Preferably, the nucleic acid fragment of the present invention is a segment of DNA. The term "plant" refers to a photosynthetic organism including algae, mosses, ferns, gymnosperms, and angiosperms. The term, however, excludes prokaryotic and eukaryotic microorganisms such as bacteria, yeast, and fungi. "Plant cell" includes any cell derived from a plant, including undifferentiated tissue such as callus or gall tumor, as well as protoplasts, and embryonic and gametic cells. The term "plant acetolactate synthase" refers to the specified enzyme when expressed in a plant or a plant cell. The term "nucleotide sequence" refers to a polymer of DNA or RNA which can be single- or double-stranded, optionally containing synthetic, non-natural, or altered nucleotides capable of incorporation into DNA or RNA polymers. As used herein, the expression "substantially conserved amino acid sequences" refers to regions of amino acid homology between polypeptides comprising ALS enzymes from different sources. In the present invention seven substantially conserved amino acid sequences, designated A, B, C, D, E, F, and G are shown in FIG. 6. One skilled in the art could align the amino acid sequences of ALB enzymes from different sources to the schematic of FIG. 6 to identify the segments therein which are the substantially conserved amino acid sequences defined herein. The skilled person could then determine whether the identified segments have the characteristics disclosed and claimed in the present application. It is to be understood that the expression includes modifications of the segments which do not adversely affect the activity of the ALS enzyme. The term "nucleic acid construct" refers to a plasmid, virus, autonomously replicating sequence, phage or linear segment of a single- or double-stranded DNA or RNA, derived from any source, which is capable of introducing a nucleic acid fragment into a biological cell.

"Regulatory nucleotide sequence", as used herein, refers to a nucleotide sequence located 5' and/or 3' to a nucleotide sequence whose transcription and expression is controlled by the regulatory nucleotide sequence in conjunction with the protein synthetic apparatus of the cell. As used herein, a "regulatory nucleotide sequence" can include a promoter region, as that term is conventionally employed by those skilled in the art. A promoter region can include an association region recognized by an RNA polymerase, one or more regions which control the effectiveness of transcription initiation in response to physiological conditions, and a transcription initiation sequence.

"Transit peptide" refers to a signal polypeptide which is translated in conjunction with a polypeptide encoded by a product nucleotide sequence, forming a polypeptide precursor. In the process of transport to a selected site within the cell, for example, a chloroplast, the transit peptide can be cleaved from the remainder of the polypeptide precursor to provide an active or mature protein.

"Herbicide," as used herein, refers to an antibiotic compound which inhibits the metabolism, growth, or replication of plant cells or whole plants. Cells transformed with a construct of the present invention exhibit selectable cross-resistance to certain structurally related sulfonamide compounds effective as broad-spectrum preemergent and postemergent herbicides. As used herein in a generic sense, "sulfonylurea herbicides" refer to N-(heterocyclicaminocarbonyl)arylsulfonamide compounds exhibiting broad-spectrum herbicidal activity and low mammalian toxicity. "Selective concentration" refers to a concentration of an inhibitor or antibiotic compound, for example, a herbicide, which is capable of inhibiting the metabolism, growth, or multiplication of a wild-type cell or organism. Such an organism, as well as clones thereof, is referred to as a "sensitive" organism or cell. "Resistance" refers to a capability of an organism or cell to grow in the presence of selective concentrations of an inhibitor. In relation to particular enzymes or proteins, "sensitive" indicates that the enzyme or protein is susceptible to specific inhibition by a particular inhibiting compound, for example, an antibiotic or herbicide. In relation to particular enzymes or proteins, "resistant" indicates that the enzyme or protein, as a result of a different chemical structure, expresses activity in the presence of a selective concentration of a specific inhibitor which inactivates sensitive variants of the enzyme or protein. The term "selectable genetic marker" refers to a nucleotide sequence which, when incorporated into the genome of an organism, allows growth of that organism and its progeny under conditions which inhibit growth of the organism lacking the selectable genetic marker. For example, a gene which encodes an enzyme that is resistant to specific inhibition by a particular antibiotic compound, such as a herbicide, can function as a selectable genetic marker by allowing an organism, such as a plant, to grow and propagate in the presence of a selective concentration of the compound. A second nucleic acid fragment, controlling a property which is difficult to assay, can be covalently linked to the selectable genetic marker, in which case the presence of the selectable marker, indicated by growth of an organism under selective conditions, can be used to detect an organism containing the second nucleic acid fragment.

PREPARATION OF DNA FRAGMENTS ENCODING HERBICIDE-RESISTANT ALS

Callus cultures of sensitive tobacco (*Nicotiana tabacum* vat. Xanthi) were exposed to sulfometuron methyl at 2 ppb according to the method described by Chaleff, U.S. Pat. No. 4,443,971. Resistant cell lines designated C3 and S4 were selected. Standard genetic analysis of plants regenerated from these cell lines indicated that the C3 and S4 lines each carried a single semi-dominant nuclear gene mutation responsible for the herbicide resistance trait and that the C3 and S4 mutations were not genetically linked, i.e. were in different genes designated SURA and SURB, respectively. The C3 and S4 lines were shown to produce ALS enzyme activity one-hundred fold more resistant to the sulfonylurea herbicides chlorsulfuron and sulfomenturon methyl than ALS from wild type. Production of herbicide resistant ALS activity cosegregated in genetic crosses with resistance to growth inhibition by the herbicides. The observation of two different genes that had mutated to form herbicide resistant ALS was not unexpected because *N. tabacum* is believed to be an allotetraploid plant formed from *N. tomentosiformis* and *N. sylvestris*, essentially containing two complete genomes. Thus, the S4 and C3 cell lines each contain one mutant and one wild type ALS gene. The S4 cell line was exposed to sulfometuron methyl at 200 ppb, a selective concentration which completely inhibits the growth of S4. Cell lines resistant to 200 ppb were identified; one such line was designated Hra. Hra was shown to tolerate concentrations of sulfometuron methyl one thousand times greater than that required to completely inhibit the growth of wild type callus. Hra was shown to be cross resistant to chlorsulfuron. Plants were regenerated from Hra callus cultures. Genetic analysis of the plants demonstrated that the Hra and S4 mutations were linked indicating that the Hra line contained a second mutation in the mutant gene of the progenitor S4 line. ALS activity in extracts of leaves of wild type and homozygous Hra mutant tobacco plants was determined. The ALS activity in the extract from Hra mutant plants was about one thousand fold more resistant to chlorsulfuron than was the activity of the wild type plants. Hra mutant plants were further shown to be cross resistant to the foliar application of the following compounds:

2-[4,5-dihydro-4-methyl-4-(1-methylethyl)-5-oxo-1H-imidazol-2-yl]-3-pyridinecarboxylic acid, (1-methylethanamine) salt;

5-ethyl-4,5-dihydro-2-[4-methyl-4-(1-methylethyl)-5-oxo-1H-imidazol-2-yl]-3-pyridinecarboxylic acid;

2-(2-chloroethoxy)-N-[(4-methoxy-6-methyl-1,3,5-triazin-2-yl)aminocarbonyl]benzenesulfonamide;

2-chloro-N-[(4-methoxy-6-methyl-1,3,5-triazin-2-yl)aminocarbonyl]benzenesulfonamide;

2-[[(4-chloro-6-methoxypyrimidin-2-yl)aminocarbonyl]aminosulfonyl]benzoic acid, ethyl ester;

N-[(4,6-dimethoxypyrimidin-2-yl)aminocarbonyl]-2,3-dihydro-2-methylbenzo[β]thiophene-7-sulfonamide, 1,1-dioxide;

7-chloro-N-[(4,6-dimethoxypyrimidin-2-yl)aminocarbonyl]-3,4-dihydro-2-methyl-2H-1,2-benzothiazine-8sulfonamide, S,S-dioxide;

2-[[(4-methoxy-6-methylpyrimidin-2-yl)aminocarbonyl]aminosulfonyl]-6-methylbenzoic acid, methyl ester;

5,7-dimethyl-N-(2-methyl-6-nitrophenyl)[1,2,4]-triazolo[1,5-A]pyrimidin-2-sulfonamide;

2-[4,5-dihydro-4-methyl-4-(1-methylethyl)-5-oxo-1H-imidazol-2-yl]-3-quinolinecarboxylic acid;

6-(4-isopropyl-4-methyl-5-oxo-2-imidazolin-2-yl)-m-toluic acid and p-toluic acid, methyl esters;

2-[[(4,6-dimethylpyrimidin-2-yl)aminocarbonyl]aminosulfonyl]benzoic acid, methyl ester:

N-(2,6-dichlorphenyl)-5,7-dimethyl[1,2,4]triazolo [1,5-A]pyrimidin-2-sulfonamide;

N-(2-chloro-6-methylphenyl)-5,7-dimethyl[1,2,4]-triazolo[1,5-A]pyrimidin-2-sulfonamide.

In order to clone a herbicide resistant ALS gene, tobacco DNA was isolated from the S4 homozygous mutant line of *Nicotiana tabacum*. 50 g portions of callus tissue were frozen in liquid $N_2$, and then lyophilized. The resulting dried tissue was then ground at about 23° C. in a blender, using 15 second bursts, until powdered. Ten volumes of a sucrose buffer (0.3M sucrose. 50 mM Tris-HCl pH 8.0, 5 mMMgCl$_2$) were added, and the resulting suspension was incubated at 0° C. for 5 minutes. The suspension was then filtered through cheesecloth, and centrifuged at 350×g for 10 minutes. The nuclear pellet was then resuspended in lysis buffer (20 mM EDTA, 50 mM Tris-HCl pH 8.0, 1% Sarkosyl), CsCl added to provide 0.95 g per mL buffer, and the resulting mixture centrifuged at 17,000×g for 20 minutes at 4°. Ethidium bromide was added to the resulting supernatant to a concentration of 400 μg per mL, the refractive index was adjusted to 1.39, and the resulting solution centrifuged at 90,000×g in a Beckman Ti70 rotor at 20° C. for 3 days. The resulting fluorescent DNA band was removed from the gradient, and treated with isopropanol to extract the ethidium bromide. Finally, the DNA was dialyzed against TE buffer and precipitated by addition of ethanol.

A Nicotiana genomic library was prepared from this DNA as follows, using the phage lambda vector EMBL4 described by Frischauf et al., *J. Mol. Bio.* 170:827 (1983). EMBL4 phage was prepared from agarose plate stocks prepared by the method of Davis et al; *Advanced Bacterial Genetics,* (Cold Spring Harbor Laboratory, New York, 1980). Phage DNA was prepared as described by Silhavy et al., *Experiments with Gene Fusions,* (Cold Spring Harbor Laboratory, New York, 1984), by concentrating phage with polyethylene glycol, removing the polyethylene glycol by chloroform extraction, and purifying phage using glycerol step gradients. The resulting purified phage was then treated with deoxyribonuclease and ribonuclease prior to phenol extraction. Phage DNA was spooled from ethanol. To prepare arms of the EMBL4 phage, phage DNA was sequentially digested with Sal I and Bam HI endonucleases. The arms were annealed and then separated from the central fragment on a 10–40% sucrose gradient, as described by Maniatis et al., *Molecular Cloning: A Laboratory Manual.* (Cold Spring Harbor Laboratory, New York, 1982). The arms were completely denatured and reannealed prior to ligation to tobacco DNA. Tobacco DNA, prepared as previously described, was partially digested with Sau3A endonuclease and sedimented through a 10–40% sucrose gradient, Fractions from the sucrose gradient were then analyzed by electrophoresis on 0.5% agarose gels. Fractions containing fragments in the 20–40 kb size range were dialyzed, precipitated, and ligated to the lambda phage DNA arms. The DNA was ligated at a concentration of 135 μg per mL vector and 45 μg per mL insert DNA. The resulting ligated concatamers were then packaged using lambda DNA packaging extracts. The resulting yield of phage was approximately $4.5 \times 10^5$ phage per μg insert DNA. A library of approximately 400,000 phage was constructed, representing an estimated 99% complete library for tobacco, which has an approximate genomic content of 1.65 picograms, or $1.52 \times 10^9$ base pairs (Zimmerman, et al., *Chromosoma* 59:227 1977).

The resulting phage library of Nicotiana DNA was grown and plated on *E. coli* stain LE392 (ATCC 33572), as disclosed by Silhavy et al., *Experiments with Gene Fusions,* (Cold Spring Harbor Laboratory, New York, 1984). Phage were plated to provide 2000–5000 plaques on 90 mm petri dishes or 50,000 plaques on 150 mm petri dishes. Plaque lifts were done by the method of Benton et al., *Science* 196:180 (1977). Following transfer of phage DNA to nitrocellulose filters, the filters were prohybridized by incubation for about 4 hours at 56° C. in 6×SBPE containing 0.5% SDS, 100 μg per mL denatured calf thymus DNA, and 10×Denhardt's solution. Hybridization was then accomplished as described by Maniatis, et al., *Molecular Cloning: A Laboratory Manual,* (Cold Spring Harbor Laboratory, New York, 1982) p. 326. In this step, a fresh aliquot of hybridization solution was added, together with about $10^8$ cpm of the radioactive yeast ALS gene probe. Hybridization was allowed to occur for about 24–48 hours at 56° C. At this point, the filters were first rinsed for about 4 hours in 6×SSPE at 56° C., then rinsed three additional times for 20 minutes each in 2×SSPE at about 23° C. The filters were than dried and exposed at −70° C. for 2 days, using Kodak XAR or XRP x-ray film and a Du Pont Cronex® Lightning Plus ™ intensifying screen. Exposed spots on the film indicated the position of plaques potentially containing Nicotiana ALS genes.

The autoradiograms prepared as described above were then oriented over the original bacteriophage-containing petri dishes. Using the wide end of a sterile Pasteur pipette, plaques corresponding to the darkest spots on the autoradiograms were excised. The plaques selected were then eluted into SM buffer and plated onto fresh 90 mm petri dishes. Each dish received about 100–200 phage. The complete phage location process was then reiterated, using freshly prepared probe. In this manner, the phage location and isolation steps were repeated until the majority of plaques indicated the presence of phage containing DNA capable of hybridization to the yeast ALS gene probe.

Mini-preparations of DNA from the plaque-purified phage designated NtA13 were isolated as described and worked up as described by Maniatis et al, *Molecular Cloning: A Laboratory Manual* (Cold Spring Harbor Laboratory, New York, 1982), p. 371. EcoRI restriction endonuclease digests of the DNA mini-preparations were electrophoresed through 0.7% agarose gels and blotted onto nitrocellulose filters. Fragments containing the ALS gene were then identified by hybridization with the yeast ALS gene probe. Fragments capable of hybridization to the probe were then isolated and subcloned into vectors pBR322, M13mp9, or M13mp18. These fragments were then sequenced using oligonucleotide primers in a dideoxy chain termination procedure conducted substantially as described by Sanger et al., *Proc. Natl. Acad. Sci. USA* 74:5463 (1977). A kit available from New England Biolabs (Beverly, Mass., U.S.A.) was employed. Use of synthetic oligonucleotide primers allowed extension of a DNA sequence along a cloned fragment in overlapping segments. Computer analysis of the DNA sequence identified a 667 codon open reading frame. The deduced amino acid sequence of this open reading frame was substantially homologous to the sequences previously determined from the *Sacharomyces cerevisiae* ILV2 gene and the *E. coli* ilvG gene, indicating that the DNA fragment recovered from the Nicotiana genomic library contained a tobacco ALS gene. To determine whether this ALS gene encoded the wild type herbicide sensitive enzyme or the mutant herbicide resistant enzyme from the S4 line, the gene was introduced into wild type herbicide sensitive tobacco by *Agrobacterium tumefaciens* mediated transformation.

The results shown in Table 1 indicated that transformation of tobacco had been achieved based on production of kanamycin resistant callus. The kanamycin resistant callus remained sensitive to the sulfonylurea herbicide chlorsulfuron, whether or not the tobacco ALS gene was present, indicating that the ALS gene isolated from the tobacco S4 mutant in phage Nta 13 encoded the wild type herbicide sensitive enzyme. This plant ALS gene has been used as a DNA hybridization probe to isolate other plant ALS genes, including genes which encode herbicide resistant ALS, and has been mutagenized in vitro to encode herbicide resistant forms of ALS.

TABLE 1

Results from Callus Tests of GVKNT13 Infected Tobacco Number of transformed shoot explants producing callus on selective and non-selective media.

| | GVKNT13[1] | GVKK[2] | GV3850[3] |
|---|---|---|---|
| Exp. #1 | | | |
| No selection | 59/62 | 12/13 | 10/10 |
| Kanamycin, 50 mg/L | 53/62 | 8/13 | 0/10 |
| Chlorsulfuron, 10 ppb | 0/62 | 0/13 | 0/10 |
| Exp. #2 | | | |
| No selection | 96/102 | 21/23 | 22/25 |

TABLE 1-continued

Results from Callus Tests of GVKNT13 Infected Tobacco
Number of transformed shoot explants producing callus on
selective and non-selective media.

|  | GVKNT13[1] | GVKK[2] | GV3850[3] |
|---|---|---|---|
| Kanamycin, 50 mg/L | 81/102 | 16/23 | 0/25 |
| Chlorsulfuron, 10 ppb | 0/102 | 0/23 | 0/25 |

[1]Agrobacterium strain containing Ti plasmid carrying tobacco ALS gene and NOS/NPTII gene (Kanamycin resistance)
[2]Agrobacterium strain containing Ti plasmid carrying only NOS/NPTII gene
[3]Agrobacterium strain containing Ti plasmid (devoid of either tobacco ALS or NOS/NPTII genes)

A genomic library of DNA from the Hra mutant of tobacco was made in bacteriophage lambda and screened for clones that hybridized to the wild type tobacco ALS gene from the S4 mutant. Several phage clones were isolated. Physical mapping of the tobacco DNA inserts using restriction endonucleases revealed the presence of two distinct classes of DNA fragments representative of the two tobacco ALS genes SURA and SURB. Comparison of the physical maps of the SURA and SURB genes of *N. tabacum* to maps from the progenitor species showed that the SURA gene came from *N. sylvestris* and the SURB gene came from *N. tomentosiformis*. The wild type ALS gene isolated previously from the S4 mutant was designated SURA. The genetic linkage of the high level herbicide resistance mutation in Hra to the S4 mutation indicated that the Hra mutation was in the same ALS gene as the S4 mutation, namely SURB. Therefore, it was expected that the SURB gene isolated from the Hra mutant would be a mutant gene, designated SURB-Hra, encoding a herbicide resistant ALS. One phage clone containing the SURB-Hra gene was chosen for further analysis. This phage clone, designated 3, has been deposited at the ATCC, Rockville, Md. under accession number ATCC 40237. The phage clone was digested with Spe I restriction endonuclease to give an 8.3 Kb DNA fragment which was inserted into the Xba I site of plasmid pMuc19, and the resulting recombinant plasmid, pAGS148, has been deposited at the ATCC, Rockville, Md. under accession number ATCC 67124. Plasmids pAGS148 and pAGS135 were ligated to each other as described below, and the resulting recombinant plasmid pAGS152 (FIG. 2) was introduced into *Agrobacterium tumefaciens* LBA 4404. The resultant *Agrobacterium tumefaciens* LBA 4404 (pAGS152) has been deposited at the ATCC, under accession number ATCC 67126.

A genomic library of DNA from the tobacco C3 mutant was made in bacteriophage lambda and screened for clones which hybridized to the previously isolated ALS genes from tobacco. Several phage clones were isolated and the tobacco DNA inserts were physically mapped with restriction endonucleases. Two different DNA fragment types, corresponding to the SURA-C3 gene and the SURB gene, were identified. Two phage clones designated 35 and 38, carrying the SURA-C3 gene were chosen for further analysis.

Figure 3:
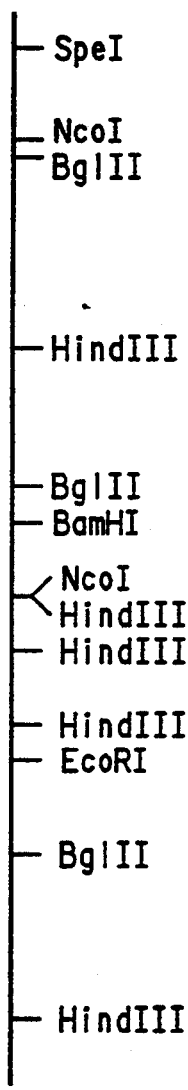
FIG. 3 is a physical map of a nucleic acid insert fragment in phage clone 35 isolated from genomic library of DNA from the tobacco C3 mutant.

Phage clone 35 was digested with Spe I and Sal I restriction endonucleases to give the 6.3 kb DNA fragment shown in FIG. 3. This DNA fragment has been inserted into the plasmid vector pUC119 digested with restriction endonucleases Xba I and Sal I, and the resulting recombinant plasmid, pALS35, has been deposited at the ATCC, Rockville, Md., under accession number 67424.

Figure 7:
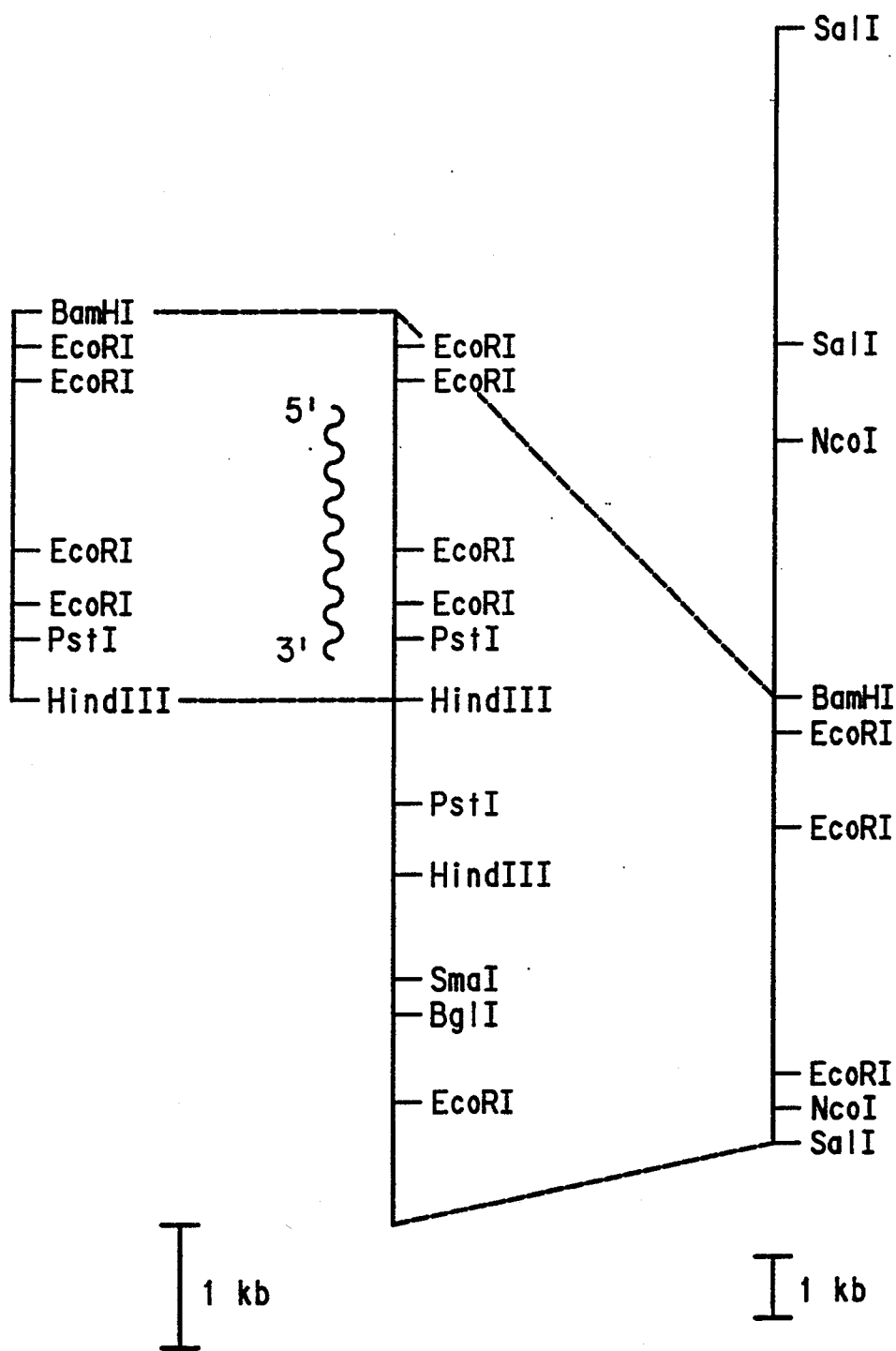
FIG. 7 is a physical map of a nucleic acid insert fragment and sub-fragments derived from phage clone 21 isolated from a genomic library of sugarbeet DNA.

In addition to the four tobacco ALS genes, SURA and SURB encoding wild type herbicide sensitive ALS, and SURA-C3 and SURB-Hra encoding mutant herbicide resistant ALS, ALS genes have been isolated from *Arabidopsis thaliana, Beta vulgaris* (sugarbeet) and *Zea mays* (corn). The latter ALS genes, from herbicide sensitive plants, were obtained from genomic DNA libraries made in bacteriophage lambda by screening for DNA hybridizing to a previously isolated ALS gene from yeast or tobacco. The wild type ALS gene from sugarbeet was isolated in a phage designated φ21 and physically mapped with restriction endonucleases. The DNA fragment isolated in this phage and two DNA fragments which were subcloned into the plasmid vector pUC119 are shown in FIG. 7. Plasmid pSBALS216 has been deposited at the ATCC, Rockville, Md. under accession number 67425.

A gene encoding a sulfonylurea resistant form of ALS was also isolated from Arabidopsis. Sulfonylurea resistant mutants of Arabidopsis were obtained following ethyl methane sulfonate mutagenesis of seeds. The mutant ALS gene was identified from a genomic DNA library made in bacteriophage λ by hybridization to the wild type Arabidopsis gene. A 6.1 kb Xba I DNA fragment that contains the entire functional gene subcloned in the plasmid pKAR (FIG. 9) has been deposited at the ATCC, Rockville, Md. under accession number ATCC 67137.

FIG. 1 shows restriction endonuclease maps of DNA fragments containing ALS genes isolated from the Hra mutant of tobacco. Based on these maps, two classes of DNA fragments can be distinguished. An approximately 18 kilobase nucleic acid insert in phage clone 3 carries the SURB-Hra gene. The insert contains a preferred DNA fragment of the present invention which encodes a herbicide-resistant ALS from tobacco mutant Hra. This nucleic acid fragment consists of double-stranded DNA of 8.3±0.5 kilobases and has a molecular weight of 5.5±0.3 mega daltons, and has 5' overhang sequences of CTAG at both ends. The 8.3 kilobase nucleic acid fragment between the two Spe I sites hybridized to the ALS gene probe used to screen the genomic library. Restriction endonuclease Spe I can be used to excise the fragment from the phage using well-known techniques.

Figure 2:
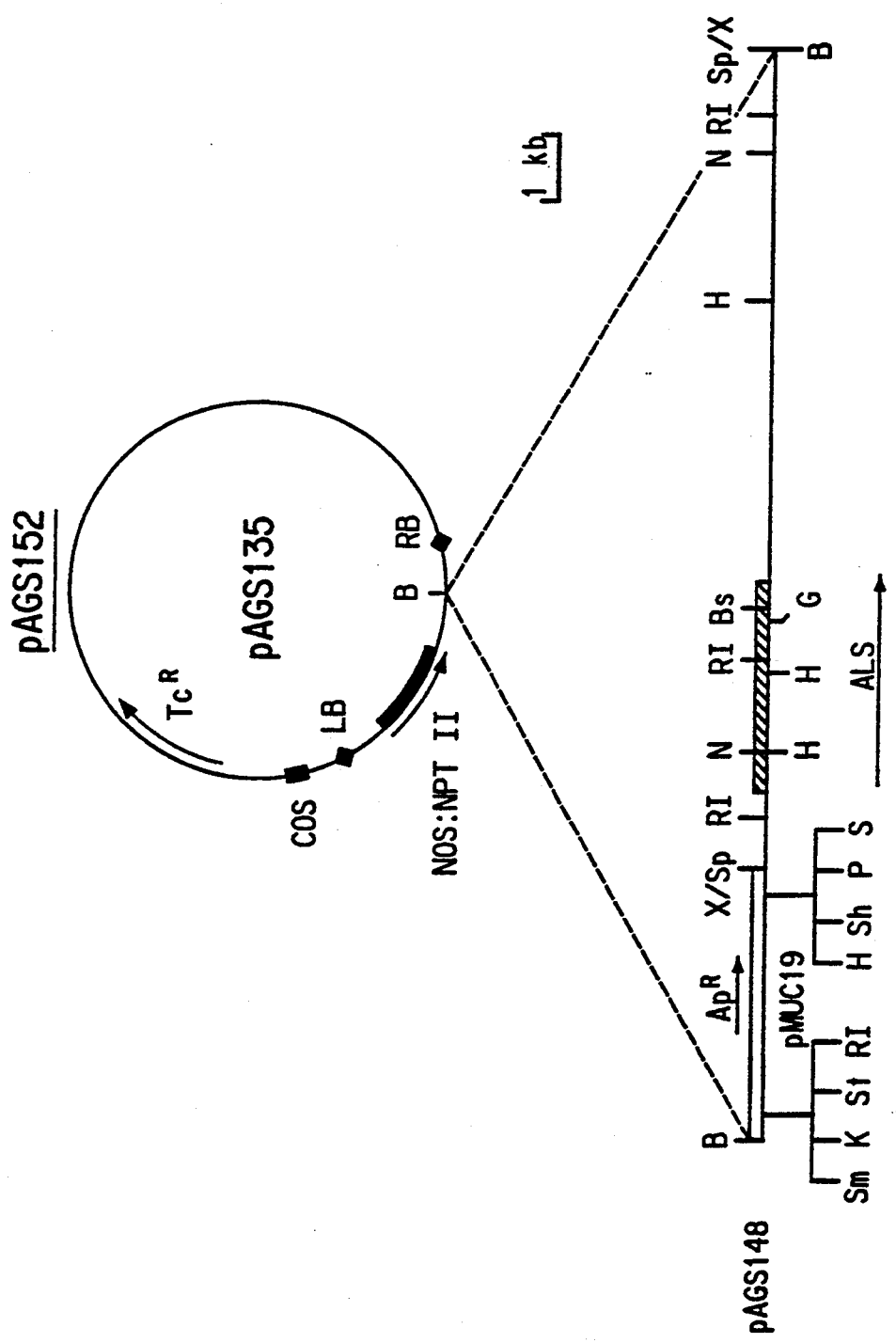
FIG. 2 is a diagram of plasmid pAGS152 showing a physical map of the nucleic acid fragment from tobacco encoding a herbicide-resistant ALS.

FIG. 2 shows a physical map of plasmid pAGS152. Plasmids pAGS135 and pAGS148 are not drawn to scale. Restriction endonuclease sites EcoR I (RI), BamH I (B), Xba I (X), Pst I (P), Sal I (S), Spe I (Sp), Nco I (N), Hind III (H), BstE II (Bs), Sma I (Sm), Kpn I (K), Sst I (St), Sph I (Sh) and Bgl II (G) are shown. pAGS152 results from the ligation of the BamH I-cleaved plasmids pAGS135 (approximately 27 kilobases) and pAGS148 (approximately 12.1 kilobases). Plasmid pAGS135, drawn as a circle, is a wide host range plasmid containing a plant kanamycin resistance gene (NOS:NPT II) and a BamH I cloning site, flanked by the left border (LB) and the right border (RB) of T-DNA. Plasmid pAGS148, shown as a linear BamH I fragment, consists of the Spe I (Sp) fragment (approximately 8.3 kilobases) of the aspect of the invention (shown flanked by X/Sp and Sp/X), containing the coding sequence for the herbicide-resistant form of ALS, from the Hra mutant, inserted in the Xba I site (X) of plasmid pMuc19 (open box). Although Spe I and Xba I restriction enzymes recognize different sequences, their action results in DNA fragments with the same 5' overhanging sequence, viz 5'-CTAG-3'. Thus, Spe I and Xba I digestd fragments can be ligated to each other, but the ligation results in a loss of both sites. The hatched box on the insert fragment corresponds to the coding region of the ALS gene and the arrow denotes the 5'→3' direction of the coding sequence. The nucleic acid fragment is flanked by Hind III, Sph I, Pst I and Sal I sites at one end and by BamH I, Sma I, Kpn I, Sst I and EcoR I sites at the other end. These enzymes can be used to excise the fragment from the plasmid by complete or partial digestion using well-known techniques. After digestion, the ends of the fragment will be characteristic of the endonuclease used to excise the fragment:

| 5' Overhanging Sequence | | 3' Overhanging Sequence | |
|---|---|---|---|
| Spe I | 5'-CTAGT-3'<br>3'-A-5' | Sph I | 5'-C-3'<br>3'-GTACG-5' |
| Hind III | 5'-AGCTT-3'<br>3'-A-5' | Pst I | 5'-G-3'<br>3'-ACGTC-5' |
| Sal I | 5'-TCGAC-3'<br>3'-G-5' | Kpn I | 5'-C-3'<br>3'-CATGG-5' |
| BamH I | 5'-GATCC-3'<br>3'-G-5' | Sst I | 5'-C-3'<br>3'-TCGAG-5' |
| EcoR I | 5'-AATTC-3'<br>3'-G-5' | | |
| | Blunt end | | |
| Sma I | 5'-GGG-3'<br>3'-CCC-5' | | |

The 8.3 kilobase fragment can be isolated from the restriction digest using agarose gel electrophoresis. The fragment can be characterized by the restriction map shown in FIG. 2, and contains the coding sequence for ALS from mutant plant Hra of *Nicotiana tabacum* cv. 'Xanthi' which is resistant to inhibition by chlorsulfuron and sulfometuron methyl. The fragment also contains regulatory nucleotide sequences required to express the gene in plants.

FIG. 3 shows a restriction endonuclease map of the approximately 6.8 kb preferred nucleic acid fragment which carries the SURA-C3 gene. This DNA fragment was obtained from lambda phage clone 35 by digestion with restriction endonucleases SpeI and SalI and was inserted into the plasmid vector pUC119 which had been digested with restriction endonucleases Xba I and Sal I, as described in the legend to FIG. 2.

FIG. 4 shows a partial nucleotide sequence of a preferred DNA fragment encoding a herbicide-resistant form of ALS from SURB-Hra gene of tobacco. Nucleotides are indicated by their bases by the following standard abbreviations:
A=adenine:
C=cytosine;
T=thymine:
G=quanine.
The beginning of the nucleotide sequence corresponds to Pst I Site (P) 885 nucleotide bases preceding the coding sequence, shown on FIG. 2; the sequence ends at base number 2946, which is 67 bases past the end of the coding sequence shown in FIG. 2. The nucleotide sequence from nucleotide one to nucleotide 884 is believed to contain 5' regulatory sequence(s) required for expression of the encoded ALS. FIG. 4 also shows the deduced amino acid sequence of the ALS protein.

Amino acid residues are indicated by the following abbreviations:

A=alanine:
C=cysteine;
D=aspartic acid;
E=glutamic acid;
F=phenylalanine;
G=glycine;
H=histidine:
I=isoleucine;
K=lysine;
L=leucine;
M=methionine;
N=asparagine;
P=proline;
Q=glutamine:
R=arginine;
S=serine;
T=threonine;
V=valine;
W=tryptophan; and
Y=tyrosine.
The term "amino acids" as used herein is meant to denote the above-recited natural amino acids and functional equivalents thereof.

FIG. 5 shows a partial nucleotide sequence and its cognate deduced amino acid sequence, of a preferred DNA fragment encoding a herbicide-resistant form of ALS from the C3 gene of tobacco. The beginning of the nucleotide sequence corresponds to the BamH I site shown in FIG. 3. The coding sequence begins at nucleotide 176 and ends at nucleotide 2175. The nucleotide sequence from nucleotide one to nucleotide 175 is believed to contain 5' regulatory sequence(s) necessary, but not sufficient, for expression of the encoded ALS. Nucleotides and amino acids are indicated by the standard abbreviations, as shown above.

FIG. 6 shows the deduced amino acid sequences of the large subunits of ALS isozymes I, II and III from *E. coli* (Lines E, F and G respectively), wild type ALS proteins of yeast (Line D), *Arabidopsis thaliana* (Line C) and *Nicotiana tabacum* (tobacco) (Lines A and B), encoded by the SURB and SURA genes, respectively. Amino acid residues are indicated by standard abbreviations as shown above. The first amino acid, methionine, of the deduced amino acid sequences of the yeast (line D, FIG. 6) and higher plant (lines A-C) ALS proteins is the putative start of the transit peptides believed to be involved in translocating the enzymes into mitochondria, in the case of the yeast enzyme, or chloroplasts, in the case of the plant enzymes. These transit peptides are believed to be cleaved off during translocation of the proteins into the organelles and are believed not to be required for ALS activity. The extent of these transit peptides is difficult to determine in the absence of data on the in vivo N-termini of the ALS proteins of yeast and higher plants. Based on the homology with the bacterial ALS proteins the chloroplast and mitochondrial transit sequences may be estimated to extend for 90 amino acids.

The dotted lines in the sequences are spacing marks inserted to best align regions of homology. Vertical lines highlight the amino acid residues that are conserved between adjacent sequences of FIG. 6. The homology between tobacco and Arabidopsis ALS proteins (lines A to C), which derive from two different plant families, is striking. Even more unexpected, considering the evolutionary distance between microbes and higher plants, is the finding that the amino acid residues which are conserved between the bacterial (lines E to G) and the yeast (line D) ALS proteins are largely conserved between these proteins and the plant ALS proteins.

FIG. 7 shows a restriction endonuclease map of the approximately 17.5 kilobase nucleic acid insert in phage clone φ21 carrying the sugarbeet ALS gene. Two smaller DNA fragments which also contain the sugarbeet ALS gene and which were subcloned into the pUC119 plasmid vector are also shown.

FIG. 8 shows deduced amino acid sequences of wild type ALS proteins from the plants *Nicotiana tabacum* (tobacco) (Lines A and B). *Arabidopsis thaliana* (Line C) *Beta vulgaris* cv. sennica (sugarbeet) (Line D) and a partial sequence of the ALS protein from maize (Line E). The dotted lines in the sequences are spacing marks to best align regions of homology. Vertical lines highlight the amino acid sequences that are conserved between adjacent sequences. The homology between all of the plant ALS proteins is very extensive. Based upon this, a mutation in one plant ALS gene causing an amino acid substitution that results in sulfonylurea herbicide resistant ALS would be expected to have an analogous effect if it were present in any other plant ALS gene.

Figure 9:
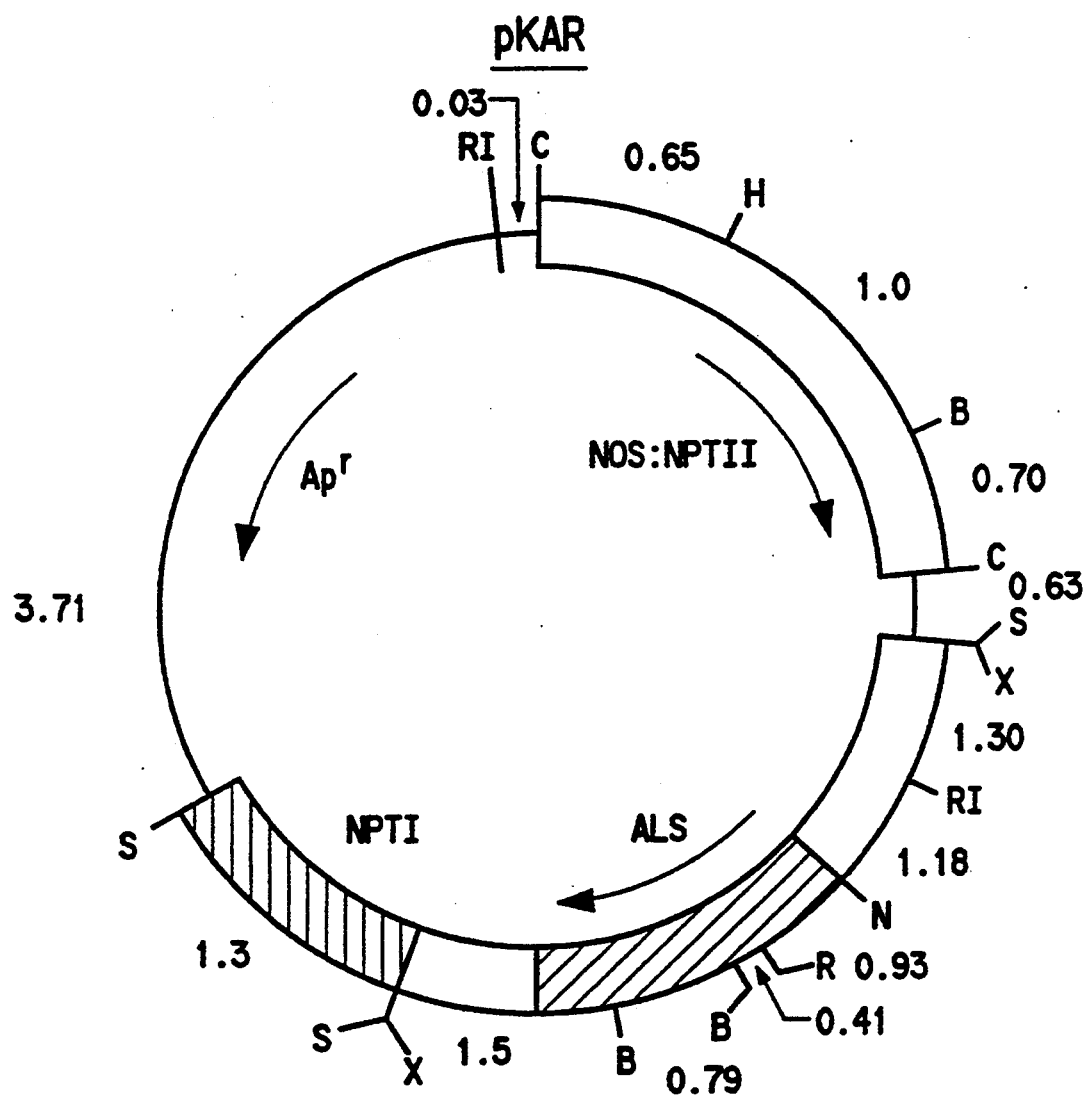
FIG. 9 is a diagram of plasmid pKAR showing a physical map of the nucleic acid fragment from Arabidopsis encoding a herbicide-resistant ALS.

FIG. 9 shows a diagram of plasmid pKAR. Restriction sites Eco RI (RI), Cla I (C), Hind III (H), Bam HI (B), Sal I (S), Xba I (X), and Nco I (N) are shown. The numbers between the restriction sites are the distances between the sites, in kilobases. The open box represents the chimetic NOS:NPT II gene in which the coding sequence of a neomycin phosphotransferase (NPT II) gene on a 1 kilobase Hind III-Bam HI fragment, is fused to the promoter region of a nopaline synthase (NOS) gene, on a 0.65 kilobase Cla I-Hind III fragment, and to the 3' regulatory sequences of the NOS gene on a 0.7 kilobase Bam HI-Cla I fragment. The NOS:NPT II chimetic gene expresses kanamycin resistance in plant cells. The hatched box represents 1.3 kilobases of a bacterial gene for NPT I that expresses kanamycin resistance in *E. coli* and Agrobacterium. The stippled box represents a 5.3 kilobase Xba I fragment containing the coding sequence of the herbicide-resistant from Arabidopsis.

FIG. 10 shows a partial nucleotide sequence and its cognate deduced amino acid sequence, of a preferred DNA fragment encoding a herbicide-resistant form of ALS. The coding sequence begins at nucleotide 506 and ends at nucleotide 2518. The nucleotide sequence from nucleotide one to nucleotide 505 is believed to contain the 5' regulatory sequence(s) required for expression of the encoded ALS. Nucleotides and amino acids are indicated by the standard abbreviations, as shown above.

The amino acid residues which are conserved in all of the ALS sequences in FIG. 6 are believed to be important for the binding of substrates, herbicides, coenzymes, etc. These sequences are believed to be substantially conserved in all ALS proteins. The residues which are partially conserved in the different ALS proteins may participate in less conserved aspects of enzyme function, such as those which govern its herbicide sensitivity and its end-product inhibition. Examples of this would include the resistance of bacterial isozyme I to sulfometuron methyl and chlorsulfuron, and of bacterial isozyme II to end-product inhibition by valine. Finally, those residues which are not conserved between the proteins probably reside in the framework of the ALS protein where sequence divergence is less disruptive to enzyme function.

Although not wishing to be bound by theory, binding of sulfonylurea herbicides to ALS during acetolactate synthesis is believed to be facilitated by the binding of a first pyruvate molecule to the enzyme. However, the binding of a sulfonylurea herbicide molecule is competitive with the binding of a second pyruvate molecule to the enzyme. Sulfonylurea herbicide sensitivity is conserved through evolution in most ALS enzymes. From these facts, it was deduced that the binding of the sulfonylurea herbicide occurs at or proximal to one or more of the conserved amino acids in the ALS proteins. In fact, Applicant has discovered that substitutions for one or more of 10 specific amino acid residues in one or more of the 7 substantially conserved sub-sequences A through G will confer herbicide resistance and are claimed. It is expected that substitution at other amino acid residues in the substantially conserved sub-sequences will also confer herbicide resistance.

Sulfonylurea herbicide resistance in bacteria, yeast and higher plants, which resistance cosegregates with herbicide-resistant forms of ALS, results from mutations in the structural genes for ALS. Comparing the nucleotide sequences of ALS genes of organisms encoding herbicide sensitive and herbicide-resistant forms of ALS allows one to determine which amino acid residues are important for herbicide inhibition of the enzyme. One mutation in the *E. coli* ilvG gene, which results in an enzyme with increased resistance to sulfometuron methyl inhibition, and with reduced catalytic activity, was determined to result in an alanine-to-valine substitution at position 122 (FIG. 6). Another sulfometuron methyl resistance mutation in this gene was determined to result in a alanine-to-serine substitution at the same position. This alanine residue is conserved in all ALS enzymes except bacterial isozyme I (FIG. 6), which is naturally resistant.

Many genes encoding herbicide-resistant ALS enzymes have been isolated from spontaneous sulfonylurea-resistant yeast mutants. Sequencing of these genes has shown the molecular basis of resistance to be base changes which result in amino acid substitutions at ten different positions in the protein (Table 2), residues 121, 122, 197, 205, 256, 359, 384, 588, 591 and 595 (numbering relative to the positions in FIG. 6).

TABLE 2

| Spontaneous Mutations of the Yeast ALS Gene Resulting in Sulfonylurea Herbicide Resistance | | | | |
|---|---|---|---|---|
| Amino Acid Positions | Wild Type Codon | Wild Type Amino Acid | Mutant Codon | Amino Acid Substitution |
| 121 | GGT | Gly | AGT | Ser |
| 122 | GCT | Ala | CCT | Pro |
| | | | GAT | Asp |
| | | | GTT | Val |
| | | | ACT | Thr |
| 197 | CCA | Pro | TCA | Ser |
| | | | CGA | Arg |
| 205 | GCT | Ala | GAT | Asp |
| | | | ACT | Thr |
| 256 | AAG | Lys | GAG | Glu |
| | | | ACG | Thr |
| | | | AAC | Asn |
| 359 | ATG | Met | GTG | Val |
| 384 | GAC | Asp | GAA | Glu |
| | | | GTC | Val |
| | | | AAC | Asn |
| 588 | GTT | Val | GCT | Ala |
| 591 | TGG | Trp | CGG | Arg |
| | | | AGG | Arg |
| | | | TGT | Cys |
| | | | TGC | Cys |
| | | | GGG | Gly |

TABLE 2-continued

Spontaneous Mutations of the Yeast ALS Gene Resulting in Sulfonylurea Herbicide Resistance

| Amino Acid Positions | Wild Type Codon | Wild Type Amino Acid | Mutant Codon | Amino Acid Substitution |
|---|---|---|---|---|
| | | | TTG | Leu |
| | | | TCG | Ser |
| | | | GCG | Ala |
| 595 | TTC | Phe | TTA | Leu |

At six of these positions, 122, 197, 205, 256, 384 and 591 (Table 2), more than one substitution that confers herbicide resistance has been obtained. At position 122, at which an alanine residue is present in all known wild type ALS enzymes except *E. coli* isozyme I, substitutions of aspartic acid, proline, threonine or valine result in sulfonylurea-resistant ALS. At position 197, at which a proline residue is present in all known wild-type ALS enzymes except *E. coli* isozymes II and III, substitutions of serine or arginine result in sulfonylurea-resistant ALS. At position 205, at which an alanine residue is present in all known wild type ALS enzymes, substitutions of aspartic acid or threonine result in sulfonylurea-resistant ALS. At position 256, at which a lysine residue is present in all known wild type ALS enzymes, substitutions of glutamic acid, asparagine or threonine result in sulfonylurea-resistant ALS. At position 384 at which an aspartic acid is present in all known wild type ALS enzymes, substitutions of glutamic acid, asparagine or valine result in sulfonylurea-resistant ALS. At position 591, at which a tryptophan is present in all known wild type ALB enzymes except *E. coli* isozyme I, substitutions of alanine, cysteine, glycine, leucine, arginine or serine result in sulfonylurea-resistant ALS.

Mutants resistant to sulfonylurea herbicides resulting from single amino acid substitutions at the other four positions, 121, 359, 588 and 595, have been obtained. At position 121, at which glycine is present in all known ALS enzymes, substitution of serine results in a sulfonylurea-resistant ALS. At position 359, at which methionine is present in all known ALS enzymes, substitution of valine results in a sulfonylurea-resistant ALS. At position 588, at which valine is present in all known ALS enzymes, substitution of alanine results in sulfonylurea-resistant ALS. At position 595, at which phenylalanine is present in all known ALS enzymes except *E. coli* isozyme III, substitution of leucine results in sulfonylurea-resistant ALS.

Oligonucleotide-directed site specific mutations, which result in amino acid substitutions at positions 121, 122, 197, 205, 256, 359, 384, 588, 591, and 595 have been made in the yeast gene encoding ALS (Table 3).

TABLE 3

Site Directed Mutations of the Yeast ALS Gene Resulting in Sulfonylurea Herbicide Resistance

| Amino Acid Positions | Wild Type Codon | Wild Type Amino Acid | Mutant Codon | Amino Acid Substitution |
|---|---|---|---|---|
| 121 | GGT | Gly | AAT | Asn |
| | | | GCT | Ala |
| | | | GAT | Asp |
| 122 | GCT | Ala | TCT | Ser |
| | | | GTT | Val |
| | | | ACT | Thr |
| | | | CCT | Pro |
| | | | AAT | Asn |
| | | | ATT | Ile |
| | | | CAT | His |
| | | | CGT | Arg |

TABLE 3-continued

Site Directed Mutations of the Yeast ALS Gene Resulting in Sulfonylurea Herbicide Resistance

| Amino Acid Positions | Wild Type Codon | Wild Type Amino Acid | Mutant Codon | Amino Acid Substitution |
|---|---|---|---|---|
| | | | CTT | Leu |
| | | | TAT | Tyr |
| | | | TGT | Cys |
| | | | TTT | Phe |
| | | | GAA | Glu |
| | | | ATG | Met |
| | | | AAA | Lys |
| | | | CAA | Gln |
| | | | TGG | Trp |
| 197 | CCA | Pro | CAA | Gln |
| | | | GAA | Glu |
| | | | GCA | Ala |
| | | | GGT | Gly |
| | | | TGG | Trp |
| | | | TAC | Tyr |
| | | | TGC | Cys |
| | | | GTT | Val |
| 205 | GCT | Ala | CGT | Arg |
| | | | TGT | Cys |
| | | | GAA | Glu |
| | | | TGG | Trp |
| | | | TAT | Tyr |
| | | | GTT | Val |
| | | | AAT | Asn |
| 256 | AAG | Lys | GAC | Asp |
| | | | CCG | Pro |
| 359 | ATG | Met | CCA | Pro |
| | | | GAG | Glu |
| | | | CAA | Gln |
| | | | AAG | Lys |
| | | | TAT | Tyr |
| | | | TGT | Cys |
| 384 | GAC | Asp | CCA | Pro |
| | | | TGG | Trp |
| | | | TCC | Ser |
| | | | GGT | Gly |
| | | | TGC | Cys |
| 583 | GTT | Val | AGT | Ser |
| | | | AAT | Asn |
| | | | TGG | Trp |
| | | | TGT | Cys |
| 591 | TGG | Trp | GAC | Asp |
| | | | GAG | Glu |
| | | | TTC | Phe |
| | | | CAC | His |
| | | | TAC | Tyr |
| | | | ATA | Ile |
| | | | GTG | Val |
| | | | AAG | Lys |
| | | | ATG | Met |
| | | | AAC | Asn |
| | | | CAG | Gln |
| | | | ACG | Thr |
| 595 | TTC | Phe | GGT | Gly |
| | | | AAC | Asn |
| | | | CGC | Arg |
| | | | TGC | Cys |
| | | | CCA | Pro |
| | | | TCC | Ser |
| | | | TGG | Trp |

At position 122, mutations resulting in eighteen amino acid substitutions for alanins, which is present in wild type ALS, have been made. The nineteenth substitution (aspartic acid) was isolated previously as a spontaneous mutation and was therefore not remade. Each substitution, except for glycine, results in sulfonylurea-resistant ALS. At position 205, mutations resulting in substitutions for alanine, the wild type residue, of cysteine, glutamic acid, arginine, tryptophan, tyrosine, valine or asparagine result in sulfonylurea-resistant ALS. At position 256, mutations resulting in substitutions for lysine, the wild type residue, of aspartic acid or proline result in sulfonylurea-resistant ALS. At position 359, mutations resulting in substitutions for methionine, the wild type residue, of glutamic acid. glutamine, lysine, tyrosine, cysteine or proline result in sulfonylurea-resistant ALS. At position 384, mutations resulting in amino acid substitutions for aspartic acid, the wild type residue, of cysteine, glycine, proline, serine or tryptophan result in sulfonylurea-resistant ALS. At position 591, mutations resulting in amino acid substitutions for tryptophan, the wild type residue, of aspartic acid, glutamic acid, phenylalanine, histidine, isoleucine, lysine, valine, methionine, asparagine, glutamine, threonine or tyrosine result in sulfonylurea-resistant ALS. At position 121, mutations resulting in substitutions for glycine, the wild type residue, of asparagine, alanine or aspartic acid result in sulfonylurea-resistant ALS. At position 197, mutations resulting in substitutions for proline, the wild type residue, of glutamine, glutamic acid, alanine, glycine, tryptophan, tyrosine, cysteine or valine result in sulfonylurea-resistant ALS. At position 583, mutations resulting in substitutions for valine, the wild type residue, of serine, asparagine, tryptophan or cysteine result in sulfonylurea-resistant ALS. At position 595, mutations resulting in substitutions for phenylalanine, the wild type residue, of glycine, asparagine, arginine, cysteine, proline, serine or tryptophan result in sulfonylurea-resistant ALS.

All mutations described in Tables 2 and 3 resulted in enzymes which were active and less inhibited by sulfonylurea herbicides than the wild type. Taken in total these results indicate that most substitutions at these 10 positions result in enzymatically active herbicide resistant ALS.

The deduced amino acid sequences of the wild type ALS proteins from tobacco, Arabidopsis, sugarbeet and corn (partial) are shown in FIG. 7. The amino acid residues at positions 121, 122, 197, 205, 256, 359, 384, 588, 591 and 595 (numbering of positions from FIG. 6) in all the plant enzymes are the same as those present in the wild type herbicide sensitive yeast protein (FIG. 6). The deduced amino acid sequence of the tobacco ALS gene SURB-Hra, which encodes a herbicide-resistant ALS, is shown in FIG. 4. The mutant gene of FIG. 4 was derived from a tissue culture line which had undergone two successive spontaneous mutations. The two mutations have been shown to be genetically linked, and introduction of this fragment into sensitive tobacco cells confers upon the cells the same level of herbicide resistance as is found for the original highly resistant mutant tobacco plant from which the fragment was derived. Based on these facts, it was expected that there would be two amino acid substitutions in the enzyme encoded by the fragment. A comparison of the deduced amino acid sequence of the mutant ALS with the deduced amino acid sequence of the wild type ALS reveals that the mutant ALS has a proline-to-alanine substitution at position 197 (FIG. 6) and a tryptophan-to-leucine substitution at position 591 (FIG. 6). Based on the foregoing, it was determined that substitutions at proline 197 and tryptophan 591 residues confer herbicide resistance. The deduced amino acid sequence of a second mutant tobacco ALS gene, SURA-C3, which encodes a sulfonylurea herbicide resistant ALS, is shown in FIG. 5. A comparison of the deduced amino acid sequences of the mutant and wild type ALS enzymes (FIG. 5 and FIG. 6, line B) reveals that the mutant ALS has a single substitution, proline-to-glutamine, at position 197. The C3 cell line from which the SURA-C3 gene was obtained showed selective herbicide resistance. That is, the C3 mutation conferred resistance to the sulfonylurea herbicides chlorsulfuron and sulfometuron methyl, but not to an imidazolinone herbicide.

The deduced amino acid sequence of a mutant Arabidopsis gene which encodes a sulfonylurea herbicide resistant ALS, is shown in FIG. 10. A comparison of the deduced amino acid sequences of the mutant and wild type ALS enzymes (FIG. 10 and FIG. 6, line C) reveals that the mutant ALS has a single substitution, proline-to-serine, at position 197. This mutation, like the C3 mutation, conferred resistance to the sulfonylurea herbicides chlorsulfuron and sulfometuron methyl, but not to an imidazolinone herbicide. Thus, two different amino acid substitutions for proline at position 197 result in selective herbicide resistance.

The identification of amino acid substitutions in herbicide-resistant ALS enzymes from plants at positions 197, from the C3, Hra and Arabidopsis mutants, and 591 from the Hra mutant, indicates that substitutions at positions operable in yeast ALS are also operable in plant ALS.

While the amino acid residue present at positions 121, 122, 197, 205, 256, 359, 384, 588, 591 and 595 are conserved in all wild type herbicide sensitive ALS enzymes so far characterized from eucaryotes, some substitutions at these positions are found in wild type bacterial ALS enzymes. E. coli isozyme I has a serine rather than alanine at position 122 and a glutamine rather than tryptophan at position 591, E. coli isozyme II has a serine rather than proline at position 197 and E. coli isozyme III has an alanine rather than proline at position 197 and an isoleucine rather than phenylalanine at position 595. Each of these E. coli ALS isozymes is more resistant (from 50-fold to greater than 10,000-fold) to inhibition by (particular) sulfonylurea herbicides than plant or yeast ALS. Furthermore, a site-directed mutation causing a serine-to-proline substitution at position 197 in E. coli ALS II rendered the mutant enzyme 100 fold more sensitive to inhibition, i.e., as sensitive as wild type higher plant enzymes. Thus, proline at position 197 is involved in herbicide binding in E. coli ALS II as well as in yeast and higher plant ALS.

In addition, site-directed mutations which result in tryptophan-to-leucine and glutamine-to-tryptophan substitutions at position 591 in ALS II and ALS I, respectively, of E. coli have been made. The mutation in ALS II makes the enzyme more herbicide resistant than the wild type ALS II, while the mutation in ALS I makes it more sensitive than wild type ALS I.

The site-directed mutations at positions 197 and 591 in ALS I and ALS II of E. coli affect inhibition by herbicide of the mutant enzymes in a manner predicted from the herbicide-resistant mutant yeast and plant ALS proteins. These experimental findings support the universality of the amino acid residues involved in herbicide binding to ALS enzymes from diverse sources.

CHARACTERIZATION OF NUCLEIC ACID FRAGMENTS ENCODING HERBICIDE-RESISTANT ALS

According to the present invention, the amino acid residues of ALS that correspond to $\epsilon_1$ and $\epsilon_2$ in amino acid sub-sequence A, $\alpha_1$ in amino acid sub-sequence B, $\delta_2$ in amino acid sub-sequence C, $\lambda_1$ in amino acid sub-sequence D, $\gamma_1$ in amino acid sub-sequence E, 83, $\beta_7$ and $\beta_8$ in amino acid sub-sequence F and $\sigma_1$ in amino acid sub-sequence G of FIG. 6 (referred to hereinafter as positions 122, 121, 197, 205, 256, 384, 591, 595, 588 and 359 respectively) are important in herbicide sensitivity or resistance of ALS enzymes regardless of the biological source of these enzymes, and any nucleotide sequence encoding a plant ALS can be altered to direct synthesis of a herbicide-resistant ALS by virtue of amino acid substitutions at these residues. The nucleic acid fragment of the present invention is characterized in that at least one of the following conditions is met:

a) The nucleic acid fragment encodes an amino acid other than glycine at position 121. Preferably the amino acid is serine, alanine, asparagine, glutamine, glutamic acid, threonine, or aspartic acid. Most preferably the amino acid is serine, asparagine, alanine or aspartic acid.

b) The nucleic acid fragment encodes an amino acid other than alanine at position 122. Most preferably, the amino acid is any other than glycine.

c) The nucleic acid fragment encodes an amino acid other than proline at position 197. Preferably, the amino acid is alanine, glycine, arginine, tyrosine, tryptophan, serine, valine, cysteine, glutamine, or glutamic acid. Most preferably the amino acid is alanine, serine, arginine, glutamine, glutamic acid, tryptophan or tyrosine.

d) The nucleic acid fragment encodes an amino acid other than alanine at position 205. Preferably, the amino acid is any other than glycine or proline. Most preferably, the amino acid is threonine, cysteine, aspartic acid, glutamic acid, tryptophan, arginine, valine, asparagine or tyrosine.

e) The nucleic acid fragment encodes an amino acid other than lysine at position 256. Preferably, the amino acid is threonine, serine, glutamic acid, aspartic acid, proline, asparagine or glutamine. Most preferably, the amino acid is threonine, glutamic acid, aspartic acid, proline or asparagine.

f) The nucleic acid fragment encodes an amino acid other than methionine at position 359. Preferably, the amino acid is glutamic acid, glutamine, asparagine, aspartic acid, proline, valine, leucine, isoleucine, lysine. arginine, tyrosine, phenylalanine or cysteine. Most preferably the amino acid is glutamic acid, proline, glutamine, lysine, tyrosine, cysteine or valine.

g) The nucleic acid fragment encodes an amino acid other than aspartic acid at position 384. Preferably, the amino acid is glycine, alanine, valine, leucine, isoleucine, serine, threonine, cysteine, glutamic acid, proline, asparagine, glutamine, tryptophan, or histidine. Most preferably, the amino acid is glycine, valine, serine, cysteine, glutamic acid, proline, asparagine or tryptophan.

h) The nucleic acid fragment encodes an amino acid other than valine at position 588. Preferably the amino acid is alanine, serine, threonine, asparagine, glutamine, tryptophan, histidine, cysteine or methionine. Most preferably the amino acid is alanine, serine, asparagine, tryptophan or cysteine.

i) The nucleic acid fragment encodes an amino acid other than tryptophan at position 591. Most preferably, the amino acid is other than proline.

j) The nucleic acid fragment encodes an amino acid other than phenylalanine at position 595. Preferably, the amino acid is any other than tyrosine, aspartic acid or glutamic acid. Most preferably the amino acid is leucine, glycine, proline, serine, asparagine, arginine, tryptophan or cysteine.

In one embodiment, position 121 resides within amino acid sub-sequence A as follows:

PG$\epsilon_2$A wherein P, G and A are as defined above. To confer herbicide resistance, $\epsilon_2$ is an amino acid other than glycine. Most preferably $\epsilon_2$ is the amino acid serine, alanine, asparagine or aspartic acid. This sub-sequence begins about 24 residues from the beginning of a substantially conserved amino acid sequence

HEQ, i.e.,

PG$\epsilon_2$A ... HEQ.

In one embodiment, position 122 resides within amino acid sub-sequence A as follows:

PGG$\epsilon_1$ wherein P and G are as defined above. To confer herbicide resistance $\epsilon_1$ is a natural amino acid other than alanine. Most preferably $\epsilon_1$ is any amino acid except glycane. This sub-sequence begins about 24 residues from the beginning of a substantially conserved amino acid sequence

HEQ, i.e.,

PGG$\epsilon_1$ ... HEQ.

In one embodiment, position 197 resides within amino acid sub-sequence B as follows:

GQV$\alpha_1$ wherein G, Q, and V are as defined above. To confer herbicide resistance $\alpha_1$ is an amino acid other than proline. Most preferably, $\alpha_1$ is alanine, glycine, tyrosine, tryptophan, valine, cysteine, glutamic acid, arginine, serine or glutamine. This sub-sequence begins about 20 residues from the end of one substantially conserved amino acid sequence

SGPGATN and about 55 residues from the beginning of a second substantially conserved amino acid sequence

SGRPGP, i.e.,

SGPGATN ... GQVα₁ ... SGRPGP.

In one embodiment, position 205 resides within an amino acid sub-sequence C as follows:

$IG\delta_1D\delta_2FQE$ wherein I, G, D, F, Q, and E are as defined above, $\delta_1$ represents an amino acid residue which can vary according to the source of the enzyme, but is most commonly T. To confer herbicide resistance $\delta_2$ is an amino acid other than alanine. Most preferably, $\delta_2$ is threonine, cysteine, aspartic acid, glutamic acid, arginine, valine, asparagine, tyrosine or tryptophan. This sub-sequence begins about 5 residues from the end of a substantially conserved amino acid sequence

GQV and about 43 residues from the beginning of a second substantially conserved amino acid sequence

SGRPGP, i.e.,

GQV ... $IG\delta_1D\delta_2FQE$ ... SGRpGp.

In one embodiment, position 256 resides within an amino acid sub-sequence D as follows:

$P\lambda_1D$ wherein P and D are as defined above. To confer herbicide resistance $\lambda_1$ is an amino acid other than lysine. Most preferably, $\lambda_1$, is threonine, glutamic acid, aspartic acid, asparagine or proline. This sub-sequence D begins about 6 residues from the end of a substantially conserved amino acid sequence

SGRPGP i.e.,

SGRPGP ... $p\lambda_1D$.

In one embodiment, position 359 resides within an amino acid sub-sequence G as follows $MLG\sigma_1HG$ wherein M, L, G and H are defined as above. To confer herbicide resistances $\sigma_1$ is an amino acid other than methionine. Most preferably, $\sigma_1$ is proline, glutamine, lysine, tyrosine, cysteine, glutamic acid or valine. This sub-sequence ends about 20 residues from the beginning of a substantially conserved amino acid sequence

RFDDR i.e., $MLG\sigma_1HG$ ... RFDDR.

In one embodiment, position 384 resides within an amino acid sub-sequence G as follows $RFD\gamma_1R$ wherein R, F, and D are as defined above. To confer herbicide resistance, $\gamma_1$ is an amino acid other than aspartic acid. Most preferably, $\gamma_1$ is glycine, valine, cysteine, setine, glutamic acid, proline, asparagine or tryptophan.

This sub-sequence begins about 20 residues from the end of a substantially conserved amino acid sequence

MLGMHG.

i.e.,

MLGMHG ... $RFD\gamma_1R$.

In one embodiment, position 588 resides within an amino acid sub-sequence F as follows $G\beta_1\beta_8\beta_2Q\beta_3\beta_4\beta_5\beta_6\beta_7$ wherein G and Q are defined above, $\beta_1$ to $\beta_8$ will vary depending upon the source of the enzyme. $\beta_1$ is usually methionine, $\beta_3$ is usually tryptophan and $\beta_7$ is usually phenylalanine. To confer herbicide resistance B is an amino acid other than valine. Most preferably $\beta_8$ is alanine, serine, asparagine, tryptophan or cysteane. This sub-sequence begins about 49 residues from the end of a substantially conserved amino acid sequence

GLPAA i.e.,

GLPAA ... $G\beta_1\beta_8\beta_2Q\beta_3\beta_4\beta_5\beta_6\beta_7$.

In one embodiment, position 591 resides within an amino acid sub-sequence F as follows $G\beta_1 V\beta_2Q\beta_3\beta_4\beta_5\beta_6\beta_7$ wherein G, V and Q are defined above, $\beta_1$ to $\beta_7$ will vary depending upon the source of the enzyme. $\beta_1$ is usually methionine and $\beta_7$ is usually phenylalanine. To confer herbicide resistance $\beta_3$ is any amino acid other than tryptophan. Most preferably $\beta_3$ is any amino acid other than proline. This sub-sequence begins about 49 residues from the end of another substantially conserved amino acid sequence

GLPAA, i.e.,

GLPAA ... $G\beta_1V\beta_2q\beta_3\beta_4\beta_5\beta_6\beta_7$.

In one embodiment, position 595 resides within an amino acid sub-sequence F as follows $G\beta_1V\beta_2Q\beta_3\beta_4\beta_5\beta_6\beta_7$ wherein G. V and Q are defined above. $\beta_1$ to $\beta_7$ will vary depending upon the source of the enzyme. $\beta_1$ is usually methionine and $\beta_3$ is usually tryptophan. To confer herbicide resistance, $\beta_7$ is an amino acid other than phenylalanine. Most preferably, $\beta_7$ is leucine, glycine, proline, serine, asparagine, arginine, tryptophan or cysteine. This sub-sequence begins about 49 amino acids from the end of a substantially conserved amino acid sequence

GLPAA i.e.,

GLPAA ... G$\beta_1$V$\beta_2$Q$\beta_3$B$_4$$\beta_5$$\beta_6$$\beta_7$.

Herbicide resistance can be achieved by any one of the above described amino acid substitutions and by combinations thereof.

The precise amino acid substitutions required for herbicide resistance can be achieved by mutating a nucleic acid fragment encoding a herbicide sensitive ALS from any plant of interest generally as follows:
(1) isolate genomic DNA or mRNA from the plant;
(2) prepare a genomic library from the isolated DNA or a cDNA library from the isolated RNA:
(3) identify those phages or plasmids which contain a DNA fragment encoding ALS:
(4) sequence the fragment encoding the ALS;
(5) sub-clone the DNA fragment carrying the ALS gene into a cloning vehicle which is capable of producing single-stranded DNA:
(6) synthesize an oligonucleotide of about 15 to 20 nucleotides which is complementary to a particular ALS nucleotide sequence encoding one of the amino acid sub-sequences recited above except for the nucleotide change(s) required to direct a mutation to a codon for an amino acid selected for its ability to confer herbicide resistance:
(7) anneal the oligonucleotide to the single-stranded DNA containing the region to be mutated and use it to prime synthesis in vitro of a complementary DNA strand forming a heteroduplex;
(8) transform bacterial cells with the heteroduplex DNA;
(9) screen the transformed bacterial cells for those cells which contain the mutated DNA fragment by a) immobilizing the DNA on a nitrocellulose filter, b) hybridizing it to the 5'-$^{32}$P labelled mutagenic oligonucleotide at ambient temperature, and c) washing it under conditions of increasing temperature so as to selectively dissociate the probe from the wild-type gene but not the mutant gene;
(10) isolate a double-stranded DNA fragment containing the mutation from the cells carrying the mutant gene; and
(11) confirm the presence of the mutation by DNA sequence analysis.

An amino acid substitution required for herbicide resistance can also be achieved by substituting a nucleotide sequence of a plant ALS gene which encodes a sequence of amino acids containing the amino acid to be substituted with another nucleotide sequence, which encodes the corresponding stretch of amino acids containing the desired substitution, derived from any natural ALS gene (including microbial) or from a synthetic source.

PREPARATION OF HERBICIDE-RESISTANT PLANTS

The nucleic acid fragments of the present invention can be used to introduce herbicide resistance into plants. In order to introduce a nucleic acid fragment which includes a gene encoding herbicide resistant ALS into different plants, a wide variety of techniques are used depending on the species or cultivar desired. In general, explants or protoplasts can be taken or produced from either in vitro or soil grown plants. Explants or protoplasts may be produced from cotyledons, stems, petioles, leaves, roots, immature embryos, hypocotyds, inflorescences, etc. In theory, any tissue which can be manipulated in vitro to give rise to new callus or organized tissue growth can be used for genetic transformation.

To achieve transformation, explants or protoplasts may be cocultured with Agrobacterium, which can be induced to transfer nucleic acid fragments located between the T-DNA borders of the Ti plasmid to the plant cells. Another method, less commonly used, is direct DNA uptake by plant protoplasts. With this method, the use of Agrobacterium is bypassed and DNA is taken up directly by the protoplasts under the appropriate conditions.

In the examples, a variety of explants from different plants have been cocultured with Agrobacterium to achieve transformation to herbicide resistance. These explants were cultured to permit callus growth. The callus was then tested directly for resistance to sulfonylureas, or plants were regenerated and the plants were tested for sulfonylurea resistance. Testing consisted of an enzyme assay of plant cell extracts for the presence of ALS activity resistant to herbicide and/or growth of plant cells in culture or of whole plants in the presence of normally inhibitory concentrations of herbicide.

The DNA fragments are comprised of a region coding for the synthesis of herbicide-resistant ALS and a region providing for expression of the coding sequence in plants. The 8.3 kb DNA fragment shown in FIG. 2 which codes for the herbicide-resistant ALS protein shown in FIG. 4 contains about 800 bp in the 5' direction (upstream) of the coding region, sufficient for expression of the protein in plants. This DNA fragment can confer resistance to chlorsulfuron up to 2000 ppb in transformed tobacco calluses. Plants regenerated from the transformed cells also show resistance at the whole plant level. The 6.3 kb DNA fragment shown in FIG. 3 which codes for the herbicide resistant ALS protein shown in FIG. 5 contains 2.5 kb in the 5' direction (upstream) and 1.8 kb in the 3' direction (downstream) of the coding region sufficient for expression of the protein in plants. This DNA fragment can confer resistance to chlorsulfuron at 2ppb in transformed tobacco calluses.

The 5.3 kb DNA fragment shown in FIG. 9, which codes for the herbicide resistant ALS protein shown in FIG. 10, contains about 2.5 kb in the 5' direction (upstream) and about 0.8 kb in the 3' direction (downstream) of the coding region sufficient for expression of the protein in plants. This DNA fragment can confer resistance to chlorsulfuron at 30 ppb in transformed tobacco calluses.

In work which is on-going, DNA fragments containing site-directed mutations in the SURA gene that are expected to code for herbicide resistant ALS have been made. These mutations result in the following amino acid substitutions: Ala 122 to Ser, known to be operable in E. coli ALS isozyme II and yeast ALS, Ala 122 to Val, known to be operable in E. coli ALS isozyme II and yeast ALS, Ala 122 to Pro, known to be operable in yeast ALS, Pro 197 to Ser, known to be operable in yeast ALS, and E. coli ALS II enzyme, Pro 197 to Ala, known to be operable in ALS encoded by the SURB-Hra gene of tobacco, Ala 205 to Asp, known to be operable in yeast ALS, Lys 256 to Glu, known to be operable in yeast ALS, Asp 384 to Val, known to be operable in yeast ALS and Trp 591 to Leu, known to be operable in yeast ALS and ALS encoded by the SURB-Hra gene of tobacco. By combining the above mutations, double mutations, resulting in two amino acid substitutions such as Ala 122 to Ser and Pro 197 to Ser, or Ala 122 to Ser and Pro 197 to Ala, or Pro 197 to Ala and Trp 591 to Leu, or Pro 197 to Ser and Trp 591 to Leu have also been made. These mutations were made in a DNA fragment that included only about 180 bp in the 5' direction (upstream) and only about 600 bp in the 3' direction (downstream) of the ALS coding sequence. These DNA fragments were introduced into tobacco by transformation. Herbicide resistance was not expressed in these transformants. The lack of upstream DNA sequences necessary for expression of the mutant ALS genes was thought to be the reason for this. DNA fragments containing several of these in vitro constructed mutations have been inserted into an SURB gene fragment that contains the upstream and downstream DNA sequences necessary for expression. These recombinant DNA fragments were introduced into tobacco by transformation. In this way, the single amino acid substitutions Pro 197 to Ser, Pro 197 to Ala, Ala 205 to Asp, Trp 591 to Leu, and the double amino acid substitutions Pro 197 to Ala, Trp 591 to Leu, and Pro 197 to Ser, Trp 591 to Leu have thus far been shown to confer herbicide resistance in tobacco tissue culture cells. The Ala 205 to Asp mutation had not before been seen in a plant gene encoding herbicide resistant ALS and therefore further demonstrates that substitutions found to be operable in yeast ALS are also operable in plant ALS. The in vitro constructed Pro 197 to Ser and Pro 197 to Ala mutations both confer resistance to the sulfonylurea herbicide chlorsulfuron without affecting sensitivity to an imidazolinone. Thus, three different amino acid substitutions for Pro 197, Ser, Ala and Gln (found in the SURA-C3 encoded protein) confer selective herbicide resistance, suggesting that any substitution at this position will do likewise.

Site directed mutations that are expected to code for herbicide resistant ALS have also been made in the sugarbeet ALS gene. These mutations result in the following amino acid substitutions: Ala 122 to Pro, known to be operable in yeast ALS, Pro 197 to Ala, known to be operable in ALS encoded by the SURB-Hra gene of tobacco, Trp 591 to Leu, known to be operable in yeast ALS and in ALS encoded by the SURB-Hra gene of tobacco and the double mutant, Pro 197 to Ala and Trp 591 to Leu, known to be operable in ALS encoded by the SURB-Hra gene of tobacco. DNA fragments carrying these mutant sugarbeet ALS genes have been introduced into tobacco and sugarbeet cells by transformation. The Pro 197 to Ala and Trp 591 to Leu single amino acid substitutions and the double substitution of Pro 197 to Ala and Trp 591 to Leu conferred resistance to chlorsulfuron in both tobacco and sugarbeets. ALS gene carrying the Ala 122 to Pro substitution did not yield chlorsulfuron resistant transformants. This amino acid substitution has been shown to confer selective herbicide resistance when present in yeast ALS. While the substitution results in resistance to sulfometuron methyl, the mutant enzyme remains sensitive to chlorsulfuron. Thus, it would not be expected to yield chlorsulfuron resistance when present in plant ALS. This type of selective resistance gene represents a particularly useful manifestation of the invention.

The nucleic acid fragments of the invention generally can be introduced into plants directly or in a nucleic acid construct comprising the desired nucleic acid fragment. The nucleic acid construct can be derived from a bacterial plasmid or phage, from the Ti- or Ri-plasmids, from a plant virus or from an autonomously replicating sequence. One preferred means of introducing the nucleic acid fragment into plant cells comprises use of *Agrobacterium tumefaciens* containing the nucleic acid fragment between T-DNA borders either on a disarmed Ti-plasmid (that is, a Ti-plasmid from which the genes for tumorigenicity have been deleted) or in a binary vector in trans to a Ti-plasmid with Vir functions. The Agrobacterium can be used to transform plants by inoculation of tissue explants, such as stems or leaf discs, or by co-cultivation with plant protoplasts. Another preferred means of introducing the present nucleic acid fragment comprises direct introduction of the fragment or a vector containing the fragment into plant protoplasts or cells, with or without the aid of electroporation, polyethylene glycol or other agents or processes known to alter membrane permeability to macromolecules.

The nucleic acid fragments of the invention can be used to transform protoplasts or cell cultures from a wide range of higher plant species to form plant tissue cultures of the present invention. These species include the dicotyledonous plants tobacco, petunia, cotton, sugarbeet, potato, tomato, lettuce, melon, sunflower, soybean, canola (rapeseed) and other Brassica species and poplars; and the monocotyledonous plants corn, wheat, rice, *Lolium multiflorum* and *Asparagus officinalis*. It is expected that all protoplast-derived plant cell lines can be stably transformed with the fragments of the invention.

The nucleic acid fragments of the invention can also be introduced into plant cells with subsequent formation of transformed plants of the present invention. Transformation of whole plants is accomplished in plants whose cells can be transformed by foreign genes at a stage from which whole plants can be regenerated. In the present invention, transformed plants are monocotyledonous and dicotyledonous plants. Preferably, the transformed plants are selected from the group consisting of tobacco, petunia, cotton, sugarbeets, potato, tomato, lettuce, sunflower, soybean, canola and other Brassica species, poplars, alfalfa, clover, sugarcane, barley, oats and millets: see "Handbook of Plant Cell Culture" Vols. 1–3, Evans, D. A. et al., Sharp et al., and Ammirato et al., respectively, MacMillan, N.Y. (1983, 84). Most preferably, the transformed plants are selected from the group consisting of tobacco, petunia, potato, tomato, sunflower, sugarbeet, alfalfa, lettuce or Brassica species. The range of crop species in which foreign genes can be introduced is expected to increase rapidly as tissue culture and transformation methods improve and as selectable markers such as the fragments of the invention (see discussion below) become available.

One could further increase the level of expression of the nucleic acid fragments of the invention by replacing their native regulatory nucleotide sequences, 5' and 3' to the ALS coding sequence, with synthetic or natural sequences known to provide high level and/or tissue specific expression. One may also substitute the nucleotide sequences of the nucleic acid fragments of the invention with other synthetic or natural sequences which encode transit peptides which will allow efficient chloroplast uptake of the nucleic acid fragments of the invention.

The nucleic acid fragments of the present invention also have utility as selectable markers for both plant genetic studies and plant cell transformations. A gene of interests generally conferring some agronomically useful trait, e.g. disease resistance, can be introduced into a population of sensitive plant cells physically linked to a nucleic acid fragment of the present invention. Cells can then be grown in a medium containing a herbicide to which the ALS encoded by a fragment of the invention is resistant. The surviving (transformed) cells are presumed to have acquired not only the herbicide resistance phenotype, but also the phenotype conferred by the gene of interest. The nucleic acid fragments can be introduced by cloning vehicles, such as phages and plasmids, plant viruses, and by direct nucleic acid introduction. Subsequently, in a plant breeding program, the agronomically useful trait can be introduced into various cultivars through standard genetic crosses, by following the easily assayed herbicide resistance phenotype associated with the linked selectable genetic marker.

Transformed plants of the present invention are resistant to many of the sulfonylurea, triazolopyrimidine sulfonamide and imidazolinone herbicides. These herbicides are disclosed in the following patents and published patent applications as follows:

Sulfonylureas

| | |
|---|---|
| U.S. Pat. No. 4,127,405 | U.S. Pat. No. 4,383,113 |
| U.S. Pat. No. 4,169,719 | U.S. Pat. No. 4,394,153 |
| U.S. Pat. No. 4,190,432 | U.S. Pat. No. 4,394,506 |
| U.S. Pat. No. 4,214,890 | U.S. Pat. No. 4,420,325 |
| U.S. Pat. No. 4,225,337 | U.S. Pat. No. 4,452,628 |
| U.S. Pat. No. 4,231,784 | U.S. Pat. No. 4,481,029 |
| U.S. Pat. No. 4,257,802 | U.S. Pat. No. 4,586,950 |
| U.S. Pat. No. 4,310,346 | U.S. Pat. No. 4,435,206 |
| U.S. Pat. No. 4,544,401 | U.S. Pat. No. 4,514,212 |
| U.S. Pat. No. 4,435,206 | U.S. Pat. No. 4,634,465 |
| | EP-A-204,513 |

Triazolopyrimidine sulfonamides

South African Application 84/8844 (published 5/14/85)

Imidazolinones

U.S. Pat. No. 4,188,487
EP-A-41,623 (published Dec. 16, 1981)

The nucleic acid fragments of the present invention encode ALS which is resistant to the following sulfonylurea herbicides:

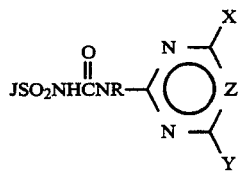

wherein
R is H or $CH_3$;
J is

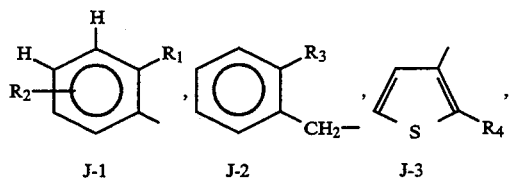

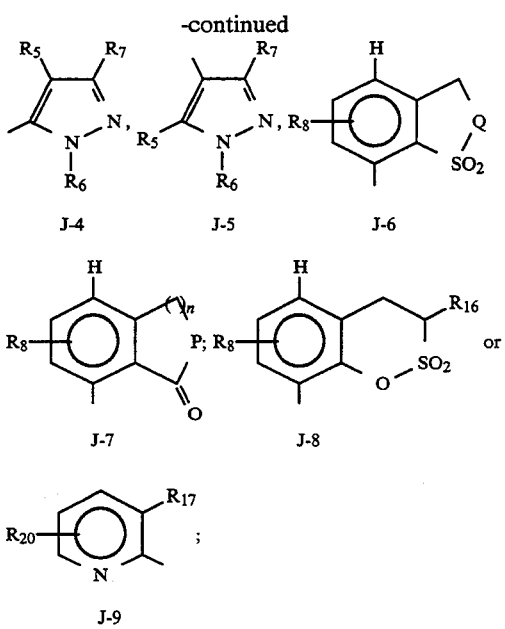

$R_1$ is Cl, Br, $NO_2$, $C_1$–$C_4$ alkyl, $C_2$–$C_4$ alkenyl, $CF_3$, $C_1$–$C_4$ alkoxy, $C_1$–$C_4$ haloalkoxy, $C_3$–$C_4$ alkenyloxy, $C_2$–$C_4$ haloalkenyloxy, $C_3$–$C_4$ alkynyloxy, $CO_2R_9$, $CONR_{10}R_{11}$, $S(O)_mR_{12}$, $OSO_2R_{12}$, phenyl, $SO_2N(OCH_3)CH_3$, $SO_2NR_{10}R_{11}$.

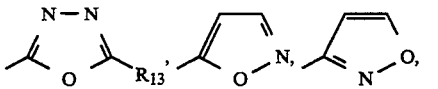

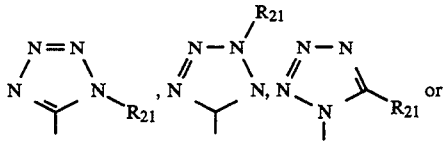

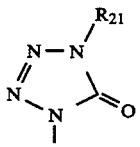

$R_2$ is H, Cl, Br, F, $CH_3$, $NO_2$, $SCH_3$, $OCF_2H$, $OCH_2CF_3$ or $OCH_3$;
$R_3$ is Cl, $NO_2$, $CO_2CH_3$, $CO_2C_2H_5$; $SO_2N(CH_3)_2$, $SO_2CH_3$ or $SO_2C_2H_5$;
$R_4$ is $C_1$–$C_3$ alkyl, Cl, Br, $NO_2$, $CO_2R_9$, $CON(CH_3)_2$, $SO_2N(CH_3)_2$, $SO_2N(OCH_3)CH_3$ or $S(O)_mR_{12}$;
$R_5$ is $C_1$–$C_3$ alkyl, $C_4$–$C_5$ cycloalkylcarbonyl, F, Cl, Br, $NO_2$, $CO_2R_{14}$, $SO_2N(CH_3)_2$, $SO_2R_{12}$ or phenyl;
$R_6$ is H, $C_1$–$C_3$ alkyl, or $CH_2CH=CH_2$;
$R_7$ is H, $CH_3$, $OCH_3$, Cl or Br;
$R_8$ as H, F, Cl, Br, $CH_3$, $OCH_3$, $CF_3$, $SCH_3$ or $OCF_2H$;
$R_9$ is $C_1$–$C_4$ alkyl, $C_3$–$C_4$ alkenyl or $CH_2CH_2Cl$;
$R_{10}$ is H or $C_1$–$C_3$ alkyl;
$R_{11}$ is H or $C_1$–$C_2$ alkyl;
$R_{12}$ is $C_1$–$C_3$ alkyl;
$R_{13}$ is H or $CH_3$;

$R_{14}$ is $C_1$–$C_3$ alkyl or $CH_2CH=CH_2$;
m is 0, 1 or 2;
n is 1 or 2;
Q is $CH_2$, $CHCH_3$ or $NR_{15}$;
$R_{15}$ is H or $C_1$–$C_4$ alkyl;
P is O or $CH_2$;
$R_{16}$ is H or $CH_3$;
$R_{17}$ is $C(O)NR_{18}R_{19}$;
$R_{18}$ is H or $CH_3$;
$R_{19}$ is $CH_3$;
$R_{20}$ is H, Cl, F, Br, $CH_3$, $CF_3$, $OCH_3$ or $OCF_2H$;
$R_{21}$ is H or $CH_3$;
X is $CH_3$, $OCH_3$, $OC_2H_5$ or $NHCH_3$;
Y is $CH_3$, $C_2H_5$, $OCH_3$, $OC_2H_5$, $OCF_2H$, $OCH_2CF_3$, Cl, $CH_2OCH_3$ or cyclopropyl;
Z is CH or N;
and their agriculturally suitable salts; provided that
a) when Y is Cl, then Z is CH and X is $OCH_3$;
b) when Y is $OCF_2H$, then Z is CH;
c) when J is J-1 and $R_1$ is $OSO_2R_{12}$ or phenyl, then Y is other than $OCF_2H$;
d) when J is J-2, then Y is other than $OCF_2H$ or $OCH_2CF_3$; and
e) when J is J-3 and $R_4$ is $S(O)_mR_{12}$, then Y is other than $OCH_2CF_3$.

Sulfonylurea herbicides to which the ALS is particularly resistant include
1) Compounds of Formula I where
J is J-1;
$R_1$ is Cl, $CH_3$, $C_1$–$C_4$ alkoxy, $C_1$–$C_2$ haloalkoxy, allyloxy, propargyloxy, $CO_2R_9$, $CONR_{10}R_{11}$, $SO_2N(OCH_3)CH_3$, $SO_2NR_{10}R_{11}$, $S(O)_mR_{12}$, $OSO_2R_{12}$, phenyl or

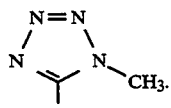

2) Compounds of Formula I where
J is J-2;
R is H; and
$R_3$ is $SO_2N(CH_3)_2$, $CO_2CH_3$ or $CO_2C_2H_5$.
3) Compounds of Formula I where
J is J-3
R is H; and
$R_4$ is $CO_2CH_3$ or $CO_2C_2H_5$;
4) Compounds of Formula I where
J is J-4;
R is H;
$R_5$ is Cl, Br, $CO_2CH_3$, $CO_2C_2H_5$ or

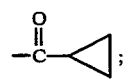

$R_6$ is $CH_3$; and
$R_7$ is H, Cl or $OCH_3$.
5) Compounds of Formula I where
J is J-5;
R is H;
$R_5$ is $CO_2CH_3$ or $CO_2C_2H_5$; and
$R_7$ is H or $CH_3$.
6) Compounds of Formula I where
J is J-6;
Q is $CHCH_3$ or $NR_{15}$;
R is H; and
$R_8$ is H, F, Cl, $CH_3$, $OCH_3$, $CF_3$ or $SCH_3$.
7) Compounds of Formula I where
J is J-7;
R is H:
P is O; and
$R_8$ is H, F, Cl, $CH_3$, $OCH_3$, $CF_3$ or $SCH_3$.
8) Compounds of Formula I where
J is J-8;
R is H;
$R_{16}$ is $CH_3$; and
$R_8$ is H, F, Cl, $CH_3$, $OCH_3$, $CF_3$ or $SCH_3$.
9) Compounds of Formula I where
J is J-9;
R is H; and
$R_{17}$ is $C(O)N(CH_3)_2$.
10) Compounds of Formula I where
R is H;
$R_1$ is Cl, $C_1$–$C_4$ alkoxy, $OCF_2H$, $OCH_2CH_2Cl$, $CO_2R_9$, $CON(CH_3)_2$, $SO_2N(CH_3)_2$, $SO_2R_{12}$ or $OSO_2R_{12}$; and
$R_2$ is H, Cl, $CH_3$, or $OCH_3$.

The nucleic acid fragments of the present invention encode ALS which is resistant to the following triazolopyrimidine sulfonamides:

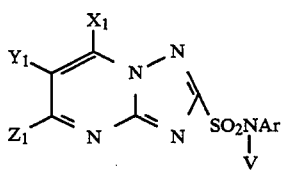

wherein
Ar is

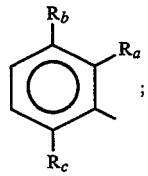

$R_a$ is $C_1$–$C_4$ alkyl, F, Cl, Br, I, $NO_2$, $S(O)_pR_d$, $COOR_e$ or $CF_3$;
$R_b$ is H, F, Cl, Br, I, $C_1$–$C_4$ alkyl or $COOR_e$;
$R_c$ is H, $C_1$–$C_4$ alkyl, F, Cl, Br, I, $CH_2OR_d$, phenyl, $NO_2$ or $COOR_e$;
$R_d$ is $C_1$–$C_4$ alkyl;
$R_e$ is $C_1$–$C_4$ alkyl, $C_1$–$C_4$ alkenyl, $C_1$–$C_4$ alkynyl, or 2-ethoxyethyl;
V is H, $C_1$–$C_3$ alkyl, allyl, propargyl, benzyl or $C_1$–$C_3$ alkylcarbonyl;
$X_1$, $Y_1$, and $Z_1$, are independently H, F, Cl, Br, I, $C_1$–$C_4$ alkyl $C_1$–$C_2$ alkylthio or $C_1$–$C_4$ alkoxy; and
p is 0, 1 or 2.

Triazolopyrimidinesulfonamide herbicides to which the ALS is particularly resistant include
1) Compounds of Formula II where V is H.
2) Compounds of Preferred 1 where
$X_1$ is H or $CH_3$:
$Y_1$ is H;
$Z_1$ is $CH_3$; and $R_a$ and $R_c$ are not simultaneously H.

The nucleic acid fragments of the present invention encode ALS which is resistant to the following imidazolinones:

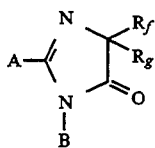

wherein
A is

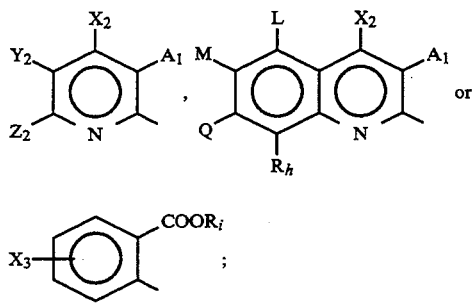

$R_f$ is $C_1$–$C_4$ alkyl;
$R_g$ is $C_1$–$C_4$ alkyl or $C_3$–$C_6$ cycloalkyl;
$A_1$ is $COOR_i$, $CH_2OH$ or $CHO$;
$R_i$ is H; $C_1$–$C_{12}$ alkyl optionally substituted by $C_1$–$C_3$ alkyl, $C_3$–$C_6$ cycloalkyl or phenyl; $C_3$–$C_5$ alkenyl optionally substituted by phenyl or 1–2 $C_1$–$C_3$ alkyl, F, Cl, Br or I; or $C_3$–$C_5$ alkynyl optionally substituted by phenyl or 1–2 $C_1$–$C_3$ alkyl, F, Cl, Br or I;
B is H; $C(O)C_1$–$C_6$ alkyl or C(O)phenyl optionally substituted by Cl, $NO_2$ or $OCH_3$;
$X_2$ is H, F, Cl, Br, I, OH or $CH_3$;
$Y_2$ and $Z_2$ are independently H, $C_1$–$C_6$ alkyl, $C_1$–$C_6$ alkoxy, F, Cl, Br, I, phenyl, $NO_2$, CN, $CF_3$ or $SO_2CH_3$;
$X_3$ is H, $C_1$–$C_3$ alkyl, F, Cl, Br, I or $NO_2$; and
L, M, Q and $R_h$ are independently H, F, Cl, Br, I, $CH_3$, $OCH_3$, $NO_2$, $CF_3$, CN, $N(CH_3)_2$, $NH_2$, $SCH_3$ or $SG_2CH_3$ provided that only one of M or Q may be a substituent other than H, F, Cl, Br, I, $CH_3$ or $OCH_3$.

Imidazolinone herbicides to which the ALS is particularly resistant include
1) Compounds of Formula III where
   B is H; and
   $A_1$ is $COOR_i$.
2) Compounds of Preferred 1 where
   $R_f$ is $CH_3$;
   $R_g$ is $CH(CH_3)_2$;
   $X_2$ is H;
   $Y_2$ is H, $C_1$–$C_3$ alkyl or $OCH_3$;
   $Z_2$ is H;
   $X_3$ is H, $CH_3$, Cl or $NO_2$; and
   L, M, Q and $R_h$ are H.

Any of the aforementioned compounds may be applied alone or in combination to the site, pre- and/or post-emergence. Because the crop plant itself is resistant to the herbicide s), the spectrum of herbicide activity can be chosen for its efficacy in controlling the unwanted vegetation.

The present invention is further defined in the following Examples, in which all parts and percentages are by weight and degrees are Celsius; unless otherwise stated. It should be understood that these examples, while indicating preferred embodiments of the invention, are given by way of illustration only. From the above disclosure and these examples one skilled in the art can ascertain the essential characteristics of this invention, and without departing from the spirit and scope thereof, can make various changes and modifications of the invention to adapt it to various usages and conditions.

EXAMPLE I

Tobacco (*Nicotiana tabacum* cv. Xanthi) DNA from the Hra mutant was made according to the procedure of Dunsmuir et al. (*J. Mol. App. Genetics*, 1983, 2, 285). 2×13 g of 1–2 inch tobacco leaves were removed from plants and immediately ground in 2×20 mL buffer A (10 mM Tricine-KOH pH 7.6–1.14M sucrose—5 mMMgCl₂—5 mM 2-mercaptoethanol) in the cold room, using mortars and pestles. An additional 40–50 mL of buffer A was added, and the slurries were filtered through 16 layers of cheesecloth. The filtrates were centrifuged at 2500 rpm in a Sorvall GSA rotor at 4° C. for 5 minutes. The pellets were resuspended in 10 mL buffer A, another 100 mL of buffer A was mixed in, and the cells were centrifuged as above. The pellets were then resuspended in 100 mL buffer A +0.4% Triton X-100, and left on ice for 10 minutes, and centrifuged as above. The pellets were washed twice more in the latter buffer. The final pellets were resuspended in 5 mL of resuspension buffer (50 mM Tris HCl pH 8, 20 mM EDTA), 1 mL of resuspension buffer—10% sarkosyl was added, and the volumes were then adjusted to 10 mL with resuspension buffer. Proteinase K was added to 100 μg/mL to the lysates, and the lysates were digested at 37° C. overnight. The lysates were then brought to a density of 1.55 g/mL CsCl, and to a final concentration of 300 pg/mL ethidium bromide. The solutions were centrifuged in a Beckman Ti70.1 rotor at 40000 rpm at 15° C. for 24 hours, and the fluorescent DNA band was removed after visualization with longwave UV light. To remove the DNA, holes were punched in the sides of the polyallomer tubes with an 18 gauge needle, and the viscous DNA was allowed to drip into collection tubes. Great care was taken at all stages after cell lysis to prevent shearing of the DNA. The DNA was again gently resuspended in a CsCl solution of 1.55 g/mL density and 300 μg/mL ethidium bromide, and centrifuged at 40000 rpm at 15° C. for 48 hours, in a Sorvall TFT65.13 rotor. The DNA was again collected by side puncture of the tube. It was gently extracted 10 times with TE (10 mM Tris HCl pH 8, 1 mM EDTA) saturated-isoamyl alcohol, and then dialyzed extensively against TE.

The standard techniques of recombinant DNA and molecular cloning used here are described in R. W. Davis. D. Borsrein and J. R. Roth, Advanced Bacterial Genetics, Cold Spring Harbor Laboratory, Cold Spring Harbor, N.Y. (1980) and T. Maniatis, E. F. Fritsch and Sambrook, *Molecular Cloning: A Laboratory Manual*, Cold Spring Harbor Laboratory. Cold Spring Harbor, N.Y. (1982).

A tobacco DNA library was constructed following the procedures of Maniatis et al (see above). Tobacco DNA was digested with the restriction enzyme Sau 3A to give a majority of fragments in the 20 kilobase size range, as assayed by agarose gel electrophoresis. The fragments were loaded onto 10–40% sucrose (in 1M NaCl, 20 mM Tris pH 8, 1 mM EDTA) gradients and size-fractionated by centrifugation in a Beckman SW 28 rotor at 26000 rpm at 17° C. for 16 hours. Fractions from the sucrose gradients were collected and analyzed by agarose gel electrophoresis, and fractions containing fragments in the 20 kilobase size range were dialyzed against TE and ethanol precipitated. They were then ligated to BamH I cut phage lambda EMBL3 arms, at a 2:1 molar ratio, and packaged into lambda phage heads, following the instructions supplied by the manufacturer of the lambda arms and packaging reactions (Stratagene Cloning Systems, San Diego, Calif.).

A tobacco DNA library of 400000 phage was plated on the host strain E. coli LE 392 (Silhavy, T. J., Berman, M. L. and Enquist, L. W. (1984), "Experiments with Gene Fusions," Cold Spring Harbor Laboratory, Cold Spring Harbor, N.Y.) at a density of 50000 phage per 150 mm Petri dish, on 10 plates. Duplicate nitrocellulose filter lifts of the phage plaques were made according to the procedure of Maniatis et al., and were hybridized with $^{32}$P-labeled probes carrying either 5' or 3' ALS gene fragments produced in a riboprobe labeling system. Riboprobes were synthesized according to the procedures accompanying the riboprobe kit sold by Promega Biotech (Madison, Wis.). Plaques that gave positive signals on films from both sets of filters were picked and the purification process was reiterated, until well-isolated hybridizing plaques were obtained.

Minipreps of the DNA from plaque purified phage were analyzed by restriction enzyme digestions. Two classes of cloned tobacco DNA fragment inserts were distinguished as shown if FIG. 1. Phages 1, 2, 17 and 18 contained inserts related to the previously isolated ALS gene from the SURA locus, encoding herbicide sensitive ALS. Phage 3 contained an insert distinct from the above which was expected to contain the SURB-Hra gene encoding herbicide resistant ALS. EcoR I fragments that encompassed the hybridizing regions of phage 3 were subcloned into M13 phage vectors and subjected to DNA sequence analysis, using oligonucleotides to extend the sequenced regions in overlapping segments. A single open reading frame of 1992 nucleotides was found, and was identified as an ALS gene by comparison of the deduced amino acid sequence with conserved regions of the amino acid sequences of ALS proteins from other species.

ALS genes isolated from the herbicide-resistant mutant tobacco, Hra, were introduced into sensitive tobacco cells via the "binary vector" system employing *Agrobacterium tumefaciens*. The ALS genes were first introduced into a binary vector in *A. tumefaciens* via plasmid conjugation, and the engineered *A. tumefaciens* were then used to transform plant cells with the foreign genes via co-cultivation.

A) Introduction of the Isolated Tobacco ALS Genes into *A. tumefaciens*:

i) Construction of Binary Vectors: The standard techniques of recombinant DNA and molecular cloning used here are described in R. W. Davis, D. Borsrein and J. R. Roth, *Advanced Bacterial Genetics*, Cold Spring Harbor Laboratory, Cold Spring Harbor, N.Y. (1980) and T. Maniatis, E. F. Fritsch and Sambrook, *Molecular Cloning:A Laboratory Manual*, Cold Spring Harbor Laboratory, Cold Spring Harbor, N.Y. (1982). The purified 8.3 kilobase Spe I nucleic acid fragment of the invention, which was isolated from the Hra tobacco mutant and which contains a coding sequence for a herbicide-resistant form of an ALS gene, was inserted into the Xba I site of the plasmid vector pMuc19 (J. D. G. Jones, P. Dunsmiur and J. Bedbrook, EMBO Journal 4:2411–2418 (1985)). (Although, Spe I and Xba I restriction enzymes recognize different DNA sequences, the products of these digestions carry the same 5' overhanging sequence). The orientation of the insert fragment in one of the resultant plasmids, pAGS148, was determined by restriction enzyme analyses (FIG. 2).

The binary vector pAGS135 was used to move plasmid pAGS148 into *A. tumefaciens*. Plasmid pAGS135 is derived from plasmid pAGS112 (P. Van den Elzen, K. Y. Lee, J. Townsend and J. Bedbrook, *Plant Mol. Biol.*, 5:149–154 (1985)) by digestion of plasmid pAGS112 DNA with Xho I restriction endonuclease, treatment with the Klenow fragment of *E. coli* DNA polymerase I, and self-ligation of the DNA which effects the removal of the Xho I site outside the T-DNA right border. Plasmid pAGS112 is derived from the wide-host range vector pLAFR (A. M. Friedman, S. R. Long, S. E. Brown, S. E. Buikema and F. M. Ausubel, *Gene*, 18:289–296 (1982)) by the insertion into pLAFR of an EcoR I fragment in which the T-DNA borders flank a gene for expressing kanamycin resistance in plants and a unique BamH I site for cloning (Van den Elzen st. al., *Plant Mol. Biol.*, 5:149–154 (1985)). CsCl purified plasmids pAGS148 and pAGS135 were digested with BamH I, and the resultant BamH I-cleaved plasmids were ligated. The ligation mixtures were packaged into lambda phage particles in vitro and used to infect *Escherichia coli* strain HB$_{101}$. Transformants were selected on ampicillin. The physical map of a recombinant plasmid, pAGS152, from one of the transformants was determined by restriction analyses and is shown in FIG. 2.

ii) Conjugation of Plasmid pAGS152 from *E. coli* into *A. tumefaciens*: Plasmid pAGS152 was introduced into *A. tumefaciens* by conjugation essentially by the three-way mating method of Ruvkun, G. and Ausubel, F. M., *Nature*, 289:85–88 (1981). *E. coli* strain HB$_{101}$ harboring plasmid pAGS152 and *E. coli* strain HB$_{101}$ harboring the mobilizing vector pRK2013 (ATCC 37159) (D. Figurski and D. R. Helinski, *Proc. Natl. Acad. Sci U.S.A.*, 76:1648–1652 (1979)) were mixed with *A. tumefaciens* strain LBA4404 harboring plasmid pAL4404 (A. Hoekema, P. R. Hirsch, P. J. J. Hooykaas and R. A. Schilperoort, *Nature*, 303:179–180 (1983)) and allowed to mate on solid LB medium (J. H. Miller, *Experiments in Molecular Genetics*, Cold Spring Harbor Laboratory, Cold Spring Harbor, N.Y. (1972)) at 28° C. for 16 hours. Transconjugants were selected on plates containing rifampicin at 100 mg/liter and tetracycline at 1 mg/liter. *A. tumefaciens* LBA4404:pAGS152 was restreaked on minimal A medium containing tetracycline at 1 mg/liter.

Essentially, a similar method was used to obtain both *A. tumefaciens* LBA4404 containing plasmid pAGS112, the binary vector without any plant nucleic acid fragment insert, and *A. tumefaciens* LBA4404 containing plasmid pAGS145, the binary vector containing a nucleic acid fragment from phage clone 1. The latter fragment was also isolated from Hra mutant tobacco plants and carries a gene for a herbicide-sensitive form of ALS; this gene is not the wild type allele of the gene for the herbicide-resistant ALS in the nucleic acid fragment of the invention but the SURA gene from the second genetic locus.

B) Introduction of the Isolated ALS Genes Into Sensitive Tobacco by Co-cultivation of the Plant Cells with *A. tumefaciens* LBA4404 (pAGS145) and LBA4404 (pAGS152).

All manipulations of sterile media and plant materials were done in laminar flow hoods, under suitable containment. Plant growth and plant cell cultures were carried out at 27° C. All protoplast manipulations were carried out at room temperature unless otherwise mentioned.

Day 1 (afternoon):

Protoplast isolation medium was prepared by adding the following to K3/S(1) Medium: 0.1% (w/v) of MES buffer (Sigma Chemical Co.), 1% (w/v) of Cellulase (Onozuka or Cellulysin), and 0.1% of Macerase (Onozuka). After gentle stirring for approximately 30 minutes, the pH was brought to 5.6 with KOH and the medium was filter-sterized.

Sterile tobacco (Nicotiana tabacum vat. Wisconsin 38) plants were cultured from 1 cm apical or auxiliary explants on OMS Medium in Magenta Boxes under a cycle of a 16 hour light period (6,000–8,000 lux) followed by an 8 hour dark period. When the plants were 5–7 weeks old, fully expanded leaves (3–6 leaves down from the apex) were removed, and two leaves each were placed, top surface down, on 20 mL of protoplast isolation medium in a 100×25 mm petri dish. The leaves were then submerged and finely divided with a sharp surgical blade. The midrib was held and the cuts were made outward from it towards the deaf margin at approximately 2 mm intervals. The petri dishes were then sealed with parafilm and the macerated tissue incubated overnight (14–17 hours) in darkness at 27°–29° C. with gentle gyrotory agitation (20–25 rpm).

Day 2 (morning):

A 75 mm filtering funnel, lined with four layers of cheesecloth, was clamped to a ringstand. A glass tube (approximately 15 cm long and with an outer diameter of <5 mm) was attached to the funnel with latex tubing. The funnel, cheesecloth, latex and glass tubing were wrapped in aluminum foil and sterilized in an autoclave as a unit.

The glass tubing was placed in a Babcock bottle, and the cheesecloth was wetted with K3/S(1) Medium. The digested leaf tissue from two petri dishes was carefully poured into the funnel. The cheesecloth was rinsed and expressed into the bottle. The loaded bottles were topped with K3/S(1) Medium, covered with foil and centrifuged at approximately 100×g for 10 minutes. The floating protoplasts (1–2 mL) were collected with a 1 mL serological pipette and placed in 20 mL of K3/S(1) Medium in another Babcock bottle. After resuspending the protoplasts by gently swirling, the Babcock bottles were topped and centrifuged as before. The floating protoplasts (1–2 mL) were collected as described above and placed in 30 mL of K3/G(1) Medium. The protoplasts were counted in a hemacytometer, and the volume was adjusted to give $1\times 10^{+5}$ protoplasts/mL. 5 mL aliquots of the protoplasts were plated in petri dishes [100×20 mm tissue-culture petri dishes (Corning); these dishes were used in all subsequent protoplast manipulations] and cultured in darkness.

Day 2 (afternoon):

A single colony of A. tumefaciens, containing the desired plant transformation vector, viz., pAGS112 (plasmid vector above), pAGS152 (containing the nucleic acid fragment of the present invention) or pAGS145 (containing a nucleic acid encoding a sensitive form of ALS), growing on a Minimal A plate was inoculated into 5 mL of Minimal A Medium in an 18 mm test tube and cultured overnight on a roller drum at 40–60 rpm at 27°–28° C.

Day 3 (morning):

The optical density of the A. tumefaciens cultures was measured at 550 nm and adjusted to 0.15 with Minimal A Medium, and the bacteria were allowed to continue growing as described above.

Day 3 (afternoon):

When the optical density (at 550 nm) of the A. tumefaciens cultures was 0.6 (log phase culture), approximately 6 hours after dilution, the bacteria were added to plant cells at a multiplicity of approximately 50 bacteria/plant cell (an optical density of 1.0 at 550 nm = $1.4\times 10^9$ bacteria). The bacteria and plant cell mixture was co-cultivated for 66 hours at 24° C. in low light (approximately 500 lux). Non-transformed protoplast controls were incubated similarly, but without agrobacteria. The following protocol is carried out for each co-cultivation (transformed cells with different agrobacteria, as well as non-transformed cells).

Day 6 (morning):

Co-cultivation was terminated by adding 20 mL of a 1:1 mixture of K3/G(2) Medium:C Medium supplemented with 500 mg/liter of cefotaxime (to select against the agrobacteria) to 5 mL of the co-cultivation mixture. The co-cultivated cells were gently and thoroughly resuspended in the new medium by mixing with a 5 or 10 mL serological pipette. The cell density was $2\times 10^4$ protoplast equivalents/mL (protoplast equivalents = initial protoplasts, assuming 100% recovery and cell survival) and the osmiticum was 0.35M. Three 5 mL aliquots of each culture were dispensed into fresh petri dishes.

From this juncture until the cells were embedded in solid medium, the cells were cultured in low light (500–1500 lux) without motion and were aseptically transferred to different media. At the indicated times, cells from one plate of each culture were transferred to non-selective media, while cells from the other two plates of each culture were transferred to selective media containing either 50 mg/liter of kanamycin or 2 ng/mL chlorsulfuron in order to select for transformed plant cells. For these transfers, the contents of each plate were collected with a 5 mL serological pipette, placed in separate 15 mL polystyrene conical centrifuge tubes and centrifuged at approximately 50×g for 5–10 minutes. The supernatant fluid was removed with a pipette without disrupting the loose pellet. Pellets of co-cultivated cells from each plate were then gently resuspended in the appropriate fresh medium.

Day 10:

The cells were transferred into 5 mL of C Medium supplemented with 500 mg/liter cefotaxime in the case of non-selected plant cells or with 500 mg/liter cefotaxime and either 50 mg/liter of kanamycin or 2 ng/mL chlorsulfuron in the case of selected cells. Each of these cultures was returned to the petri dishes from which they were taken; in this way not all cells needed to be pelleted to effect a medium exchange with minimal cell loss.

Day 13:

Non-selected cells were transferred to 20 mL of a 3:1 mixture of C Medium:MSP Medium supplemented with 500 mg/liter of cefotaxime, and a 5 mL aliquot was dispensed into a fresh petri dish (at a density of $5\times 10^3$ protoplast equivalents/mL). The selected cells were resuspended in 5 mL of a 3:1 mixture of C Medium:MSP Medium supplemented with 500 mg/liter cefotaxime and 50 mg/liter kanamycin or 2 ng/mL chlorsulfuron and returned to the original plates for further culture.

Day 16–17:

The cells were transferred to 5 mL of a 1:1 mixture of C Medium and MSP Medium supplemented with 500 mg/liter cefotaxime alone (in the case of non-selected plant cells) or with 500 mg/liter cefotaxime and either 50 mg/liter of kanamycin or 2 ng/mL chlorsulfuron (in the case of selected cells) and cultured as before.

Day 20:

The non-selected cells were transferred to 25 mL of 1:1 mixture of C Medium:MSP Medium, and the mixture added to 25 mL of a 1:1 mixture of a 2×MSP Medium and 1% (w/v) type VII agarose solution (50° C.). The resultant culture was mixed quickly with a 25 mL wide-mouth serological pipette and dispensed in 5 mL aliquots into fresh petri dishes. The suspended micro calluses in the agar solution were spread carefully and evenly across the plates with agitation by hand. The plates were covered and left in the hood for one hour to solidify before they were wrapped in parafilm and removed to the culture chamber. The cell density was about $5 \times 10^2$ protoplasts equivalents/mL and the osmoticum was 0.15M. The embedded cells were counted on a colony counter approximately 10 days later (Tables 1 and 2, below).

The selected cells were transferred to 20 mL of a 1:3 mixture of C Medium:MSP Medium containing 50 mg/liter of kanamycin or 2 ng/mL chlorsulfuron. Five mL aliquots of the resuspended cultures ($5 \times 10^{+3}$ protoplast equivalents/mL) were dispensed into four fresh petri dishes per selected culture and cultured as before.

Day 23–24:

Each 5 mL culture of the selected cells was diluted with 7.5 mL of MSP Medium supplemented with 50 mg/liter of kanamycin or 2 ng/mL chlorsulfuron in order to achieve a cell density of $2 \times 10^{+3}$ protoplast equivalents/mL. This density-adjusted culture was mixed with 12.5 mL of a 1:1 mixture of 233 MSP Medium and 1.0% (w/v) type VII agarose solution (50° C.) supplemented with 50 mg/liter of kanamycin or 2 ng/mL chlorsulfuron. Five mL aliquots of the mixed cultures were quickly dispensed with a 25 mL wide-mouth serological pipette into fresh petri dishes. The final plating density was $1 \times 10^3$ protoplast equivalents/mL, and the osmoticum of the culture was 0.1M. The plates were solidified as described above. The embedded cells were scored for growth on a colony counter approximately 10 days later.

Day 25+:

Ten to twelve individual transformed calluses/colonies were picked and transferred with a No. 11 scalpel to a petri dish containing MSR medium with or without the appropriate selective agent for plant regeneration. The calluses were cultured at 27° C., with a photo period of 16 hours of light (5000–8000 lux) followed by 8 hours of darkness. Shoots appeared after 2–3 weeks and continued to be produced for several months. Shoots of 2–3 mm length were excised with a sharp surgical blade and transferred for rooting to OMS Medium in Magenta boxes.

After root formation (1 to 4 weeks), plants were transferred to soil for regeneration by the methods of R. S. Chaleff and M. F. Parsons, Proc. Natl. Acad. Sci.-U.S.A. 75:5104 (1978), and B. Tisserat in Plant Cell Culture: A Practical Approach, Ed. Dixon, R. A., IRL Press, Oxford (1985).

Results of Co-cultivation:

The results of the co-cultivation experiments show that the nucleic acid fragment of the invention—but not the tobacco SURA gene for the herbicide-sensitive form of ALS—confers herbicide resistance when introduced into herbicide-sensitive tobacco cells (Tables 4 and 5, below). Since the nucleic acid fragment of the invention can confer herbicide resistance at a similar frequency when introduced in either orientation with respect to the vector, it is believed to contain the regulatory sequences both 5' and 3' to the coding sequence which are required for the expression of the herbicide-resistant ALS gene.

The level of herbicide resistance conferred by the nucleic acid fragment of the invention was determined by plating one hundred colonies each of pAGS152 transformed N. tabacum cells resistant to chlorsulfuron at 2 ppb and non-co-cultured wild type N. tabacum cells on different concentrations of chlorsulfuron. The number of colonies actively growing on different concentrations of chlorsulfuron after one month was scored (Table 6, below). While wild type colonies are sensitive to chlorsulfuron at 2 ppb, colonies derived from co-cultivation with A. tumefaciens containing pAGS152 could tolerate up to 2000 ppb. This level of resistance of the transformants is comparable to that of the Hra herbicide-resistant mutant tobacco from which the nucleic acid fragment of the invention was isolated, and it is about ten fold higher than that of S4 herbicide-resistant mutant tobacco (parent of Hra).

TABLE 4

Transfer of DNA from Phage Clone 1 to Sensitive N. tabacum Cells
Number of colony forming units derived from protoplast equivalents one month after co-cultivation

|  | N.t.[1] | N.t./p145[2] |
|---|---|---|
| no selection | $3.5 \times 10^4$ | $3.6 \times 10^4$ |
| Kanamycin 50 μg/mL | 0 | $5.9 \times 10^2$ |
| Chlorsulfuron 2 ng/mL | 0 | 0 |

[1]Non-cocultured (control) plant cells.
[2]Plant cells co-cultured with A. tumefaciens harboring pAGS145, kanamycin resistance vector containing the tobacco gene for herbicide-sensitive ALS from phage clone 1.

TABLE 5

Transfer of DNA from Phage Clone 3 to Sensitive N. tabacum Cells
Number of colony forming units derived from 5 protoplast equivalents one month after co-cultivation

|  | N.t.[1] | N.t./p112[2] | N.t./p152[3] |
|---|---|---|---|
| no selection | $2.0 \times 10^4$ | $2.0 \times 10^4$ | $1.6 \times 10^4$ |
| Kanamycin 50 μg/mL | 0 | $2.5 \times 10^3$ | $6.2 \times 10^2$ |
| Chlorsulfuron 2 ng/mL | 0 | 0 | $6.5 \times 10^2$ |

[1]Non-cocultured (control) plant cells.
[2]Plant cells co-cultured with A. tumefaciens harboring pAGS112, kanamycin resistance vector.
[3]Plant cells co-cultured with A. tumefaciens harboring pAGS152, kanamycin resistance vector containing phage clone 3.

TABLE 6

Level of Chlorsulfuron Resistance in Cells of N. tabacum cv. W38 Transformed with Mutant ALS Gene
Number of Colonies Actively Groing After One Month on Selective Media[1]

| chlorsulfuron (ppb) | N. tabacum[2] | N. tabacum/[3] mutant ALS gene |
|---|---|---|
| 0 | 100 | 100 |
| 20 | 0 | 100 |
| 50 | 0 | 100 |
| 200 | 0 | 100 |

TABLE 6-continued

| | | |
|---|---|---|
| 500 | 0 | 100 |
| 2000 | 0 | 99 |
| 20000 | N.D.[4] | 6 |
| 50000 | N.D.[4] | 0 |

[1] One hundred colonies plated at each chlorsulfuron
[2] Colonies derived from non-cocultured (control) plant cells.
[3] Colonies derived from co-cultivation with *A. tumefaciens* harboring pAGS152 and initially selected for chlorsulfuron resistance at 2 ppb.
[4] Not determined.

N. tabacum Culture Media
K₃ Medium

| Ingredient | Stock | [Final] | Amount/Liter |
|---|---|---|---|
| K₃ Major salts | 10× | | 100 mL |
| CaCl₂.2H₂O | 100× | | 10 mL |
| Fe EDTA | 100× | | 10 mL |
| B5 vitamins | 100× | | 10 mL |
| MS minors I | 1000× | | 1 mL |
| MS minors II | 1000× | | 1 mL |
| glucose | — | 0.4M | 72.08 gm |
| or | | | |
| sucrose | | 0.4M | 136.8 |

K₃/S (1) - sucrose, phytohormone regime 1 (elevated)
K₃/G (1) - glucose, phytohormone regime 1 (elevated)
K₃/G (2) - glucose, phytohormone regime 2 (reduced)
1 - NAA 3.0 mg/liter
BAP 1.0 mg/liter
2 - NAA 0.1 mg/liter
BAP 0.1 mg/liter
bring pH to 5.7, filter sterilize, and store at 50.

C-Medium

| Ingredient | Stock | [Final] | Amount/liter |
|---|---|---|---|
| C-Media majors | 10× | | 100 mL |
| Fe EDTA | 100× | | 10 mL |
| B5 vitamins | 100× | | 10 mL |
| MS minors I | 1000× | | 1 mL |
| MS minors II | 1000× | | 1 mL |
| Mannitol | | 0.2M | 36.44 gm |
| Sucrose | | 0.1M | 34.2 gm |
| Mes buffer | | 3.0 mM | 590 mg |
| NAA | 1 mg/ml | 0.1 mg/liter | 100 ul |
| BAP | 1 mg/ml | 0.1 mg/liter | 100 ul | bring pH to 5.7, filter sterilize, and store at 5°.

MSP-Medium (for cell proliferation)

| Ingredient | Stock | [Final] | Amount/liter |
|---|---|---|---|
| MS majors | 10× | | 100 mL |
| Fe EDTA | 100× | | 10 mL |
| B5 vitamins | 100× | | 10 mL |
| MS minors I | 1000× | | 1 mL |
| MS minors II | 1000× | | 1 mL |
| Sucrose | | 0.1M | 34.2 gm |
| Mes buffer | | 3.0 mM | 590 mg |
| NAA | 1 mg/ml | 0.1 mg/liter | 100 ul |
| BAP | 1 mg/ml | 0.1 mg/liter | 100 ul | bring pH to 5.7, filter sterilize, and store at 5°.

MSR-Medium (for plant regeneration)

| Ingredient | Stock | [Final] | Amount/liter |
|---|---|---|---|
| MS major | 10× | | 100 mL |
| Fe EDTA | 100× | | 10 mL |
| B5 vitamins | 100× | | 10 mL |
| MS minors I | 1000× | | 1 mL |
| MS minors II | 1000× | | 1 mL |
| Sucrose | | 0.1M | 34.2 gm |
| Mes buffer | | 3.0 mM | 590 mg |
| NAA | 1 mg/ml | 0.1 mg/liter | 100 ul |
| BAP | 1 mg/ml | 1.0 mg/liter | 1.0 mL |
| bring pH to 5.7, → add agar | | | |
| Agar (T.C.) | | 0.8% (w/v) | 8.0 gm |
| autoclave | | | |
| Kanamycin Sulfate | 50 mg/ml | 50 ug/ml | 1.0 mL |
| or | | | |
| Chlorsulfuron | 1 mg/ml in 5 mM | as desired | — |

KOH
Dispense 25 mL/100 × 25 mm petri dish and,
if required, aseptically add selective agents when media has cooled to 50°.

OMS-Medium (for plant maintenance)

| Ingredient | Stock | [Final] | Amount/liter |
|---|---|---|---|
| MS majors | 10× | | 100 mL |
| Fe EDTA | 100× | | 10 mL |
| MS minors I | 1000× | | 1 mL |
| MS minors II | 1000× | | 1 mL |
| B5 vitamins | 100× | | 10 mL |
| Sucrose | | 3.0% w/v | 30 gm |
| Mes buffer | | 3.0 mM | 590 mg |
| pH 5.7, → add agar | | | |
| Agar (T.C.) | | 0.8% (w/v) | 8.0 gm | autoclave, dispense 50 mL/3" × 4" Magenta Box

Minimal A Medium

| Ingredient | Stock | [Final] | Amount/liter |
|---|---|---|---|
| K₂HPO₄ | | | 10.5 g |
| KH₂PO₄ | | | 4.5 g |
| (NH₄)₂SO₄ | | | 1.0 g |
| Sodium citrate 2H₂O | | | 0.5 g |
| autoclave in 990 mL | | | |
| MgSO₄7H₂O | 1M | 1 mM | 1.0 mL add sterile |
| Glucose | 20% | | 10.0 mL add sterile |

To solidify media: autoclave agar (15 gm/liter)
Difco Bacto. in separate 500 mL volume. Then mix salts and agar before dispensing.

| Stock | Ingredient | [Final] | Amount/Liter |
|---|---|---|---|
| MS major salts (10×) | NH₄NO₃ | 20.6 mM | 16.5 g |
| | KNO₃ | 18.8 mM | 19.0 g |
| | MgSO₄7H₂O | 1.5 mM | 3.7 g |
| | KH₂PO₄ | 1.25 mM | 1.7 g |
| | CaCl₂2H₂O | 3.0 mM | 4.4 g |
| C-Medium major salts (10×) | NH₄NO₃ | 5.0 mM | 4.0 g |
| | KNO₃ | 15.0 mM | 15.2 g |
| | MgSO₄7H₂O | 3.0 mM | 7.4 g |
| | KH₂PO₄ | 0.5 mM | 0.68 g |
| | CaCl₂2H₂O | 3.0 mM | 4.4 g |
| K Medium major salts (10×) | KNO₃ | | 25.0 g |
| | (NH₄)₂SO₄ | | 1.34 g |
| | MgSO₄7H₂O | | 2.5 g |
| | KH₂PO₄ | | 2.01 g |
| | NH₄NO₃ | | 2.5 g |
| CaCl₂2H₂O (100×) | CaCl₂.2H₂O | | 92.3 g |
| Fe-EDTA (100×) | Na₂EDTA | | 3.73 g |
| | FeSO₄.7H₂O | | 2.78 g |
| (dissolve EDTA entirely before adding FeSO₄; pH to 3.0) | | | |
| Ms minor I (1000×) | H₃BO₃ | | 0.620 g |
| | MnCl₂.4H₂O | | 1.980 g |
| | ZnSO₄.7H₂O | | 0.920 g |
| MS minor II (1000K) | KI | | 83 mg |
| | Na₂MoO₄.2H₂O | | 25 mg |
| | CuSO₄.5H₂O | | 2.5 mg |
| | CoCl₂.6H₂O | | 2.16 mg |
| B5 vitamins (100×) | nicotinic acid | | 0.1 g |
| | thiamin HCl | | 1.0 g |
| | pyridoxine HCl | | 0.1 g |
| | myo-inositol | | 10.0 g |
| NAA | Naphthelene acetic acid (dissolve in dilute KOH) | 1 mg/ml | 1.0 g |
| BAP | Benzylamino purine (dissolve in dilute HCl) | 1 mg/ml | 1.0 g |

Supplemental Apparatus, Chemicals & Media

| | |
|---|---|
| MES buffer (2 [N-Morpholino] ethanesulfonic Acid) | Sigma No. M-8250 |
| Agarose Type VII Low Gelling Temperature (stock maintained molten at 50°) | Sigma No. A-4018 |
| Cellulysin ™ | Calbiochem 219466 |
| Macerase ™ | Calbiochem 441201 |

TABLE 6-continued

| | |
|---|---|
| Cefotaxime, sodium salt dilute w/g.d., sterile H₂O store @ 5°, dark, <10 day as 50 mg/mL stock | Calbiochem 219380 |
| Kanamycin Sulfate dilute w/g.d., H₂O, filter sterile store @ −20°, dark as 50 gm/ml stock | Sigma No. K-4000 |
| Chlorsulfuron | E. I. du Pont de Nemours and Company, Wilmington, Delaware 19898 |
| 100 mm × 20 mm tissue culture petri dish | Corning 25020 |
| Babcock bottle | Kimble |
| Centrifuge (Babcock compatible) | Damon/IEC Division HN-SII |
| Magenta Boxes 3" × 4" | Magenta Corp. 4149 W. Montrose Ave Chicago, IL 68641 |
| T.C. Agar | KC Biological CR-100 |

EXAMPLE II

Tobacco DNA from the C3 mutant was prepared and a genomic DNA library in bacteriophage vector EMBL3 was constructed as described in EXAMPLE I. Phage carrying ALS genes were identified, as described in EXAMPLE I, by hybridization to a $^{32}$P-labeled 5' tobacco ALS gene fragment probe.

Six independent recombinant phage were isolated in a screen of 600,000 recombinants from the C3 library. Restriction endonuclease analysis of these isolated phage indicated that the DNA inserts of three phage could be aligned with the SURA gene from the Hra library (phages 35, 36 and 38). The remaining three phage (phage 31, 34 and 37) had DNA inserts corresponding to the SURB gene. It was expected that the ALS gene carried on phages 35, 36 and 38 would be the SURA-C3 gene, encoding herbicide resistant ALS and the ALS gene carried on phages 31, 34 and 37 would be the SURB gene, encoding herbicide sensitive ALS.

DNA fragments from phages 31, 35 and 38 were subcloned into the pUC119 plasmid and subsequently into the pAGS135 binary vector essentially as described in EXAMPLE I. An approximately 8.3 kb Spe I restriction endonuclease fragment from phage 31, analogous to that present in pAGS148 (FIG. 2), but carrying the SURB gene encoding herbicide sensitive ALS, was subcloned in both possible orientations in the vector. An approximately 6.3 kb Spe I-Sal I restriction endonuclease fragment from phage 35 and an approximately 7.8 kb Spe I-Sal I fragment from phage 38 were subcloned yielding pALS35(ATCC #67424) and pALS38, respectively. The fragments included 2.5 kb in the 5' direction (upstream) of the ALS coding region, 2.0 kb of ALS coding sequence, encoding herbicide resistant enzyme and 1.8 and 3.3 kb, respectively in the 3' direction (downstream) from the ALS coding region. The latter two subcloned fragments contain a BamH I restriction endonuclease site. Partial BamH I digestions or pALS35 and pALS38 were employed for insertion of these plasmids into the BamH I site of the binary vector pAGS135. The ALS genes in the binary vector, designated p312, p313, p351 and p381 (Table 7) were moved into *A. tumefaciens* by tri-parental mating, as described in EXAMPLE I.

Introduction of the ALS genes into herbicide sensitive tobacco by co-cultivation of plant cells with *A. tumefaciens* carrying the ALS genes in the binary vector was performed as described in EXAMPLE I. The results of these co-cultivation experiments are shown in Table 7. The ALS gene isolated in phage 31, i.e. the SURB gene encoding herbicide sensitive ALS, yielded no herbicide resistant plant cells, as expected. The ALS gene isolated in phages 35 and 38, i.e. the SURA-C3 gene encoding herbicide resistant ALS did yield herbicide resistant plant cells. Herbicide resistant plant cells arose at a lower frequency than kanamycin resistant plant cells and at a lower frequency than was observed when the SURB-Hra gene was used. This may reflect either the lesser resistance to the herbicide of the ALS enzyme encoded by the SURA-C3 gene compared to that encoded by the SURB-Hra gene, or the lower expression of the SURA-C3 gene compared to the SURB-Hra gene, or both.

TABLE 7

ALS Reintroduction Exp. 3
Transfer of DNA from phage clones 31, 35 & 36
to Sensitive *N. tabacum* Cells
Number of Colony Forming Units derived from 10⁵
Protoplast Equivalents One Month after Co-cultivation

| | N.t.[1] | N.t./ p152[2] | N.t./ p312[3] | N.t./ p313[4] | N.t./ p351[5] | N.t./ p381[6] |
|---|---|---|---|---|---|---|
| no selection | 2.1 × 10⁴ | 1.5 × 10⁴ | 1.1 × 10⁴ | 1.9 × 10⁴ | 1.5 × 10⁴ | 1.4 × 10⁴ |
| Kanamycin 50 ug/ml | 0 | 88 | 65 | 48 | 139 | 87 |
| Chlorsulfuron 2 ng/ml | 0 | 83 | 0 | 0 | 32 | 18 |

[1]Non co-cultured plant cells.
[2]Plant cells co-cultured with *A. tumefaciaens* harboring pAGS152, S4/Hra sublcone.
[3]Plant cells co-cultured with *A. tumefaciaens* harboring pAGS312, C3 subclone, φ31 (orientation 1).
[4]Plant cells co-cultured with *A. tumefaciaens* harboring pAGS313, C3 subclone, φ31 (orientation 2).
[5]Plant cells co-cultured with *A. tumefaciaens* harboring pAGS351, C3 subclone, φ35.
[6]Plant cells co-cultured with *A. tumefaciaens* harboring pAGS381, C3 subclone, φ38.

EXAMPLE III

Mutations were made in the wild-type SURA gene of tobacco in vitro in order to make it encode a herbicide resistant ALS. Restriction endonuclease fragments containing part of the SURA gene were subcloned into M13 phage vectors or plasmid vectors containing an M13 origin of replication to allow production of single-stranded DNA. The specific DNA fragment subcloned depended upon the region to be mutagenired in vitro and the availability of restriction endonuclease sites.

Oligonucleotides 16-17 bases in length, which hybridized to the single-stranded DNA from the SURA ALS gene with single base mismatches, were synthesized. These mismatches were designed to convert amino acid codons found in the wild-type ALS gene to the codons found in ALS genes which encode ALS enzymes resistant to sulfonylurea herbicides. These oligonucleotides include 5' GTTCAATTGGAG-GATC 3', to change trp 591 to leu, 5' GTCAAGTG- GCACGTAGG 3', to change pro 197 to ala, and 5' GTCAAGTGTCACGTAGG 3', to change pro 197 to ser, 5' ATGTACCTGAGGATATT 3' to change lys 256 to glu, 5' GAGGTTTGTTGATAGAG 3' to change asp 384 to val, 5' AGGTTTGAGGATAGAGT 3' to change asp 384 to gln, 5' TACTGATGATTTTCAGG 3' to change ala 205 to asp and 5' CAGGTGGCCCTTCCATG 3' to change ala 122 to pro.

The oligonucleotides were hybridized to single-stranded DNA and used as primers for synthesis of a complementary strand in a reaction catalyzed by the Klenow fragment of DNA polymerase I, following the procedures of Carter et al. (Oliqonucleotide site-directed mutagenesis in M13, Anglian Biotechnology Limited, England, 1985). The resulting DNA was transformed into competent *E. coli* mutL cells (Kramer et al., 1984. Cell 38. 879). Individual plagues or colonies were purified, depending on whether M13 phage vectors (M13mp18/19) or M13 replication origin plasmid vectors (pTZ18R/19R. Pharmacia; Piscataway. N.J.) were used. Mini-preps of single-stranded DNA were made and used in DNA sequencing reactions to identify clones that carried the mutated bases.

These in vitro constructed site-specific mutations can be incorporated singly or in combination into either a wild type SURA or SURB gene which includes the 5' and 3' regulatory sequences needed to provide expression of the gene in plant cells (see EXAMPLES I and II). This is accomplished by substituting restriction endonuclease fragments carrying the mutations into a plasmid carrying the SURA or SURB gene from which the analogous fragment has been removed. The choice of the restriction fragment to substitute depends upon the position of the mutation in the gene and the availability of restriction endonuclease sites. The introduction of the mutated genes into plant cells can then be accomplished as described in EXAMPLES I and II. Any of the DNA fragments containing mutations which result in production of herbicide resistant ALS, as disclosed in the description of the invention, can be produced essentially by this method. Furthermore, the mutations need not be made exclusively in the SURA gene. Analogous mutations can be made in the SURB gene or any other plant gene encoding ALS for which DNA sequence information is available.

Several different 1.4 kb Nco I to Bgl II DNA fragments from the in vitro mutated SURA gene (nucleotide positions 533–1952 as indicated in FIG. 5) were inserted into the SURB gene (nucleotide positions 1234–2653 as indicated in FIG. 4) replacing the wild type SURB gene sequence.

The ability of these chimetic ALS genes to confer herbicide resistance on plant cells was assayed by co-transforming tobacco protoplasts with plasmids carrying the mutated ALS genes and with a second plasmid carrying a NOS-NPTII-NOS gene. Half of each transformation mixture was subjected to selection on kanamycin and half to selection on chlorsulfuron. The recovery of chlorsulfuron-resistant colonies is shown as a percentage of kanamycin-resistant colonies in Table 8.

Protoplasts were prepared from *Nicotiana tabacum* cv. Xanthi by the method of Nagy and Maliga [Callus induction and plant regeneration from mesophyll protoplasts of *N. sylvestris*. Z. Pflanzenphysiologie 78:453–455 (1976)], as modified by Potrykus and Shillito [Protoplasts: isolation, culture, plant regeneration. In: Weissbach A, Weissbach H (ads.) Methods in Enzymology 118: 549–578. Academic Press. (1985)]. DNA was introduced into protoplasts as follows, after the methods of Krens [In vitro transformation of plant protoplasts with Ti-plasmid DNA. Nature 296:72–75 (1982)] and Shillito, [Agarose plating and a bead type culture technique enable and stimulate development of protoplast derived colonies in a number of plant species. Plant Cell Reports 2: 244–247 (1983); High effeciency direct gene transfer to plants. Biotechnology 3:1099–1103 (1985)].

Protoplasts were resuspended at 1.5 million cells/ml in sterile 0.4M mannitol. 6 mMMgCl2, 0.1% MES pH 5.8. and divided into aliquots of one million cells in sterile 50 ml centrifuge tubes. The cells were subjected to a 45° C. heat shock for five minutes, and then quickly cooled on ice to room temperature.

Ten μg of the plasmid pKNKS carrying the NOS-NPTII-NOS gene. 10 μg of the appropriate ALS gene-carrying plasmid, and 30 μg of sheared calf thymus DNA were ethanol-precipitated, resuspended in 50 μl sterile water, and then added to each aliquot of protoplasts. 40% PEG in 0.4M mannitol, 30 mM MgCl2, 0.1% MES pH 5.8 was added dropwise to each tube, by forcing the solution through a syringe-mounted 0.45 μm filter, to a final concentration of 13% PEG. Tubes were swirled gently several times during a ten minute period to keep the phases mixed. Three 0.33 ml aliquots from each transformation mix were gently pipetted into 60×15 mm sterile culture dishes containing 3 ml sterile H Medium by the method of Potrykus and Shillito (2) and swirled gently to mix. Dishes were sealed with Parafilm and incubated three days in the dark and four days in the light at 25° C.

Cells were resuspended by scraping the bottom of each dish with a sterile cell scraper, and then 3.3 ml of 1.2% DNA-grade agarose in K3A Medium, autoclaved and cooled to 45° C. was added to each dish. Dishes were swirled immediately to mix phases. When the agarose had solidified, each disk was cut into quarters, thus producing twelve quarters from each transformation. Agarose quarters were floated, three per dish, in 100×25 mm sterile culture dishes containing 25 ml of 1:1 K3A:H Medium and the appropriate selective agent. Six quarters. representing 500.000 cells in the original mix, from each transformation were floated in 50 mg/L kanamycin and six were floated in 2 ppb chlorsulfuron. Dishes were incubated in the light at 25° C.

After one week, one half of the liquid medium in each dish was replaced with 1:1 K3A:H containing the appropriate selective agent. After one more week, one half of the liquid medium was replaced with 1:1 K3E:J containing the appropriate selective agent. Media were then replenished bi-weekly with 1:1 K3E:J until colonies became visible. Final colony count was at 6 weeks.

The data shown in Table 8 indicates that all of the in vitro mutated ALS genes can be used to transform tobacco cells to herbicide resistance. However, the frequency of obtaining herbicide resistance varies widely; the reason for this is not yet known.

TABLE 8

| | Herbicide Resistant Transformants with In Vitro Mutated ALS Genes | | |
|---|---|---|---|
| | Colonies/1 Million Treated Cells | | |
| ALS Gene | 50 mg/L Kan | 2 ppb Chlorsulfuron | Cs-R/Kan-R (%) |
| None | 323 | 1 | 0.3 |
| SURB-Hra[1]: | 430 | 126 | 29.3 |

TABLE 8-continued

Herbicide Resistant Transformants with In Vitro Mutated ALS Genes

| ALS Gene | Colonies/1 Million Treated Cells | | |
|---|---|---|---|
| | 50 mg/ L Kan | 2 ppb Chlorsulfuron | Cs-R/ Kan-R (%) |
| (Ala 197 + Leu 591) | | | |
| SURB/SURA[2]: (wild type) | 229 | 0 | 0.0 |
| SURB/SURA: (Ala 197) | 68 | 8 | 11.8 |
| SURB/SURA: | 78 | 39 | 50.0 |
| (Ala 197 + Leu 591) | | | |
| SURB/SURA: (Ser 197) | 205 | 80 | 39.0 |
| SURB/SURA: | 180 | 49 | 27.2 |
| (Ser 197 + Leu 591) | | | |
| SURB/SURA: (Leu 591) | 127 | 7 | 5.5 |
| SURB/SURA: (Asp 205) | 105 | 31 | 29.5 |
| SURB/SURA: (Glu 256) | 86 | 3 | 3.5 |
| SURB/SURA: (Val 384) | 80 | 1 | 1.2 |

[1]Gene isolated from Hra plants, carrying in vivo derived mutations.
[2]Chimeric SUR-SURA gene in which the NcoI to BglII fragment of SURB is substituted with the equivalent fragment from SURA; no in vitro mutations.

EXAMPLE IV

DNA was prepared from *Beta vulgaris* cv. Sennika (sugarbeet) and a genomic DNA library in bacteriophage lambda vector EMBL3 was constructed as described in EXAMPLE I. Recombinant phage (300,000) were screened by hybridization to a P-labeled 5' ALS tobacco gene fragment probe as described in EXAMPLE I. The filters were washed at 42° C. (0.1×SSC) and 20 individual clones were isolated. On the second round of purification the recombinant phage were hybridized to both the 3' tobacco ALS gene probe and the 5' probe. In addition, the filters which had been hybridized to the 5' probe were washed at 55° C. Only one clone, φ21, hybridized to both 5' and 3' probes and also remained hybridized after the 55° C. wash. Minilysate DNA preparations were made from the 20 clones and digested with EcoR I and Nco I. The different isolates had different restriction endonuclease digestion patterns and again only φ21 hybridized to both probes and remained hybridized after a 55° C. wash. One phage, φ41, also had a hybridizing band remaining after a 55° C. wash but it did not hybridize to the 3' probe. FIG. 7 shows the restriction endonuclease map of the phage φ21, together with subclones which have been constructed from it. The ALS coding region was localized to a 3.0 kb BamH I-Hind III fragment by hybridization with 5' and 3' probes from the *N. tabacum* gene. Both DNA strands of this fragment have been sequenced. The BamH I-Hind III fragment was subcloned into pUC119 or Bluescript (Strategene; San Diego, Calif.) vectors: then Exonuclease III or Bal 31 deletions were generated. The dideoxy sequencing method was used. A comparison of the deduced amino acid sequence encoded by the sugarbeet gene with that of the tobacco gene(s) indicates no homology in the first 88 amino acids of the predicted protein (see FIG. 8). This region may represent the chloroplast transit peptide. Thereafter the homology is approximately 90% with an insertion of 4 amino acids around residue 290 of tobacco ALS. Inspection of the amino acid residues which define the sites for herbicide resistance identified in tobacco and yeast indicate that these residues are conserved in sugarbeet ALS also. These data allow a straightforward approach to the construction of a gene encoding herbicide resistant sugarbeet ALS enzyme, by site-directed mutagenesis, as described in EXAMPLE III.

Three sites have been mutagenized in this sugarbeet gene. The codon GCA for ala at position 122 (numbering of amino acid residues from FIG. 6) was changed to CCA for pro, the codon CCA for pro at position 197 was changed to GCA for ala and the codon TGG for trp at position 591 was changed to TTG for leu. The double mutation yielding pro to ala at 197 and trp to leu at 591. which mimics the tobacco SURB-Hra gene, was also made by combining the two single mutations.

In order to transform plants with these in vitro constructed mutations in the sugarbeet ALS gene. DNA fragments containing the mutations and extending from the BamH I site about 910 bp in the 5' direction (upstream) of the coding region to the Pst I site about 1000 bp in the 3' direction (downstream) of the coding region (see FIG. 17) were cloned into plasmid vector pUC119. These were introduced into the binary vector pAGS140 for transformation into plant cells as described in EXAMPLE I. The binary vector pAGS140 is similar to pAGS135 (FIG. 2) except that between the BamH I site and the right border of the T-DNA of the Ti-plasmid of *Agrobacterium tumefaciens* a gene which will confer resistance in plants to the antibiotic hygromycin was inserted.

Introduction of the ALS genes into herbicide sensitive tobacco and sugarbeet, by co-cultivation of the plant cells with *A. tumefaciens* carrying the ALS genes in the binary vector, was performed as described in EXAMPLE I and EXAMPLE II. Results of a co-cultivation experiment in tobacco are shown in Table 9. Herbicide resistant transformants were obtained with three of the four mutant sugarbeet ALS genes. The frequency of obtaining herbicide resistant transformants was lower than that for kanamycin resistant transformants, and also lower than the frequency of herbicide resistant transformants obtained when the tobacco SURB-Hra gene was used. It is believed that this results from poor expression of the mutant sugarbeet ALS genes in tobacco. This may reflect either insufficient nucleotide regulatory sequences upstream or downstream of the mutant sugarbeet ALS genes in the DNA fragments used or poor utilization of sugarbeet nucleotide regulatory sequences in tobacco, or both. The mutant sugarbeet ALS gene carrying the Ala 122 to Pro substitution did not yield chlorsulfuron-resistant transformants as expected, since it is a gene known to confer resistance to only selected sulfonylurea herbicides which do not include chlorsulfuron.

TABLE 9

Herbicide Resistance in Plant Cells Tranformed with Site Specific Mutant Sugarbeet ALS Genes

| Gene Origin | Tobacco | Sugarbeet | Sugarbeet | Sugarbeet | Sugarbeet |
|---|---|---|---|---|---|
| Mutation | pro(197)-ala/ trp(591)-leu | pro(197)-ala/ trp(591)-leu | trp(591)-leu | pro(197)-ala | ala(122)-pro |
| Chlorsulfuron ® | 1500 | 254 | 24 | 106 | 0 |
| Kanamycin ® | 2379 | 2682 | 2707 | 2376 | 892 |

TABLE 9-continued

Herbicide Resistance in Plant Cells Tranformed
with Site Specific Mutant Sugarbeet ALS Genes

| Gene Origin | Tobacco | Sugarbeet | Sugarbeet | Sugarbeet | Sugarbeet |
|---|---|---|---|---|---|
| Chl ®/Kan ® | .631 | .095 | $8.9 \times 10^{-3}$ | .045 | — |

Gene introductions were done by standard co-cultivation method. For each construction an aliquot of the co-cultured plant cells ($2 \times 10^5$ starting plant cells) was scored for chlorosulfuron and another aliquot for kanamycin resistance. Selection was with chlorsulforon at 2 ppb or kanamycin at 50 ppm.

EXAMPLE V

The SURB-Hra gene described in EXAMPLE I was transformed into tobacco cultivars by *Agrobacterium tumefaciens* infection of tobacco leaf disks and progeny of the transformants were analyzed to demonstrate expression of resistance at the whole plant level and inheritance of the herbicide resistance trait. Standard aseptic techniques for the manipulation of sterile media and axenic plant/bacterial cultures were followed, including the use of a laminar flow hood for all transfers. Potted tobacco plants for leaf disk infections were grown in a growth chamber maintained for a 12 hr, 24° C. day, 12 hr, 20° C. night cycle, with approximately 80% RH, under mixed cool white fluorescent and incandescent lights. Tobacco leaf disk infections were carried out essentially by the method of Horsch, R. B., Fry, J. E., Hoffmann, N. L., Eichholtz, D., Rogers, S. G., Fraley, R. T., (1985, Science 227: 1229–1231.

Young leaves, not fully expanded and approximately 4–6 inches in length, were harvested with a scalpel from approximately 4–6 week old tobacco plants (*Nicotiana tabacum* cv $NK^{326}$ or K14). The leaves were surface sterilized for 30 minutes by submerging them in approximately 500 ml of a 10% Chlorox, 0.1% SDS solution and then rinsed 3 times with sterile deionized water. Leaf disks, 6 mm in diameter, were prepared from whole leaves using a sterile paper punch.

Leaf disks were inoculated by submerging them for several minutes in 20 ml of a 1:10 dilution of an overnight Agrobacterium culture carrying the plasmid pAGS152. Agrobacterium cultures were started by inoculating 10 ml of Min A (EXAMPLE I) broth with a single bacterial colony removed from a Min A plus tetracycline (EXAMPLE VI) plate. The culture was grown for approximately 17–20 hours in 18 mm glass culture tubes in a New Brunswick platform shaker maintained at 28° C.

After inoculation, the leaf disks were placed in petri dishes containing CN agar medium (EXAMPLE VI). The dishes were sealed with parafilm and incubated under mixed fluorescent and "Gro and Sho" plant lights (General Electric) for 2–3 days in a culture room maintained at approximately 25° C.

To rid the leaf disks of Agrobacterium and to select for the growth of transformed tobacco cells, the leaf disks were transferred to fresh CN medium containing 500 mg/l cefotaxime and 100 mg/l kanamycin. Cefotaxime was kept as a frozen 100 mg/ml stock solution and added aseptically (filter sterilized through a 0.45 μm filter) to the media after autoclaving. A fresh kanamycin stock (50 mg/ml) was made for each use and was filter sterilized into the autoclaved media.

Leaf disks were incubated under the growth conditions described above for 3 weeks and then transferred to fresh media of the same composition.

Approximately 1–2 weeks later shoots developing on kanamycin-selected explants were excised with a sterile scalpel and planted in A medium containing 100 mg/l kanamycin. Root formation on selective and non-selective media was recorded within 3 weeks. Shoots which rooted in kanamycin were transferred to soil and grown in a growth chamber as described above. After 3 to 5 weeks, but before flowering had occurred, leaf tissue was excised and used for ALS assays as described in EXAMPLE VI. The results of these assays, which indicate that a herbicide resistant form of ALS was being produced, are shown in Table 10. The plants exhibiting herbicide resistant ALS activity were then moved to a greenhouse where they were grown to maturity. Individual flowers were bagged to permit self-fertilization without cross-pollination. Mature seeds were harvested and progeny tests were conducted to determine inheritance of the herbicide resistance trait. Seeds were surface sterilized as described above, dried and planted on SG medium (¼MS salts, 0.75% sucrose, 0.8% Agar) in the presence or absence of herbicide (DPX-F6025, Classic ®). Sensitive seeds germinated, but did not develop further. Results of the progeny analyses are shown in Table 10. A segregation ratio of 3 resistant progeny to 1 sensitive indicated the presence of a single-site insertion of the SURB-Hra gene in the genome of the transformant, which was stably inherited. This was seen in 15 of 17 transformants. Higher ratios of resistant to sensitive progeny indicated multiple insertions at unlinked positions in the genome. The 15/1 ratio indicates the presence of 2 unlinked SURB-Hra genes and the 255/1 ratio indicates 4 unlinked SURB-Hra genes in the transformants K14 #40 and K14 #7, respectively.

TABLE 10

| | % Unhibited ALS Activity[1] | Progeny Resistant/Sensitive[2] | | Segregation Ratio Resistant/ Sensitive |
|---|---|---|---|---|
| | | 100 ppb | 1000 bbp | |
| NK326 (wt) | 7 | — | — | — |
| NK326 #1 | 36 | 98/37 | 90/35 | 3/1 |
| NK326 #9c | 47 | 163/49 | 99/63 | 3/1 |
| NK326 #9d | 37 | 288/67 | 150/58 | 3/1 |
| NK326 #10 | 26 | 93/31 | 96/24 | 3/1 |
| NK326 #10c | 56 | 333/45 | 290/76 | 3/1 |
| K14 (wt) | 7 | — | — | — |
| K14 #7 | 71 | 990/4 | 109/1 | 255/1 |
| K14 #11 | 52 | 208/85 | 127/76 | 3/1 |
| K14 #27 | 45 | 129/45 | 108/42 | 3/1 |
| K14 #29 | 30 | 192/46 | 163/67 | 3/1 |
| K14 #31 | 44 | 106/35 | 99/34 | 3/1 |
| K14 #32c | 32 | 140/65 | 63/86 | 3/1 |
| K14 #40 | 41 | 218/18 | 212/26 | 15/1 |
| K14 #41 | 40 | 255/35 | 296/74 | 3/1 |
| K14 #42 | 29 | 162/74 | 77/72 | 3/1 |
| K14 #53 | 37 | 130/59 | 149/139 | 3/1 |
| K14 #54 | 34 | 99/38 | 92/43 | 3/1 |
| K14 #54A | 28 | 137/55 | 100/72 | 3/1 |

[1]The ALS activity in each line is related to the activity in the absence of herbicide which is taken as 100 percent. The sulfonylurea herbicide used was DPX-F6025 (Classic ®) at a concentration of 10 ppb.
[2]Resistant progeny are able to growth at the indicated concentrations of herbicide DPX-F6025 (Classic ®).

EXAMPLE VI

To transform herbicide sensitive tomato to resistance the SURB-Hra gene from tobacco, carried on the binary vector pAGS152 in *A. tumefaciens* strain LBA4404, was used (see EXAMPLE I).

Standard aseptic techniques for the manipulation of sterile media and axenit plant/bacterial cultures were followed, including the use of a laminar flow hood for all transfers.

Seeds of tomato (*Lycopersicon esculentum* vat. Herbst Red Cherry) were surface sterilized for 30 minutes in a 10% Chlorox, 0.1% SDS solution and rinsed 3 times with sterile deionized water. The seeds were planted in Magenta boxes (Magenta Corp.) containing 100 ml of OMS agar medium and germinated under mixed fluorescent and "Gro and Sho" plant lights (General Electric) in a culture room maintained at approximately 25° C. Cotyledons from 10-15 day old seedlings were used for Agrobacterium inoculation.

Cotyledons were wounded by removing approximately 2 mm of tissue from each end of the cotyledon with a sterile scalpel. Wounded cotyledons were planted in petri dishes on CTM agar medium either with or without 75 μM acetosyringone (Aldrich Chemical).

In preparation for the cotyledon inoculation, a single bacterial colony from a Min A+tetracycline (1 μg/ml) agar plate was inoculated into a flask containing 30 ml of Min A broth (EXAMPLE I) and grown for 2 days at 28° C. in a New Brunswick platform shaker. On the morning of the cotyledon inoculation, the bacterial culture was diluted with sterile Min A broth to an OD of 0.1 at 650 nM and allowed to multiply to an OD of 0.2 under the growth conditions previously described. This culture was then used undiluted for the inoculation.

CTM agar plates containing the colyledon explants were flooded with 5 ml of the bacterial solution for approximately 5 minutes, before removal of the solution. The plates were then secured with Time Tape (Shamrock Scientific Specialty) on two sides of the dish and incubated for 2 days under mixed fluorescent and "Gro and Sho" plant lights (General Electric) at approximately 25° C. for two days.

To rid the plant cultures of Agrobacterium and to select for the growth of transformed tomato cells, the cotyledon explants were transferred to fresh CTM medium containing 500 mg/L cefotaxime and 50 mg/L kanamycin and incubated under the same culture conditions described above for approximately 3 weeks. The cotyledons were than transferred to fresh media of the same composition and selective agents as CTM but with 1/10 the zeatin concentration.

After approximately 2-4 weeks, shoots developing off of kanamycin-selected cotyledons were excised and planted in OMS media containing 500 mg/L cefotaxime and 100 mg/L kanamycin. Tomato shoots which rooted in kanamycin after about 2-3 weeks were transferred to soil in 8" pots and covered with plastic bags. The plants were grown under mixed fluorescent and incandescent lights for a 12 hr, 24° C. day; 12 hr, 20° C. night cycle, with approximately 80% relative humidity, for one week before removing the plastic bags. The plants were grown for another 2-4 weeks before performing ALS assays. An increase of uninhibited ALS activity in the presence of the sulfonylurea Classic ® in leaf extracts from transformed plants was demonstrated in these experiments (Table 11).

TABLE 11

ALS Activity of Wild-Type and Transformed Tomato

| | Percent Uninhibited ALS Activity[1] | | | |
|---|---|---|---|---|
| | 0 ppb | 10 ppb | 100 ppb | 1000 ppb |
| Wild-type | 100 | 15 | 5 | 4 |
| Transformant #3 | 100 | 42 | 25 | 12 |
| Transformant #4a | 100 | 60 | 42 | 26 |
| Transformant #4b | 100 | 29 | 15 | 5 |
| Transformant #4c | 100 | 58 | 43 | 25 |
| Transformant #4d | 100 | 29 | 15 | 10 |

[1]The ALS activities in each line are relative to the activity in the absence of herbicide which is taken as 100 percent. The sulfonylurea compound used was DPX-F6025, the active ingredient in Classic ® herbicide.

The assay for ALS activity in the absence or presence of herbicide from transformed or untransformed plants was conducted as follows:

1. Grind 2.5 grams of relatively young leaf tissue (4-6 inches in length) in a tissue homogenizer containing 10 ml extraction buffer (100 mM KHPO4 pH 7.5, 0.5 mMMgCl2, 10% glycerol, 1 mM pyruvate, 0.5 mM TPP, 10 nM FAD) and 200 mg Polyclar AT (BDH Biochemicals). Keep on ice.
2. Homogenize extract for approximately 10 seconds in a polytron (Brinkman Instruments) on setting #7.
3. Centrifuge extract in a Sorvall SS-34 rotor, 20 min. 16K rpm, 4° C.
4. Equilibrate PD-10 (Pharmacia) columns by washing with column buffer (100 mM KHP04 pH 7.5, 0.5 mM MgCl2, 10% glycerol, 1 mM pyruvate) 5 times.
5. To plant extract supernatant, add cold saturated (NH4)2SO4 to achieve a 50% cut. Incubate on ice for 30 minutes.
6. Centrifuge extract in SS-34 rotor, 20 minutes, 16K rpm, 4° C. Decant supernatant.
7. Resuspend pellet in 1 ml cold column buffer.
8. Load extract onto column and chase with a volume of column buffer to achieve total volume loaded equal to 2.5 ml. Let this run through column.
9. Elute proteins with 2× volume of extract loaded. Recover in 15 ml Falcon tube placed beneath column.
10. Set up reaction for each extract in microfuge tubes as follows: 350 μl reaction mix (200 mM pyruvate, 5 mM TPP, 0.9 mM FAD, 5 mM KHPO4 pH 7.0), 50 μl of either 5 mM KHPO4 or desired sulfonylurea concentration, and 100 μl plant extract.
11. Incubate reaction for 1 hour, 30° C.
12. To stop reaction, add 50 μl 6M H2SO4 and incubate at 60° C. for 10 minutes. Spin in microfuge 5 minutes.
13. Set up color development tubes as follows: 500 μl 0.5% creatin, reaction tube supernatant, 0.5 ml α-napthol solution (1.5 g α-napthol in 30 ml 2.5 N NaOH). Mix and heat at 60° C. for 20 minutes.
14. Vortex each tube and load 100 μl of each sample into wells of microtiter plate. Read at OD 530.

B
Callus Induction Medium

| | |
|---|---|
| 1 package of MS salts (Gibco Murashige Organics MEdium with 3% sucrose | per liter |
| 1 ml of 1 mg/ml NAA | pH 5.8 |
| 0.2 ml of 1 mg/ml BAP | |
| 0.8% agar | |

CN

-continued

Shoot Induction Medium
| | |
|---|---|
| 1 package of MS salts with 3% sucrose | per liter |
| 1 ml of 1 mg/ml NAA | pH 5.8 |
| 1 ml of 1 mg/ml BAP | |
| 0.8% agar | |

A
Root Induction Medium
| | |
|---|---|
| 1 package of MS salts (without sucrose) | per liter |
| 10 grams sucrose | pH 5.8 |
| 0.8% agar | |

Agrobacterium R-Medium
Add 7.5 g agar to 440 ml $H_2O$, autoclave, and keep at 55° C. Add sterile stocks of:

| | |
|---|---|
| 0.5 Ml | 1M $MgSO_4$ |
| 0.5 ml | 1M $CaCl_2$ |
| 10.0 ml | 20% sucrose |
| 5.0 ml | 100 mg/ml kanamycin |
| 50.0 ml | 10× salts ($Na_2HPO_4.7H_2O$ 60 g/l; $KH_2PO_4$, 30 g/l; NaCl, 5 g/l; $NH_4Cl$. 10 g/l) |

CTM Medium
1 pkg MS salts
1 ml B5 vitamins (per 100 ml; Nicotinic Acid 100 mg, thaimine, hydrochloride 1000 mg, pyridoxine hydrochloride 100 mg, M-inositol 10,000 mg)
3 mM MES
3% glucose
0.7% agar
pH 5.7
Autoclave and add 1 ml 1 mg/ml zeatin stock

OMS Medium
1 pkg MS salts
1 ml B5 vitamins (see above)
3 mM MES
3% sucrose
0.8% agar
pH 5.7

Min A + Tetracycline (1 ug/ml) Medium
1. Add 7.5 g agar to 400 ml $H_2O$
2. Make stock:

| | |
|---|---|
| $K_2HPO_4$ | 5.25 g |
| $KH_2PO_4$ | 2.25 g |
| $(NH_4)_2SO_4$ | 0.5 g |
| Sodium Citrate $2H_2O$ | 0.25 g |
| | 100 ml |

3. Make $MgSO_4.7H_2O$ stock = 20 g/100 ml, autoclaved.
4. Make glucose stock = 20% solution, autoclaved
5. Make tetracycline stock = 1.0 mg/ml in ethanol/$H_2O$, 50% v/v filter sterilized To make Min A medium + 1 μg/ml tetracyline:
Mix (1) and (2)
Add 0.5 ml of (3), 5 ml of (4), and 0.5 ml of (5)

YEB Medium
| | per liter |
|---|---|
| Bacto Beef Extract | 5.0 g |
| Bacto Yeast Extract | 1.0 g |
| Peptone | 5.0 g |
| Sucrose | 5.0 g |
| $MgSO_4 7H_2O$ | 0.5 g |
| Agar (optional) | 15.0 g |

| | |
|---|---|
| Herbicide solution: | A 1 ppm stock solution of sulfonylurea herbicide can be made by dissolving 1 mg of herbicide in 100 ml of 0.01 N $NH_4OH$, and then diluting 1:10 with 5 mM $KHPO_4$ pH 7.0. This stock will suffice to assay herbicide concentrations of 100 ppb or lower. If higher concentrations are desired, dissolve 1 mg in 10 ml of 0.01 N $NH_4OH$, etc. |
| Herbicide dilutions: | In the standard assay, 50 μl of herbicide is added to 450 μl assay mix and extract, for a 1:10 dilution of herbicide. So, for each concentration to be tested, a 10× solution in 5 mM $KHPO_4$ pH 7.0 should be diluted from the stock solution. |

EXAMPLE VII

The tobacco SURB-Hra gene encoding herbicide resistant ALS was used to transform *Beta vulgaris* (sugarbeet) to herbicide resistance by the following *Agrobacterium tumefaciens* mediated transformation procedure.

In order to surface sterilize seeds. 50–100 seeds were placed in a 25×100 mm sterile petri dish in a laminar flow hood and 25–30 ml of 70% ethanol was added. Seeds were agitated by hand 1–2 min., the ethanol was decanted, and 25–30 ml 20% Clorox (20 ml commercial bleach/80 ml sterile $H_2O$/1 drop Tween 80) was added. The seeds were agitated on a gyrotary shaker at 40 rpm for 20 mins., and the bleach was decanted. The bleach sterilization was repeated 2 times for a total of 60 min., and the sterilized seeds were rinsed 3 times for 5 min. each with 25–30 ml sterile $H_2O$. To germinate the seeds, they were plated on ¼$PG_O$ agar solidified medium. 12 seeds/50 ml media/15 mm×150 mm petri dish, and cultured at 24° C. in darkness.

NOTE: 10–20% contamination of seed may be anticipated for a good, clean seed lot. For this reason seed is plated far apart on large plates and the germinations are monitored continuously and non-contaminated seed are transferred to fresh plates. If contamination is fungal, then transfers are conducted in a laminar flow cabinet with the fan off.

60–80% germination is expected for a good seed lot. Germination is not syncronous. An approximately 14 day period is required to obtain (a) all germinations and (b) sufficient elongation to provide many appropriate explants.

Agrobacterium overnight (O/N) suspension cultures were prepared as described in EXAMPLE I. Freshly plated Agrobacterium have shorter lag times than cultures stored for long periods at 5° C. It is important that log phase bacteria be used as inocula. Therefore, a trial should be conducted to assure an overnight culture which reaches log phase (OD 550 mm 0.4–0.8) before hypocotyl inoculation.

To prepare plant explants, hypocotyl were cut into approximately 0.5 cm sections with a sharp surgical blade, and plated immediately onto agar solidified $PG_O^{0.1}$/0.1. Do not allow dessication, nor damage the wound by the use of a dull blade or by compressing with forceps.

To inoculate explants, they were dipped individually into a log phase suspension of the appropriate Agrobacterium strain. They were immersed briefly (1–3 sec.) and arranged in a grid pattern on a fresh plate: 25 explants/100mm plate of agar solidified $PG_O^{0.1}$/0.1.

The explants were dried by leaving plates open in a laminar flow hood 10–30 min. This concentrates Agrobacteria onto the wound. It also may limit possible damage by water logging. It is important, though, not to dessicate tissue. Close observation of this step is required. The plates were then sealed with parafilm and cultured at 24° C. for 3 days.

The explants were collected into liquid PG $^{0.1}$/0.1 containing cefotaxime 500μg/ml in a 25×100 mm petri dish, and shaken gently on a gyrotary shaker at 40 rpm for 1 hr. The media was decanted, replaced with fresh counterselective media, and shaken gently for an additional 2 hrs. The explants were plated in grids, 25/100 mm plate agar solidified PG $^{0.1}$/0.1 containing cefotaxime 500μg/mL and cultured at 24° C. for 3 days.

Selection for transformed plant cells was applied as follows. Explants were transferred to fresh plates of agar solidified PG $^{0.1}$/0.1 containing vancomycin 100μg/m1 or chlorsulfuron. 2 ng/ml as selective agents. The number of resistant colonies was counted after 20–30 days. More than one may be observed at each wound. Transformants were excised as follows. Callus was removed from the wound/explant with a surgical blade and cultured independently on fresh selective media. Some Agrobacterium can escape from counterselection. Additional washes in cefotaxime containing liquid media are possible as is repeated transfer cefotaxime containing agar solidified plates. Under the suggested protocol we observed approximately 15% explant contamination, which was an acceptable loss. The results of a transformation experiment using the sugarbeet line *Beta vulgaris* 87193 are shown in Table 12. The level of chlorsulfuron resistance in calli of *B. vulgaris* transformed with the SURB-Hra mutant ALS gene of tobacco, is compared to that of untransformed calli. These results demonstrate that the tobacco SURB-Hra gene, encoding herbicide-resistant ALS, can be expressed efficiently in sugarbeet.

In another experiment, sugarbeet cells were transformed to herbicide resistance with the tobacco SURB-Hra gene and the in vitro constructed site-specific mutations made in the sugarbeet ALS gene (see Example IV for construction of sugarbeet ALS gene mutations). The results shown in Table 13 indicate that in vitro constructed mutant sugarbeet ALS genes can be used to transform efficiently sugarbeet cells to herbicide resistance. The selective resistance mutation. Ala (122)-Pro, did not yield chlorsulfuron resistant transformants, as expected.

TABLE 12

Growth of Sugarbeet Calli Tansformed With a Tobacco SURB-Hra ALS Gene in the Presence of Increasing Concentrations of Chlorsulfuron

| Chlorsulfuron (ppb) | 0 | 10 | 30 | 100 | 300 | 1000 | 3000 | 10000 |
|---|---|---|---|---|---|---|---|---|
| 87193/152[1] | 15/15 | 15/15 | 15/15 | 15/15 | 15/15 | 15/15 | 3/15 | 0/15 |
| 97193/0[2] | 15/15 | 0/15 | 0/15 | nd | nd | nd | nd | nd |

[1]*Beta vulgaris* line 87193 transformed with *Agrobacterium tunefaciens* LBA4404 carrying plasmid pAGS152.
[2]Untransformed *Beta vulgaris* line 87193.

TABLE 13

Herbicide Resistance in Sugarbeet Cells Transformed with Site Specific Mutant Sugarbeet ALS Genes

| Gene Origin Mutation | Tobacco pro(197)-ala/trp (591)-Ieu | Sugarbeet pro(197)-ala/trp (591)-leu | Sugarbeet trp(591)-leu | Sugarbeet pro(197)-ala | Sugarbeet ala(122)-pro |
|---|---|---|---|---|---|
| Chlorsulfuron$^R$ | 47 | 36 | 20 | 24 | 0 |
| Hygromycin$^R$ | 93 | 97 | 95 | 98 | 98 |
| Chlorsulfuron$^R$/Hygromycin$^R$ | .51 | .37 | .21 | .24 | — |

Gene introductions were done by standard hypocotyl inocculation protocol. For each construction 100 hypocotyl wounds were cocultured and selected on chlorsulfuron at 10 μg/ml and 100 wounds were cocultured and selected on hygromycin at 10 ng/ml. The number of wound sites which developed resistant callus was counted 60 days after innoculation.

| Ingredient | Media and Amendments Stock | (Final) | Amt./Liter |
|---|---|---|---|
| ½ PG$_O$ | | | |
| PG$_O$ Majors A | 10X | | 50 ml |
| PG$_O$ Majors B | 100X | | 5 |
| FeEDTA | 100X | | 5 |
| B5 vitamins | 100X | | 5 |
| MS micronutrients | 1000X | | 1 |
| Sucrose | | 1.5% w/v | 15 gm |
| Mes buffer | | 3 mM | 590 mg |
| T.C. agar | | 0.8% w/v | 8 gm |
| pH 5.7, autoclave sterile, dispense aspectically into 15 × 150 mm petri plates. | | | |
| PG$_O$ $^{0.1}$/0.1 | | | |
| PG$_O$ Majors A | 10X | | 100 ml |
| PG$_O$ Majors B | 100X | | 10 |
| FeEDTA | 100X | | 10 |
| B5 vitamins | 100X | | 10 |
| MS micronutrients | 1000X | | 1 |
| Sucrose | | 3.0% w/v | 30 gm |
| Mes buffer | | 3 mM | 590 mg |
| 24-D | 1 mg/ml | | 100 μl |
| B1AP | 1 mg/ml | | 100 μl |
| pH 5.7, autoclave sterile. | | | |

PG$_O$$^{0.1}$/0.1 agar solidified, as above except with T.C. agar 0.8% w/v. Dispense 25 ml/25 × 100 petri dish.

| Stock | Ingredient | MW | (Final) | Amount/Liter |
|---|---|---|---|---|
| PG$_O$ Majors A (10X) | KNO$_3$ | 101.1 | 19.8 mM | 20 |
| | (NH$_4$)$_2$SO$_4$ | 132.14 | 3 | 4 |
| | KCl | 74.55 | 8 | 6 |
| | MgSO$_4$.7H$_2$O | 146.5 | 2 | 5 |
| | CaCl$_2$.2H$_2$O | 147.0 | 2 | 3 |
| PG$_O$ Majors B (100X) | NaH$_2$PO$_4$ | 120.0 | 2.1 mM | 25 |
| Fe EDTA (100X)M | FeSO$_4$ 7H$_2$O | | 100 μm | 2.78 gm |
| | Na$_2$EDTA | | 100 μm | 3.72 |
| Dissolve EDTA first. pH 3.0. Store @ 4° C., dark | | | | |
| B5 vitamins (100X) | Nicotinic acid | | 1 mg/lit | 0.1 gm |
| | Thiamine HCl | | 10 | 1.0 |
| | Pyridoxine HCl | | 1 | 0.1 |
| | Myo-inositol | | 100 | 10 |
| MS micronutrients (1000X) | MnCl$_2$ 4H$_2$O | 197.9 | 100 μm | 19800 mg |
| | H$_3$BO$_3$ | 01.8 | 100 | 6200 |
| | ZnSO$_4$ 7H$_2$O | 287.5 | 30 | 8625 |
| | KI | 166 | 5 | 830 |
| | NaMoO$_4$ 2H$_2$O | 206 | 1.2 | 250 |
| | CuSO$_4$ 5H$_2$O | 249.7 | 0.1 | 25 |

-continued

| Stock | Ingredient | MW | (Final) | Amount/Liter |
|---|---|---|---|---|
| | CoCl₂ 6H₂O | 237.9 | 0.1 | 25 |

Dissolve MnCl₂ 4H₂O in dil HCl
Dissolve one at a time and completely before adding next.
Boil, cool, pH 4.0, store dark at 4° C.

EXAMPLE VIII

The tobacco SURB-Hra gene encoding herbicide resistant ALS was used to transform *Brassica napus* cv. Olga by the following *Agrobacterium tumefaciens* mediated transformation procedure.

To surface sterilize seeds, they were immersed for 1 min. in 70% ethanol, then 30–60 min. in Clorox Tween (see EXAMPLE VII). The surface sterilized seeds were germinated on ½ MS, ½ PGO (SEE EXAMPLE VII), at 24° C. in the dark. At 5–10 days post germination, hypocotyls were divided into 0.5 cm sections and placed on solid I medium containing acetosyringone 100 μm (Aldrich Chemical)(IAS100).

Immediately the explants were dipped individually into a log phase suspension of LBA 4404 containing binary plasmid pAGS15.

The explants were plated onto IAS100. The Agrobacterium droplet was carefully dried down onto the tissue by leaving the plate open in a laminar flow hood. Co-cultivation was conducted at 24° C. in low light or darkness for 3 days.

After 3 days the explants were collected into liquid I medium containing cefotaxime 500 mg/L in 100×25mm petri dishes, and shaken on a gyrotory shaker at 40 rpm for 3 hrs.

The explants were plated on solid I medium containing cefotaxime 500mg/mL, and cultured for 3 days at 24° C. in low light.

The explants were plated on solid I medium containing vancomycin 100 mg/L and kanamycin 100 mg/L.

After about 1 month transformed callus appeared as discreet nodules at the ends of explants.

As nodules appeared, they were excised with a sharp scalpel and placed on solid I medium containing kanamycin 100 mg/L.

When transformed callus reached a sufficient size (0.5 cm diameter) it was transferred to KR medium containing kanamycin 100 mg/L. This material regenerates fastest if it is plated on fresh media every two weeks. Roots were regenerated on ½ MS containing IBA 2 μm.

In one experiment, of 100 wound sites (either end of 0.5 cm hypocotyl sector) 20 developed callus tissue which was resistant to kanamycin (100 mg/L). Five of the 20 transformed cell lines were subsequently induced to regenerate on kanamycin and somatic siblings for each regenerant genotype were produced by nodal multiplication. These plants were sprayed with various chlorsulfuron concentrations and the results are summarized in Table 14. Two of the five transformants are resistant to chlorsulfuron at levels which are about 10 times greater than that which is lethal to control (untransformed) plants.

TABLE 13

| | 0.3 ppm | 1 ppm | 3 ppm | 10 ppm |
|---|---|---|---|---|
| untransformed | ++ | + | − | − |
| R₀ #1 | ++ | ++ | ++ | + |
| R₀ #2 | ++ | + | − | − |

TABLE 13-continued

| | 0.3 ppm | 1 ppm | 3 ppm | 10 ppm |
|---|---|---|---|---|
| R₀ #3 | ++ | + | + | − |
| R₀ #4 | ++ | + | − | − |
| R₀ #5 | +++ | ++ | ++ | + |

+++ normal growth, no axial induction
++ reducted growth, sublethal at apis, axial induction
+ reduced growth, lethal at apis, axial induction
− lethal To further demonstrate the expression of the SURB-Hra gene in transformed *Brassica napus*, an ALS assay in the presence of the herbicide chlorsulfuron was performed as described in EXAMPLE VI. The ALS activities of the untransformed parent and transformant R₀ #5 (Table 14) were compared (Table 15). A consistent increase in the percent uninhibited ALS activity was observed in the transformant. Thus, the tobacco SURB-Hra gene, encoding herbicide-resistant ALS, can be expressed in *Brassica napus*, but that expression is not efficient. Addition of nucleotide regulatory sequences that provide higher level expression in *Brassica napus* would be expected to increase the level of herbicide resistant ALS and the level of tolerance to foliar applications of the herbicide.

TABLE 15

ALS Activity of Wild Type and Transformed *Brassica napus*

| | Percent Uninhibited ALS Activity[1] | | | | |
|---|---|---|---|---|---|
| | 0 ppb | 1 ppb | 10 ppb | 100 ppb | 1000 ppb |
| Wild Type | 100.0 | 86.6 | 28.2 | 10.1 | 7.6 |
| Transformant R₀ #5 | 100.0 | 88.1 | 36.6 | 20.1 | 14.5 |

[1]The ALS activities are relative to that in the absence of herbicide which is taken as 100 percent. The sulfonylurea compound used was chlorsulfuron (DPX-W4189), the active ingredient in Glean ® herbicide.

| *Brassica napus* Culture Media | | | |
|---|---|---|---|
| Ingredient | Stock | (Final) | Amount/Liter |
| I Media | | | |
| MS Major Salts | 10X | | 100 ml |
| MS Micronutrients | 1000X | | 1 ml |
| Fe EDTA | 100X | | 10 ml |
| I Vitamins | 100X | | 10 ml |
| 2,4-D | 1 mg/ml | | 0.2 ml |
| Kinetin | 1 mg/ml | | 3 ml |
| Sucrose | | 3% w/v | 30 gm |
| Mannitol | | 1.8% w/v | 18.2 gm |
| T.C. agar | | 0.8% w/v | 8 gm |
| Mes Buffer | | 3 mM | 0.59 gm |
| pH 5.7. autoclave sterile | | | |
| KR Media | | | |
| K3 Major Salts | 10X | | 100 ml |
| CaCl₂ 2H₂O | 100X | | 10 ml |
| MS Micronutrients | 1000X | | 1 ml |
| Fe EDTA | 100X | | 10 ml |
| B5 Vitamins | 100X | | 10 ml |
| Zeatin* | 1 mg/ml | | 2 ml |
| IAA* | 1 mg/ml | | 0.1 ml |
| Sucrose | | 1% w/v | 10 gm |
| Xylose | | 0.025% w/v | 0.25 gm |
| Agarose (Type 1, low E/Eo) | | 0.25% w/v | 2.5 gm |
| Mes Buffer | | 3 mM | 0.59 gm |
| pH 5.7, autoclave sterile | | | |

*add these filter sterilized components aseptically

| Brassica napus Stock Solutions | | | | |
|---|---|---|---|---|
| Stock | Ingredient | (Stock) | (Final) | Amount/Liter |
| MS Major Salts | NH₄NO₃ | 10X | 20.5 mM | 16.5 gm |
| | KNO₃ | | 18.8 | 19.0 |
| | MgSO₄ 7H₂O | | 1.5 | 3.7 |
| | KH₂PO₄ | | 1.25 | 1.7 |
| | CaCl₂ 2H₂O | | 3.0 | 4.4 |
| K3 Major Salts | KNO₃ | 10X | 25.0 mM | 25.0 gm |
| | (NH₄)₂SO₄ | | 1.0 | 1.34 |
| | MgSO₄ 7H₂O | | 1.0 | 2.5 |
| | KH₂PO₄ | | 1.5 | 2.01 |
| | NH₄NO₃ | | 3.1 | 2.5 |
| CaCl₂ 2H₂O | CaCl₂ 2H₂O | 100X | 6.3 mM | 92.3 gm |
| MS Micronutrients | MNCl₂ 4H₂O | 1000X | 100 μm | 19800 mg |
| | H₃BO₃ | | 100 | 6200 |
| | ZnSO₄ 7H₂O | | 30 | 8625 |
| | KI | | 5 | 830 |
| | NaMoO₄ 2H₂O | | 1.2 | 250 |
| | CuSO₄ 5H₂O | | 0.1 | 25 |
| | COCl₂ 6H₂O | | 0.1 | 25 |
| Fe EDTA | Na₂ EDTA | 100X | 100 μm | 3.73 gm |
| | FeSO₄ 7H₂O | | 100 | 2.78 |
| I Vitamins | Myo-Inositol | 100X | 100 mg/l | 1000 mg |
| | Thiamine | | 0.5 | 50 |
| | Glycine | | 2.0 | 200 |
| | Nicotinic acid | | 5.0 | 500 |
| | Pyrodoxine | | 0.5 | 50 |
| | Folic acid | | 0.5 | 50 |
| | Biotin | | 0.05 | 5 |

The explants were subcultured every 3-4 weeks, dissecting the more compact, darker green sectors away from the white fluffier callus.

When "morphogenic" callus (very dark green, compact, perhaps some recognizable leaves) was seen, it was transferred to regeneration media. The tissue can go directly to shoots instead of going through the morphogenic stage. Shoots were rooted in rooting media. Approximately 70% of the explants developed callus resistant to kanamycin at 100 μm/l. Transformed callus was put on media containing increasing concentrations of chlorsulfuron and growth in the presence of herbicide was determined by weighing the callus after 30 days (Table 16). Some transformants grew as well at high concentrations of chlorsulfuron (1000 ppb) as in its absence, e.g. Trans 1, Trans 2 and Trans 7. Thus the tobacco SURB-Hra gene can function to transform melon to high level herbicide resistance.

TABLE 16

| Chlorsulfuron ppb | Nontransformed | Trans 1 | Trans 2 | Trans 3 | Trans 4 | Trans 5 | Trans 6 | Trans 7 | Trans 8 | Trans 9 | Trans 10 |
|---|---|---|---|---|---|---|---|---|---|---|---|
| 0 | 5.7 | 30.4 | 30.4 | 30.4 | 30.4 | 30.4 | 30.4 | 26.4 | 28.3 | 27.2 | 40 |
| 50 | 0 | 44.5 | 19.5 | 10 | 14 | 175 | 28.8 | 46.5 | 18.1 | 27.3 | 40 |
| 100 | 0 | 25.9 | 0 | 7.5 | 16.6 | 70 | 18.3 | 25.5 | 14.9 | 11.1 | 39 |
| 500 | 0 | 51.9 | 14.8 | 0 | 0 | 3.7 | 2 | 16.1 | 2 | 10.4 | 18.6 |
| 1000 | 0 | 46 | 26 | 11.7 | 10 | 5.7 | 4.7 | 19.3 | 2.6 | 9 | 27.6 |
| 2000 | 0 | 19.1 | 8 | 28.7 | 5 | 0 | 0 | 19.3 | 0 | 8.8 | 23.5 |
| 3000 | 0 | 15.2 | 18 | 0 | 0 | 0 | 0 | 17.1 | 10 | 13.7 | 17.6 |
| 4000 | 0 | 41.9 | 3.3 | 0 | 0 | 0 | 0 | 20.7 | 3.4 | 3 | 7.6 |
| 5000 | 0 | 14.4 | 0 | 3.6 | 0 | 0 | 0 | 26.5 | 7.4 | 2.6 | 8.9 |

Measurements indicate fold increase in weight of callus.

| Media | |
|---|---|
| Oms | |
| MS Salts and Fe EDTA | 1X |
| B5 Vitamins | 1X |
| Sucrose | 3% |
| MES | 3 mM |
| pH 5.7 | |
| T.C. agar | 0.8% |
| Autoclave 20 min. | |
| Basic medium | |
| MS Salts and Fe EDTA | 1X |
| Myo inositol | 100 mg/l |
| Thiamine | 1 mg/l |
| Sucrose | 3% |
| MES | 3 mM |
| pH 5.7 | |
| T.C. agar | 0.8% |
| Autoclave 20 min. | |
| Co-cultivation Medium is Basic medium plus: | |
| Acetosyringone 100 μm (acetosyringone is kept as a 100 mM stock in DMSO) | |
| Kinetin | 6 mg/l |
| IAA | 1.5 mg/l |
| Washing medium is Basic Medium without agar plus: | |
| Cefotaxime | 500 mg/l |
| Kinetin | 6 mg/l |
| IAA | 1.5 mg/l |
| Selection Medium is Basic Medium plus: | |
| Kinetin | 6 mg/l |
| IAA | 1.5 mg/l |
| Vancomycin | 100 mg/l |
| One of the following selective drugs depending upon Agrobacterium construction: | |
| Kanamycin | 100 mg/l |
| Hygromycin | 50 mg/l |
| Chlorsulfuron | 100 mg/l |
| Regeneration Medium is Basic Medium plus: | |
| BAP | 0.1 mg/l |
| Vancomycin | 100 mg/l |
| Selective drugs as above | |

EXAMPLE IX

The tobacco SURB-Hra gene encoding herbicide resistant ALS was used to transform *Cucumis melo* cv. Amarillo Oro (melon) to herbicide resistance by the following *Agrobacterium tumefaciens* mediated transformation procedure. A reference to this procedure is Moreno, V., et al. Plant regeneration from calli of melon. Plant Cell Tissue Organ Culture, 5 (1985) 139-146.

Surface sterilization of seeds was greatly facilitated by first removing the seed coat. The seeds were then sterilized by rinsing in 70% ethanol for 2 min., then washing in Clorox/Tween (see EXAMPLE VII) for 20 mins. The sterile seeds were washed 3 times in sterile distilled H₂O and germinated on OMS at 24° C. with a 16 hr. day length.

Cotyledons of 7-14 day old melon seedlings were cut into 5 mm slices with a fresh, sharp scalpel. These explants were dipped into a log phase Agrobacterium culture prepared as described in EXAMPLE I, transferred to fresh co-cultivation plates and cultured at 24° C. with 16 hr. days for 3 days.

The bacteria were killed by washing the explants for 3 hrs. with gentle agitation in washing media and cultured on fresh selection plates.

| Media | |
|---|---|
| Rooting Medium is OMS plus: | |
| IBA | 2 μm |
| Vancomycin | 100 mg/l |
| Selective drugs as above | |

EXAMPLE X

The tobacco SURB-Hra gene encoding herbicide resistant ALS was used to transform *Medicago satira* cv. Rangelander (alfalfa) to herbicide resistance by the following *Agrobacterium tumefaciens* mediated transformation procedure. A reference to this procedure is Deak, M., Kiss, G., Koncz, C., and Dudits, D. Transformation of Medicago by Agrobacterium mediated gene transfer (preprint).

Plants were grown and subcultured in OMS. The materials used were petioles and stem segments (5 mm in length) from plants about 2 months from the last subculture.

The petioles and stems of sterile plants were cut into 5 mm lengths with a fresh, sharp scalpel. These explants were dipped into a log phase Agrobacterium culture prepared as described in EXAMPLE I, transferred to fresh co-cultivation plates, and cultured at 24° C. with 16 hr. days for 3 days.

The bacteria were killed by washing the explants for 3 hrs. with gentle agitation in washing media, and cultured on fresh selection plates.

The explants were subcultured every 3–4 weeks. In about 1 month transformed callus growing out of the wounded ends of the explants was seen, dissected away from the explant and plated on fresh selection media. When callus became more organized, (areas are darker green and more compact) it was transferred to fresh maturation media.

When developed embryos appeared, they were transferred to germination media. After germination, the small plants were grown on the same medium.

Less than 1% of explants developed callus resistant to kanamycin at 100 mg/L. Kanamycin resistant sectors were found to be resistant to the herbicide chlorsulfuron at 50 ppb. Three shoots were produced from kanamycin resistant callus. Tissue from these transformants was assessed for herbicide resistant growth over a range of chlorsulfuron concentrations. One transformant was able to grow at 1000 ppb chlorsulfuron; the other two were able to grow at 5000 ppb. Thus, the tobacco SURB-Hra gene can function to transform alfalfa to high level herbicide resistance.

| Media | |
|---|---|
| OMS | |
| MS Salts and Fe EDTA | 1X |
| B5 Vitamins | 1X |
| Sucrose | 3% |
| MES | 3 mM |
| pH 5.7 | |
| T.C. agar | 0.8% |
| Autoclave 20 min | |
| Basic Medium | |
| MS Salts and Fe EDTA | 1X |
| UM Vitamins | 1X* |
| Sucrose | 3% |
| pH 5.7 | |
| T.C. agar | 0.8% |
| Autoclave 20 min. | |

| Media | |
|---|---|
| *100X UM vitamins | |
| (amounts given for 100 ml of 100x stock) | |
| Thiamine HCl | 1 g |
| Nicotinic acid | 0.5 g |
| Pyridoxine HCl | 1 g |
| Myo inositol | 10 g |
| Glycine | 0.2 g |
| Co-Cultivation Medium | |
| Basic Medium plus | |
| Acetosyringone 100 μm (Acetosyringone | |
| is kept as a stock of 100 mM in DMSO) | |
| 2,4-D | 0.5 mg/l |
| BAP | 0.2 mg/l |
| Washing Medium | |
| Basic Medium without agar plus | |
| Cefotaxime | 500 mg/l |
| 2,4-D | 0.5 mg/l |
| BAP | 0.2 mg/l |
| Selection Medium | |
| Basic Medium plus | |
| 2,4-D | 0.5 mg/l |
| BAP | 0.2 mg/l |
| Vancomycin | 100 mg/l |
| One of the following selective drugs, | |
| depending upon Agrobacterium construction: | |
| Hygromycin | 50 mg/l |
| Chlorsulfuron | 100 mg/l |
| Maturation Medium | |
| Same as selection medium without 2,4-D | |
| Germination Medium | |
| Basic Medium plus | |
| Vancomycin | 100 mg/l |
| Selective drugs as above | |

EXAMPLE XI

Sulfonylurea herbicide-resistant mutants of *Arabidopsis thaliana* (L.) Heyrib were isolated as follows: M1 plants derived from approximately 100,000 ethyl methane sulfonate-mutagenized wild type seeds were self-fertilized. Approximately 30,000 of the resultant M2 seeds were placed on a medium containing 200 nM (75 ppb) chlorsulfuron, a concentration that completely inhibits germination of the wild type seeds. Four seeds germinated in the presence of chlorsulfuron. The herbicide resistance trait in one mutant, designated GH50, was shown to be stably inherited and to be due to a single, dominant nuclear mutation. Plants carrying the mutation were resistant to concentrations of chlorsulfuron and sulfometuron methyl that were at least 100-fold and 10-fold, respectively, higher than that required to inhibit wild type plants. The concentrations of chlorsulfuron and sulfometuron methyl required to inhibit 50% of the in vitro ALS activity in leaf extracts of the mutant were 1000-fold and 100-fold, respectively, greater than that required for the wild type.

A genomic library of DNA from Arabidopsis which was homozygous for the herbicide resistance mutation of GH50 was made in bacteriophage lambda, and was screened for recombinant clones which hybridized to the previously isolated gene encoding a herbicide-sensitive ALS from wild type Arabidopsis. A phage clone was identified which contained a 6.1 kilobase Xba I DNA fragment that hybridized to the wild type ALS gene. This Xba I fragment was isolated and inserted into the Xba I site of plasmid pKNKX. Plasmid pKNKX contains a bacterial gene NPT II, that encodes neomycin phosphotransferase, fused to regulatory signals, the nopaline synthase promoter (NOSP) and transcription terminator, allowing expression in plants and resulting in kanamycin resistance. Plasmid pKNKX was constructed as follows:

The precursor vector pKNK was derived from the commonly used plasmid pBR322 by removing the Hind III and BamH I sites and inserting at the Cla I site an approximately 2.3 kb Cla I fragment which incorporated (a) a 320 bp Cla I-Bgl II sequence containing the promoter region of the neomycin phosphotransferase (NPT II) gene of transposon Tn 5 derived by the conversion of a Hind III site to the Cla I site [Beck, E., Ludwig, G., Auerswald, E. A., Reiss, B. & Schaller. H. (1982) Gene 19:327–336], (b) a 296 bp Sau 3A-Pst I sequence containing the hopaline synthase promoter derived from the nopaline synthase gene (NOS) (nucleotides −263 to +33, with respect to the transcription start site [Depicker, A., Stachel, S., Dhaese, P., Zambryski, P & Goodman, H. J. (1982) J. Mol. Appl. Genet. 1:561–574] by the creation of a Pst I site at the initiation codon, (c) the 998 bp Hind III-BamH I sequence containing the coding sequence for the NPT II gene derived from Tn 5 by the creation of Hind III and BamH I sites at nucleotides 1540 and 2518 [Beck, E., Ludwig, G., Auerswald, E. A., Reiss, B. & Schaller, H. (1982) Gene 19:327–336], respectively, and (d) the 702 bp BamH I-Cla I sequence containing the 3' region of the NOS gene (nucleotides 848 to 1550) [Depicker, A., Stachel, S., Dhaese, P., Zambryski, P. & Goodman, H. J. (1982) J. Mol. Appl. Genet. 1:561–574]. The nucleotide sequence at the fusion of the NOSP and the NPT II coding sequence is inserted in the Sal1 site proximal to the ampicillin-resistance gene on the vector.

Plasmid pKAR was conjugated into *Agrobacterium tumefaciens* by triparental mating. Three ml overnight cultures of *E. coli* HB101 (pKAR) and *E. coli* HB101 (pRK2013) (ATCC number 37159) in LB liquid medium containing 25 mg/L kanamycin were grown at 37° C. and of *Agrobacterium tumefaciens* GV3850 in LB medium were grown at 28°–29° C. The cells were harvested at room temperature in a clinical centrifuge, washed once in LB medium without drug, harvested, and resuspended in 3 ml of LB. 0.25 ml aliquots of all three strains were mixed in a tube and the mixture was transferred onto a Millipore filter (2.5 cm HAWP, 0.45 μm) placed on top of three Whatman No. 1 filters in a petri dish. After all of the liquid medium was absorbed by the Whatman filter (about 30 min), the Millipore filter with bacteria on its top surface was laid (bacteria side up) onto a LB plate without drug. After incubation overnight at 28°–29° C. the Millipore filter was transferred to 5 ml of 10 mMMgSO4 and vortexed to resuspend the bacteria in the solution. 0.1 ml aliquots were plated on selective plates [M9 minimal plates containing 20% sucrose, 1 mMMgSO4, 1 mM CaCl2, and 1 mg/ml kanamycin (Sigma)]. Several large colonies showed up after about four days of incubation at 28°–29° C. Several transconjugants were purified by three successive single-colony streakings on the same selective plates. Only Agrobacteria containing the plasmid pKAR recombined with the endogenous pGV3850 plasmid through

| NOS Sequence | NPT II Sequence |
|---|---|
| ... ... AATAAT<u>CTGCAG</u>C<u>AAGCTT</u>GCGGGGATCGTTCGC ATG ... ... | |
| Pst I     HindIII | |

Plasmid pKNK was, sequentially, linearized by digestion with restriction enzyme Sal I, its ends made blunt by *E. coli* DNA polymerase I, Klenow fragment, and joined in the presence of T4 DNA ligase to phosphorylated Xba I linkers (5'-CTCTAGAG-3'). The excess linkers were removed by Xba I digestion, followed by agarose gel electrophoresis. The linear plasmid DNA was isolated by electroelution, purified through a NACS column (BRL) and self-ligated in the presence of T4 DNA ligase. Ligated DNA was used to transform competent *E. coli* HB101 cells. Ampicillin-resistant cells were shown to contain plasmid pKNKX, which is identical to pKNK except for the addition of an Xba I site next to the Sal I site.

Plasmid pKNKX was sequentially linearized with restriction enzyme Xba I, dephosphorylated with calf intestine phosphatase, phenol extracted, and joined in the presence of T4 DNA ligase to an approximately 6.1 kb Xba I fragment containing the mutant Arabidopsis ALS gene. The resulting plasmid, pKNKAR, has the open reading frames of the ALS gene and the NOS:NPT II gene in the vector in the same orientation. The Xba I insert is flanked by Sal I sites.

Plasmid pKNKAR was partially digested by restriction enzyme Sal I and, following phenol extraction, joined to a 1.25 kb Sal I fragment containing the bacterial NPT I gene for bacterial kanamycin selectable marker. The ligated molecules were used to transform competent *E. coli* HB101 cells and a kanamycin-resistant colony was shown to contain the recombinant plasmid pKAR (FIG. 9), in which the NPTI fragment was their common pBR322 sequences were expected to grow. This was confirmed by Southern analysis before using the engineered Agrobacterium for plant transformations.

Another transconjugant, GVKAS, was made, which was essentially identical to GVKAR, except that it had the 6.1 kb Xba X fragment derived from the herbicide-sensitive *Arabidopsis thaliana*.

For plant cell transformations, standard aseptic techniques for the manipulation of sterile media and axenit plant/bacterial cultures were followed, including the use of a laminar flow hood for all transfers. Recipes for media are given in Example VI. Potted tobacco plants for leaf disk infections were grown in a growth chamber maintained for a 12 hr. 24° C. day, 12 hr, 20° C. night cycle, with approximately 80% relative humidity, under mixed cool white fluorescent and incandescent lights. Tobacco leaf disk infections were carried out essentially by the method of Horsch et al. (1985) Science 227, 1229.

Young leaves, not fully expanded and approximately 4–6 inches in length, were harvested with a scalpel from approximately 4–6 week old tobacco plants (*Nicotiana tabacum* vat. Xanthi). The leaves were surface sterilized for 30 minutes by submerging them in approximately 500 ml of a 10% Chlorox, 0.1% SDS solution and then rinsed 3 times with sterile deionized water. Leaf disks, 6 mm in diameter, were prepared from whole leaves using a sterile paper punch.

Leaf disks were inoculated by submerging them for several minutes in 20 ml of a 1:10 dilution of an overnight Agrobacterium culture carrying the desired plasmid. Agrobacterium cultures were started by inoculating 10 ml of YEB broth with a single bacterial colony removed from an R-agar plate. The culture was grown for approximately 17-20 hours in 18 mm glass culture tubes in a New Brunswick platform shaker maintained at 28° C.

After inoculation, the leaf disks were placed in petri dishes containing CN agar medium. The dishes were sealed with parafilm and incubated under mixed fluorescent and "Gro and Sho" plant lights (General Electric) for 2-3 days in a culture room maintained at approximately 25° C.

To rid the leaf disks of Agrobacterium and to select for the growth of transformed tobacco cells, the leaf disks were transferred to fresh CN medium containing 500 mg/L cefotaxime and 100 mg/L kanamycin. Cefotaxime was kept as a frozen 100 mg/ml stock solution and added aseptically (filter sterilized through a 0.45 μm filter) to the media after autoclaving. A fresh kanamycin stock (50 mg/ml) was made for each use and was filter sterilized into the autoclaved media.

Leaf disks were incubated under the growth conditions described above for 3 weeks and then transferred to fresh media of the same composition. Shoots which developed on kanamycin-selected explants were excised and placed in rooting medium A containing 100 mg/L kanamycin. After two weeks, several small leaves were excised from each shoot, sliced into 2-3 mm pieces, and placed on callus induction medium B containing either 50 mg/L kanamycin, 10 ppb chlorsulfuron, or no selective agent. Callus formation was scored after three weeks of growth at approximately 25° C. on a 12-hour light/12-hour dark cycle. Seventeen of 19 transformants which received the sulfonylurea-resistant Arabidopsis ALS gene formed secondary callus on 10 ppb chlorsulfuron; none of 22 transformants which received the sulfonylurea-sensitive Arabidopsis ALS gene formed callus on the same medium.

Callus lines derived from transformed shoots were subcultured several times to generate quantities of relatively uniform callus. Growth responses to chlorsulfuron of these cell lines were tested by spreading approximately 50 mg of tissue on sterile double paper filter disks (Whatman #1) placed on the surface of callus medium B containing a series of chlorsulfuron concentrations. Cultures were incubated for two weeks under the conditions described above and then tissue was scraped from each filter and weighed. Means and standard errors of means were calculated from eight replicates for each cell line on each herbicide concentration. Tobacco callus lines derived from transformants which received the sulfonylurea-resistant Arabidopsis ALS gene were able to grow on chlorsulfuron concentrations 100 to 300 times higher than those tolerated by lines derived from transformants which received the gene encoding sulfonylurea-sensitive ALS (Table 17).

Plants confirmed as transformants by rooting in 100 mg/L kanamycin and by secondary leaf callus formation on 50 mg/L kanamycin were transplanted to soil. After 25-40 days of growth, extracts were prepared from two or three young, expanding leaves per plant and assayed for ALS activity. For each extract, reactions containing either no herbicide or 100 ppb chlorsulfuron were sampled at 10, 20, 30 and 40 minutes and the data used to calculate rate of product formation. ALS extracted from transformants which received the sulfonylurea-resistant ALS gene was inhibited 32-60% under these reaction conditions, while enzyme extracted from transformants which received the sulfonylurea-sensitive ALS gene was inhibited 94-97% (Table 18).

The plants assayed above were forced to self-pollinate by placing paper bags over immature flower heads. Seeds derived from these self-pollinations were surface sterilized by stirring for 30 minutes in 10% Chlorox, 0.1% SDS, rinsed three times in sterile deionized water, and plated on MMO medium containing a series of chlorsulfuron concentrations. Progeny of transformants which received the sulfonylurea-resistant ALS gene showed simple Mendelian inheritance for the ability to germinate and grow on chlorsulfuron concentrations as high as 3000 ppb, while progeny of transformants which received the sulfonylurea-sensitive ALS gene failed to survive on 30 ppb chlorsulfuron (Table 19).

TABLE 17

Growth Responses to Chlorsulfuron of Tobacco Callus Lines Derived From Transformants Which Received Arabidopsis ALS Genes Means and Standard Errors of Means Calculated from Eight Replicates

| Callus Line | Chlorsulfuron Concentration (ppb) | Weight (mg) | % Uninhibited Growth |
|---|---|---|---|
| GVKAS[1] #4 | 0 | 2748 ± 202 | 100 |
| | 0.1 | 1576 ± 123 | 57.0 |
| | 0.3 | 452 ± 26 | 16.4 |
| | 1 | 74 ± 5 | 2.7 |
| GVKAS[1] #9 | 0 | 2330 ± 197 | 100 |
| | 0.1 | 2474 ± 163 | 106.2 |
| | 0.3 | 492 ± 41 | 21.1 |
| | 1 | 100 ± 7 | 4.3 |
| GVKAS[1] #13 | 0 | 1659 ± 107 | 100 |
| | 0.1 | 1242 ± 83 | 74.9 |
| | 0.3 | 220 ± 17 | 13.2 |
| | 1 | NG | NG |
| GVKAR[2] #7 | 0 | 1782 ± 125 | 100 |
| | 10 | 1121 ± 60 | 62.9 |
| | 30 | 1053 ± 65 | 59.1 |
| | 100 | 278 ± 19 | 15.6 |
| | 300 | 65 ± 3 | 3.6 |
| GVKAR[2] #9B | 0 | 1800 ± 88 | 100 |
| | 10 | 1228 ± 67 | 68.2 |
| | 30 | 992 ± 79 | 55.1 |
| | 100 | 278 ± 13 | 15.4 |
| | 300 | 85 ± 5 | 4.7 |
| GVKAR[2] #25 | 0 | 1655 ± 60 | 100 |
| | 10 | 339 ± 25 | 20.5 |
| | 30 | 247 ± 16 | 14.9 |
| | 100 | 116 ± 7 | 7.0 |
| | 300 | NG | NG |

[1]Transformed cell line derived from transformed plant generated by infection of tobacco leaf disks with Agrobacterium strain GV3850 containing a Ti plasmid carrying the sulfonylurea-sensitive Arabidopsis ALS gene.
[2]Transformed cell line derived from transformed plant generated by infection of tobacco leaf disks with Agrobacterium strain GV3850 containing a Ti plasmid carrying the sulfonylurea-resistant Arabidopsis ALS gene.

TABLE 18

ALS Enzyme Activities in Tobacco Transformants Which Received Arapidopsis ALS Genes (ΔOD530/mg/minute) × 100

| Plant | No Herbicide | 100 ppb Clhorsulfuron | % Uninhibited Activity |
|---|---|---|---|
| GVKAS[1] #13 | 1.172 | 0.074 | 6.3 |
| GVKAS[1] #1.5 | 1.244 | 0.048 | 3.9 |
| GVKAS[1] #18 | 0.553 | 0.014 | 2.5 |
| GVKAR[2] #7 | 1.724 | 0.766 | 44.4 |
| GVKAR[2] #9 | 0.694 | 0.412 | 59.4 |
| GVKAR[2] #9A | 0.679 | 0.434 | 63.9 |
| GVKAR[2] #9B | 1.081 | 0.714 | 66.0 |

TABLE 18-continued

ALS Enzyme Activities in Tobacco
Transformants Which Received Arapidopsis ALS Genes
($\Delta$OD530/mg/minute) × 100

| Plant | No Herbicide | 100 ppb Clhorsulfuron | % Uninhibited Activity |
|---|---|---|---|
| GVKAR[2] #25 | 0.861 | 0.341 | 39.6 |

[1]Transformed plant generated by infection of tobacco leaf disks with Agrobacterium strain GV3850 containing a Ti plasmid carrying the sulfonylurea-sensitive Arabidopsis ALS gene.

[2]Transformed plant generated by infection of tobacco leaf disks with Agrobacterium strain GV3850 containing a Ti plasmid carrying the sulfonylurea-resistant Arabidopsis ALS gene.

TABLE 19

Germination of Seeds Derived From Self-Pollinations of
Tobacco Transformants Which Received Arabidopsis ALS Genes

| Selfed Plant | Resistant | Sensitive |
|---|---|---|
| GVKAS[1] #4 | | |
| 30 ppb Chlorsulfuron | 0 | 45 |
| 300 ppb Chlorsulfuron | 0 | 22 |
| GVKAS[1] #9 | | |
| 30 ppb Chlorsulfuron | 0 | 28 |
| 300 ppb Chlorsulfuron | 0 | 28 |
| GVKAS[1] #13 | | |
| 30 ppb Chlorsulfuron | 0 | 62 |
| 300 ppb Chlorsulfuron | 0 | 48 |
| GVKAR[2] #7 | | |
| 300 ppb Chlorsulfuron | 43 | 9 |
| 1000 ppb Chlorsulfuron | 37 | 14 |
| 3000 ppb Chlorsulfuron | 30 | 15 |
| GVKAR[2] #9 | | |
| 300 ppb Chlorsulfuron | 44 | 14 |
| 1000 ppb Chlorsulfuron | 35 | 15 |
| 3000 ppb Chlorsulfuron | 38 | 15 |
| GVKAR[2] #25 | | |
| 300 ppb Chlorsulfuron | 52 | 15 |
| 1000 ppb Chlorsulfuron | 47 | 22 |
| 3000 ppb Chlorsulfuron | 39 | 32 |

[1]Transformed plant generated by infection of tobacco leaf disks with Agrobacterium GV3850 containing a Ti plasmid carrying the sulfonylurea-sensitive Arabidopsis ALS gene.

[2]Transformed plant generated by infection of tobacco leaf disks with Agrobacterium strain GV3850 containing TI plasmid carrying the sulfonylurea-resistant Arabidopsis ALS gene.

MMO Medium
Murashige and Skoog Major Salts
Murashige and Skoog Minor Salts
30 grams/L Sucrose
100 mg/L i-Inositol
0.4 mg/L Thiamine-HCL
pH 5.8
0.8% Agar

What is claimed is:

1. An isolated nucleic acid fragment comprising a nucleotide sequence encoding a plant acetolactate synthase protein, said nucleic acid fragment is capable of being incorporated into a nucleic acid construct used to transform a plant containing wild-type acetolactate synthase protein which is sensitive to a compound selected from the group consisting of sulfonylurea, triazolopyrimidine sulfonamide, and imidazolinone herbicides, said nucleic acid fragment having at least one point mutation relative to the wild-type nucleic acid fragment encoding plant acetolactate synthase protein such that upon transformation with said nucleic acid construct said plant is rendered resistant to the application of said herbicide compound.

* * * * *